US006586182B1

(12) United States Patent
Patten et al.

(10) Patent No.: US 6,586,182 B1
(45) Date of Patent: *Jul. 1, 2003

(54) METHODS AND COMPOSITIONS FOR POLYPEPTIDE ENGINEERING

(75) Inventors: Phillip A. Patten, Mountain View; Willem P. C. Stemmer, Los Gatos, both of CA (US)

(73) Assignee: Maxygen, Inc., Redwood City, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 201 days.

This patent is subject to a terminal disclaimer.

(21) Appl. No.: 09/693,389

(22) Filed: Oct. 20, 2000

Related U.S. Application Data

(63) Continuation of application No. 08/769,062, filed on Dec. 18, 1996, now Pat. No. 6,335,160.

(51) Int. Cl.$^7$ .................................................. C12Q 1/68
(52) U.S. Cl. ........................... 435/6; 435/7.1; 435/69.1; 435/91.2; 435/194; 435/196; 435/471; 435/472; 530/300; 530/350; 536/23.1
(58) Field of Search ............................ 435/6, 7.1, 91.2, 435/69.1, 455, 471, 472, 194, 196; 536/23.1; 530/300, 350

(56) References Cited

U.S. PATENT DOCUMENTS

| | | | |
|---|---|---|---|
| 4,766,106 A | 8/1988 | Katre et al. |
| 4,795,699 A | 1/1989 | Tabor et al. |
| 4,816,567 A | 3/1989 | Cabilly et al. |
| 4,902,502 A | 2/1990 | Nitecki et al. |
| 5,264,563 A | 11/1993 | Huse |
| 5,314,809 A | 5/1994 | Erlich et al. |
| 5,427,930 A | 6/1995 | Birkenmeyer et al. |
| 5,498,531 A | 3/1996 | Jarrell |
| 5,501,962 A | 3/1996 | Bradford-Goldberg et al. |
| 5,512,463 A | 4/1996 | Stemmer |
| 5,514,568 A | 5/1996 | Stemmer |
| 5,514,588 A | 5/1996 | Varadaraj |
| 5,523,388 A | 6/1996 | Huse |
| 5,538,868 A | 7/1996 | Horn et al. |
| 5,541,311 A | 7/1996 | Dahlberg et al. |
| 5,547,859 A | 8/1996 | Goodman et al. |
| 5,574,205 A | 11/1996 | Kucherlapati et al. |
| 5,665,859 A | 9/1997 | Wallach et al. |
| 5,667,974 A | 9/1997 | Birkenmeyer et al. |
| 5,698,426 A | 12/1997 | Huse |
| 5,708,153 A | 1/1998 | Dower et al. |
| 5,741,694 A | 4/1998 | Hasrtup et al. |
| 5,756,316 A | 5/1998 | Schellenberger |
| 5,770,434 A | 6/1998 | Huse |

(List continued on next page.)

FOREIGN PATENT DOCUMENTS

| | | |
|---|---|---|
| AU | 732146 | 6/1998 |
| AU | 724698 | 10/1998 |
| AU | 703264 | 3/1999 |
| EP | 0 316 018 A2 | 5/1989 |
| EP | 0 316 018 A3 | 5/1989 |
| EP | 0 385 410 B1 | 1/1990 |
| EP | 0 397 463 A2 | 11/1990 |
| EP | 0 397 463 A3 | 11/1990 |
| EP | 0 439 182 B1 | 7/1991 |
| EP | 0 596 918 B1 | 5/1994 |
| EP | 0 633 944 B1 | 1/1995 |
| EP | 1 103 606 A3 | 12/1996 |
| EP | 1 103 606 A2 | 12/1996 |
| EP | 0 876 509 B1 | 11/1998 |
| EP | 0 544 809 B1 | 12/1998 |
| EP | 0 563 296 B1 | 3/1999 |
| EP | 0 911 396 A3 | 4/1999 |
| EP | 0 911 396 A2 | 4/1999 |
| EP | 0 552 266 B1 | 1/2000 |
| EP | 1 094 108 A2 | 4/2001 |
| EP | 1 094 108 A3 | 4/2001 |
| JP | 04 229 200 | 8/1992 |
| WO | WO 86/05803 A1 | 10/1986 |
| WO | WO 90/00626 A1 | 1/1990 |
| WO | WO 90/14424 A1 | 11/1990 |

(List continued on next page.)

OTHER PUBLICATIONS

Kanehisa et al. 1984 Computer analysis and structure prediction of nucleic acids and proteins. Nuc. Acids Res. 12(1):417–428.*

Rouwendal et al. (1996) "Ligase chain reactions for site–directed in vitro mutagenesis." *Methods Mol Biol* 57:149–156.

Shabarova et al. (1991) "Chemical ligation of DNA: the first non–enzymatic assembly of a biologically acive gene." *Nucleic Acids Res.* 19(15):4247–4251.

Shao et al. (1996) Éngineering new functions ans altering existing functions. *Curr Opin. Struct Biol* 6(4):513–518.

Shao et al. (1998) "Random–priming in vitro recombination: an effective tool for directed evolution." *Nucleic Acids Res.* 26(2):681–683.

(List continued on next page.)

*Primary Examiner*—Stephanie Zitomer
(74) *Attorney, Agent, or Firm*—Norman J. Kruse; Christopher C. Sappenfield; Quine Intellectual Property Law Group

(57) ABSTRACT

Methods are provided for the evolution of proteins of industrial and pharmaceutical interest, including methods for effecting recombination and selection. Compositions produced by these methods are also disclosed.

27 Claims, 8 Drawing Sheets

U.S. PATENT DOCUMENTS

| | | | |
|---|---|---|---|
| 5,792,607 A | 8/1998 | Backman et al. | |
| 5,795,747 A | 8/1998 | Henco | |
| 5,808,022 A | 9/1998 | Huse | |
| 5,824,496 A | 10/1998 | Horwitz et al. | |
| 5,830,696 A | 11/1998 | Short | |
| 5,830,721 A | * 11/1998 | Stemmer et al. | 435/172.1 |
| 5,837,500 A | 11/1998 | Ladner et al. | |
| 5,843,643 A | 12/1998 | Ratner | |
| 5,858,725 A | 1/1999 | Crowe | |
| 5,866,363 A | 2/1999 | Pieczenic | |
| 5,871,974 A | 2/1999 | Huse | |
| 5,877,402 A | 3/1999 | Maliga et al. | |
| 5,885,813 A | 3/1999 | Davis et al. | |
| 5,928,905 A | 7/1999 | Stemmer et al. | |
| 5,955,358 A | 9/1999 | Huse | |
| 5,965,415 A | 10/1999 | Radman et al. | |
| 6,001,574 A | 12/1999 | Short | |
| 6,004,788 A | 12/1999 | Short | |
| 6,015,694 A | 1/2000 | Dubenskey et al. | |
| 6,030,779 A | 2/2000 | Short | |
| 6,051,049 A | 4/2000 | Hansen et al. | |
| 6,054,267 A | 4/2000 | Short | |
| 6,057,103 A | 5/2000 | Short | |
| 6,071,889 A | 6/2000 | Weiss et al. | |
| 6,074,853 A | 6/2000 | Pati et al. | |
| 6,087,177 A | 7/2000 | Wohlstadter | |
| 6,093,873 A | 7/2000 | Chambon et al. | |
| 6,114,115 A | 9/2000 | Wagner, Jr. | |
| 6,153,410 A | 11/2000 | Arnold et al. | |
| 6,159,687 A | 12/2000 | Vind | |
| 6,168,919 B1 | 1/2001 | Short | |
| 6,171,820 B1 | 1/2001 | Short | |
| 6,174,673 B1 | 1/2001 | Short et al. | |
| 6,177,263 B1 | 1/2001 | Arnold et al. | |
| 6,180,406 B1 | 1/2001 | Stemmer | |
| 6,238,884 B1 | 5/2001 | Short et al. | |
| 6,280,926 B1 | 8/2001 | Short | |
| 6,287,861 B1 | 9/2001 | Stemmer et al. | |
| 6,291,158 B1 | 9/2001 | Winter et al. | |
| 6,291,161 B1 | 9/2001 | Lerner et al. | |
| 6,291,242 B1 | 9/2001 | Stemmer | |
| 6,297,053 B1 | 10/2001 | Stemmer | |
| 6,303,344 B1 | 10/2001 | Patten et al. | |

FOREIGN PATENT DOCUMENTS

| | | |
|---|---|---|
| WO | WO 92/06176 A1 | 4/1992 |
| WO | WO 92/18645 A1 | 10/1992 |
| WO | WO 93/00447 A1 | 1/1993 |
| WO | WO 93/01282 A1 | 1/1993 |
| WO | WO 93/18175 A1 | 9/1993 |
| WO | WO 93/19172 A1 | 9/1993 |
| WO | WO 93/20227 A1 | 10/1993 |
| WO | WO 93/24656 A1 | 12/1993 |
| WO | WO 94/08047 A1 | 4/1994 |
| WO | WO 94/11496 A1 | 5/1994 |
| WO | WO 94/12632 A1 | 6/1994 |
| WO | WO 96/17056 A1 | 6/1996 |
| WO | WO 97/07206 A1 | 2/1997 |
| WO | WO 97/20918 A1 | 6/1997 |
| WO | WO 97/35957 A1 | 10/1997 |
| WO | WO 97/46670 A1 | 12/1997 |
| WO | WO 98/13485 A1 | 4/1998 |
| WO | WO 98/13487 A1 | 4/1998 |
| WO | WO 98/27230 A1 | 6/1998 |

OTHER PUBLICATIONS

Shimmer et al. (1995) "Ligase chain reaction." *Methods Mol Biol* 46:269–278.

Shuldner et al. (1990) "PCR–induced (ligase–free) subcloning: a rapid reliable method to subclone polymerase chain reaction (PCR) products." *Nucleic Acids Res.* 18(7):1920.

Strausberg et al. (1995) "directed evolution of a subtilisin with calcium–independent stability." *Biotechnology* 13(7):669–673.

Szostak (1997) "In vitro selection and directed evolution." *Harvey Lect* 93:95–118.

Tortoli et al. (1997) "Evaluation of a commercial ligase chain reaction kit (Abbort LCx) for directed detection of Mycobacterium tuberculosis in pulmonary and extrapulmonary specimens." *J. Clin. Microbiol.* 35(9):2424–2426.

You et al. (1996) "Directed evolution of subtilisin E in Bacillus subtillis to enhance total activity in aqueous dimethylformarnide." *Protein Eng.* 9(1):77–83.

Youvan et al. *Nature* 401–410 (1992).

Zhao et al. (1996) "Strategy for the directed evolution of a peptide ligase." *Ann NY Acad Sci* 799:1–5.

Zhao et al. (1996) "Functional and nonfunctional mutations distinguished by random recombination of homologous genes." *PNAS USA* 94(15):7997–8000.

Zhao et al. (1997) "Optimization if DNA shuffling for high fidelity recombination." *Nucleic Acids Res.* 25(6):1307–1308.

Statement of Grounds and Particulars In the Matter of Australian Patent Application No. 732,146. Oct. 12, 2001.

European Search Report for Application No. 97953571.3.

European Search Report for Application No. 01202349.5.

European Search Report for Application No. 01202350.3.

Kikuchi et al. (2000) "An effective family shuffling method using single–stranded DNA." *Gene* 243:133–137.

Kishchenko et al. (1997) "Shuffling of structural elements in filamentos bacteriophages." *Proteins* 27(3):405–409.

Kuchner et al. (1997) "Directed evolution of enzyme catalyst." *Trends Biotechnol* 15(12):523–530.

Laffler et al. (1993) "The ligase chain reaction in DNA0baised diagnosis." *Ann Biol Clin* 51(9):821–826.

Lee (1996) "Ligase 5 chain reactio." *Biologicals* 24(3):197–199.

Long et al. (1995) "Intron phase correlations and the evolution of the intron/exon structure of genes." *Proc Natl Acad Sci USA* 92(26):12495–12499.

Matsumura et al. (1996) "DNA shuffling brightens prospects for GFP." *Nat Biotechnol* 14(3):366.

Meijer et al. (1996) "Directed evolution of a type I antifreeze protein expressed in *Escherichia coli* with sodium chloride as selective pressure and its effect on antifreeze tolerance." *Protein Eng.* 9(11):1051–1054.

Miller et al. (1997) "Expanding the 43C9 class of cataytic antibodies using a chain–shuffling approach." *Bioorg Med Chem.* 5(3):581–590.

Moore et al. (1997) "Strategies for the in vitro evolution of protein function: enzyme evolution by random recombination of improved sequences." *J. Mol Biol.* 272(3):336–347.

Moore et al. (1996) "Directed evolution of a para–nitrobenzyl esterase for aqueous–organis solvents." *Nature Biotechnol* 14(4):458–467.

Muller–Dieckmann et al. (1995) "Substrate specificity and assembly of the catalytic center derived from two structures of ligated uridylate kinase." *J. Mol. Biol.* 246(4):522–530.

Nakamura et al. (1996) "Two hydrophobic subunits are essential for the herne b ligation and functional assembly of complex II (succinate–ubiquinone oxidoreductase) from *Eschichia coli.*" *J. Biol Chem* 271(1):521–527.

Nardi et al. (1997) "Duplication of the prpF gene and shuffling of DNA fragments on the lactose plasmid of Lactococcus lactis." *J. Bacteriol* 179(13):4164–4171.

Nelson et al. (1996) "Base eversion and shuffling by DNA Methyltransferases." *Chem Biol* 3(6):419–423.

Ohlin et al. (1996) "Light chain shuffling of a high affinity antibody results in a drift in epitope recognition." *Mol Immunol* 33(1):47–56.

Patten et al. (1997) "applications of DNA shuffling to pharmaceuticals and vaccines." *Curr Opin Biotechnol* 8(6):724–733.

Arnold et al. (1997) "Optimizing industrial enzymes by directed evolution." *Adv. Biochem Eng. Biotechnol* 58:1–14.

Bale et al. (1984) "Kinetics of formation of fibrin oligomers III Ligation kinetics concurrent with and subsequent to oligomer assembly." *Biopolymers* 23(1):127–138.

Barany (1991) "The ligase chain reaction in a PCR world." *PCR Methods Appl.* 1(1):5–16.

Bolli et al (1997) "Pyranosyl–RNA: chiroselective self–assembly of base sequences by ligative oligomerization of tetranucleotide–2', 3'–cyclophosphates (with a commentary concerning the origion of biomolecular homochirality)." *Chem Biol* 4(4):309–320.

Crameri et al. (1993) "Display of biologically active proteins on the surface of filamentous phages: a cDNA cloning system for selection of functional gene products linked to the genetic information responsible for their production." *Gene* 137(1):69–75.

Daughtery et al. (1994) "Bohr effect of the partially–ligated (CN–met) intermediates of hemoglobin as probed by quaternary assembly." *Biochemistry* 33(34):10345–10357.

Doyle et al. (1992) "Cooperative oxygen binding, subunit assembly, and sulfhydryl reaction kenetice of the eight cyanomet intermediate ligation states of human hemoglobin." *Biochemistry* 31(45):11182–11195.

Gaskin et al. (1997) "Directed evolution of a industrially important enzyme." *Biochem Soc Trans* 25(1):155.

Gilbert et al. (1997) "Origion of genes." *PNAS UDS* 94(15):7698–7703.

Giver et al. (1998) "Combinatorial protein design by in ivtro recombination." *Curr Opin Chem Biol.* 2(3):335–338.

Giver et al. (1998) "Directed evolution if a thermostable esterase." *PNAS USA* 95(22):12809–12813.

Graf et al. (1996) *PNAS USA* 11591–11596.

Hurst et al. (1996) "A difficult phase for introns–early Molecular evolution." *Curr Biol* 6(5):533–536.

Kaczorowski et al. (1994) "Assebly of 18–nucleotide primeters by ligation of three hexamers: sequencing of large genomes by primer walking." *Analytical Biochemistry* 221(1):127–135.

Kaczorowski et al. (1996) "Automated four–color DNA sequencing using primers assembled by hexameter ligation." *Gene* 179(1):195–198.

Kalin et al. (1992) "Evaluation of the ligase chain reaction (LCR) for the detection of point mutations." *Mutant Res* 283(2):119–123.

Kato et al. (1996) "Construction of mini–F plasmid vectors for plasmid shuffling in *Escherichia coli.*" *Gene* 170(1):141–142.

Armon et al. (1990) "Assembly of the 26 S complex that degrades protiens ligated to ubiquitin is accompanied by the formation of ATPase activity." *J. Biol Chem* 265(34):20723–207226.

Arnold (1998) "When blind is better: protein designed by evolution." *Nat Biotechnology* 16(7):617–618.

Adey et al. "Preparation of second–generation phage libraries." Proteins 227–291. (1996).

Collet et al. "A binary plasmid system for shuffling combinational antibody libraries." *Proc. Natl. Acad. Sci. USA* 89(21)L10026–10030 (1992).

Dangl et al. "Rapid Isolation of Cloned Isotype Switch Variants Using Fluprescent Activated Cell Sorting." *Cytometry* 2(6):395–401 (1982).

Dierick et al. "Incorporation of dITP of 7–deaza dGTP during PCR improves sequencing of the product." *Nuc. Acid Res.* 21(18):4427–4428 (1993).

Fullen et al. "Genetic Algorithms and Recursive Ensemble Mutagenesis in Protein Engineering." Complex.Inrt.94, from website (1992).

Heda et al. "A simple in vitro site directed mutagenesis of concatamerized cDNA by inverse polymerase chain reaction." *Nuc. Acids Res.* 20(19):5241–5242 (1992).

Hodgson "The Whys and Wherefores of DNA Amplification." *Biotechnology* 11(8):940–942 (1993).

Kang et al. "Antibody redesigned by chain shuffling from ramdom combinatorial immunglobulin libraries." *Proc. Natl. Acad. Sci. USA* 88(24):11120–11123 (1991).

Komano et al. "Distribution of Shufflon among Incl Plasmids." J. Bacteriology 169(11):5317–5319. (1987).

Komano et al. "Physical and Genetic Analysis of Incl2 Plasmid R721: Evidence for the Presence of Shufflon." Plasmid 23:248–251. (1991).

Lownam et al. "Affiniy Maturation of Human Growth Hormone by Monavalent Phage Display." *J. Mol. Biol.* 234:654–578 (1993).

Majumder "Ligation–free gene synthesis by PCR: synthesis and mutagenesis at multiple loci of a chimeric gene encoding OmpA signal peptide and hirudin." *Gene* 110(1):89–94 (1992).

Meryhans et al. "DNA recombination during PCR." *Nuc Acids.Res.* 18(7):1687–1691 (1990).

Olsen et al. "Hybrid Baccillus (1–3,1–4)–β–glucanases: engineering thermostable enzymes by construction of hybrid genes." Mol. Gen. Genet 225(2):–177–185 (1987).

Reikofski & Tao "Polymerase Chain Reaction (PCR) Techniques for Site–directed Mutagenesis." *Biotech Adv.* 10:535–547 (1992).

Robles et al. "Hydorpathy and Molar Volume Constraints on Combinatorial Mutants of the Photosynthetic Reaction Center." J.Mol.Biol., 232:242–252 (1993).

Stemmer et al. "A 20–Minute Ethidium Bromide High–slat Extraction Protocol for Pasmid DNA." Biotechniques 10(6):726 (1991).

Stemmer et al. "Enzymatic Inverse PCR–A Restriction Cite Independent, Single–Fragment Method for High–Efficiency, Site–Directed Mutagenesis." Biotechniques 13(2):214. (1992).

Stemmer et al. (1991) R342 "Expression of Antibody By Fragments Specific for a Heavy Metal Chelate (indium EDTA) in *E–coli.*" J. Cell Biochem. 217.

Stemmer et al. "Increased Antibody Expression for *Escherichia–Coli* Through Wobble–Base Library Mutagenesis by Enzymatic Inverse PCR." Gene 123(1):1–7. (1993).

Wu et al. "Allale–specific enzymatic amplificaiton of β–globin genomis DNA for diagnosis of sickle cell anema." Proc. Natl. Acad. Sci vol. 86:2757–2760 (1999).

* cited by examiner

Interferon Figures

Protein sequences of interferon alphas to be shuffled

```
1.Consensus   C D L P Q T H S L G N R R A L I L L A Q M G R I S P F S C L
              *   * *       *         * * *   *       *         * *
                          10          20          30
 2. alpha I   - - - - - - - - - - - - - - - - - - - - - - - - - - - - -
 3. alpha C   - - - - - - - - - - - - - - - - - - - - - - - - - - - - -
 4. alpha H   - N - S - - - - - N - - - T - M - - - - - R - - - - - - -
 5. alpha 4B  - - - - - - - - - - - - - - - - - - - - - - - - - H - - -
 6. alpha 6   - - - - - - - - - H - - T M M - - - - - R - - - L - - - -
 7. alpha 7   - - - - - - - - - R - - - - - - - - - - - - - - - - - - -
 8. alpha 8   - - - - - - - - - - - - - - - - - - - - R - - - - - - - -
 9. alpha D   - - - - E - - - - D - - - T - M - - - - - S - - - - S - - -
10. alpha F   - - - - - - - - - - - - - - - - - - - - - - - - - - - - -
11. alpha I   - - - - - - - - - - - - - - - - - - - - - - - - - - - - -
12. alpha WA  - - - - - - - - - - - - - - - - - - - - - - - - - H - - -

1.Consensus   K D R H D F G F P Q E E F D G N Q F Q K A Q A I S V L H E M
              *       *   * *   *   *   * *   *     * *     * * *     *
                          40          50          60
 2. alpha I   - - - - - - - - L - - - - - - - - - - - T - - - P - - - - -
 3. alpha C   - - - P - - - - L - - - - - - - - - - - T - - - - - - - - -
 4. alpha H   - - - - - - - E - - - - - - - - - - - - - - - - - - - - -
 5. alpha 4B  - - - - - - - - - E - - - - H - - - - T - - - - - - - - -
 6. alpha 6   - - - - - R - - - - - - - - - - - - - - - E - - - - - - - V
 7. alpha 7   - - - - E - R - - E - - - - H - - - T - - - - - - - - - -
 8. alpha 8   - - - - - E - - - - - - - D K - - - - - - - - - - - - - -
 9. alpha D   M - - - - - - - - - - - - - - - - - - - P - - - - - - - L
10. alpha F   - - - - - - - - - - - - - - - - - - - - - - - - - - - - -
11. alpha I   - - - P - - - - L - - - - - - - - - - - T - - - - - - - - -
12. alpha WA  - - - Y - - - - - - - - - V - - - - - - - - - - A F - - -

1.Consensus   I Q Q T F N L F S T K D S S A A W E Q S L L E K F S T E L Y
              *   *   *     * *   * *   * * * * *     * * * * *       *
                          70          80          90
 2. alpha I   - - - - - - - - - - E - - - - - - - - - - - - - - - - - -
 3. alpha C   - - - - - - - - - - E - - - - - - - - - - - - - - - - - -
 4. alpha H   M - - - - - - - - - - N - - - - D E T - - - - - Y I - - F
 5. alpha 4B  - - - - - - - - - - E - - - - - - - - - - - - - - - - - -
 6. alpha 6   - - - - - - - - - - - - - - V - - D E R - - D - L Y - - - -
 7. alpha 7   - - - - - - - - - - E - - - - - - - - - - - - - - - - - -
 8. alpha 8   - - - - - - - - - - - - - - - - L D E T - - D E - Y I - - D
 9. alpha D   - - - I - - - - T - - - - - - - D E D - - D - - C - - - -
10. alpha F   - - - - - - - - - - - - - - - - T - - - - - - - - - - - N
11. alpha I   - - - - - - - - - - E - - - - - - - - - - - - - - - - - -
12. alpha WA  - - - - - - - - - - - - - - - - D E T - - D - - Y I - - F 1.Consensus   Q Q L N D L E A C V I Q E V G V E E T P L M N E D S I L A V
              *   * *   *   * *   * * *   * * *   * * *     * *   *
                         100         110         120
 2. alpha I   - - - - N - - - - - - Q - - - M - - - - - - - - - - - - -
 3. alpha C   - - - - N - - - - - - - - - - M - - - - - - - - - - - - -
 4. alpha H   - - M - - - - - - - - - - - - - - - - - - - - - - - - - -
 5. alpha 4B  - - - - - - - - - - - - - - - - - - - - - - - - V - - - -
 6. alpha 6   - - - - - - - - - M - - W - G G - - - - - - - - - - - -
 7. alpha 7   - - - - - - - - - - - - - - - - - - - - - - - - - F - - -
 8. alpha 8   - - - - - - - S - - M - - - - - I - S - - - Y - - - - - -
 9. alpha D   - - - - - - - - - M - - E R - G - - - - - A - - - - - -
10. alpha F   - - - - M - - - - - - - - - - - - - - - - V - - - - - - -
11. alpha I   - - - - N - - - - - - - - - - M - - - - - - - - - - - - -
12. alpha WA  - - - - - - - - T - - - - - - - I A - - - - - - - - - - - -
```

Figure 2A

```
1.Consensus   R K Y F Q R I T L Y L T E K K Y S P C A W E V V R A E I M R
              *   *       *           * *     *
                          130           140         150
 2. alpha I   - - - - - - - - - - - - - - - - - - - - - - - - - - - - -
 3. alpha C   - - - - - - - - - - - - - - - - - - - - - - - - - - - - -
 4. alpha H   K - - - - - - - - - - M - - - - - - - - - - - - - - - - -
 5. alpha 4B  - - - - - - - - - - - - - - - - - - - - - - - - - - - - -
 6. alpha 6   - - - - - - - - - - - - - - - - - - - - - - - - - - - - -
 7. alpha 7   - - - - - - - - - - - - M - - - - - - - - - - - - - - - -
 8. alpha 8   - - - - - - - - - - - - - - - - - S - - - - - - - - - - -
 9. alpha D   K - - - R - - - - - - - - - - - - - - - - - - - - - - - -
10. alpha F   K - - - - - - - - - - - - - - - - - - - - - - - - - - - -
11. alpha I   - - - - - - - - - - - - - - - - - - - - - - - - - - - - -
12. alpha WA  - - - - - - - - - - M G - - - - - - - - - - - - - - - - -

1.Consensus   S L S F S T N L Q K R L R R K D    SEQ ID NO: 75
              *   *   * * * * * *   * *
                          160
 2. alpha I   - - - - - - - - - - - - - - - -    SEQ ID NO: 76
 3. alpha C   - - - - - - - - - - I - - - - -    SEQ ID NO: 77
 4. alpha H   - - - - - - - - - - - - - - - -    SEQ ID NO: 78
 5. alpha 4B  - - - - - - - - - - - - - - - -    SEQ ID NO: 79
 6. alpha 6   - P - S - R - - - E - - - - - E    SEQ ID NO: 80
 7. alpha 7   - F - - - - - - K - G - - - - -    SEQ ID NO: 81
 8. alpha 8   - F - L - I - - - - - - K S - E    SEQ ID NO: 82
 9. alpha D   - - - L - - - - - E - - - - - E    SEQ ID NO: 83
10. alpha F   - F - L - K I F - E - - - - - E    SEQ ID NO: 84
11. alpha I   - - - - - - - - - - I - - - - -    SEQ ID NO: 85
12. alpha WA  - F - - - - - - - G - - - - - -    SEQ ID NO: 86
```

Figure 2B

DNA sequences of interferon alphas to be shuffled

```
1.Consensus    T G T G A T C T G C C T C A G A C C C A C A G C C T G G G T 10          20          30
2. alpha I     - - - - - - - - - - - - - - - - - - - - - - - - - - - - - -
3. alpha C     - - - - - - - - - - - - - - - - - - - - - - - - - - - - - -
4. alpha H     - - - A - - - - - T - - - - A - - - - - - - - - - - - A A -
5. alpha 4B    - - - - - - - - - - - - - - - - - - - - - - - - - - - - - -
6. alpha 6     - - - - - - - - - - - - - - - - - - - - - - - - - - - - - -
7. alpha 7     - - - - - - - - - - - - - - - - - - - - - - - - - - - C - -
8. alpha 8     - - - - - - - - - - - - - - - - - T - - - - - - - - - - - -
9. alpha D     - - - - - - - - C - - - G - - - - - - - - - - - - - - - A -
10.alpha F     - - - - - - - - - - - - - - - - - - - - - - - - - - - - - -
11.alpha I     - - - - - - - - - - - - - - - - - - - - - - - - - - - - - -
12.alpha WA    - - - - - - - - - - - - - - - - - T - - - - - - - - - - - -

1.Consensus    A A T A G G A G G G C C T T G A T A C T C C T G G C A C A A 40          50          60
2. alpha I     - - - - - - - - - - - - - - - - - - - - - - - - - - - - - -
3. alpha C     - - - - - - - - - - - - - - - - - - - - - - - - - - - - - -
4. alpha H     - - C - - - - - - A - T - - - - - G - - - A - - - - - - - -
5. alpha 4B    - - - - - - - - - - - - - - - - - - - - - - - - - - - - - -
6. alpha 6     C - C - - - - - - A - - A - - - - G - - - - - - - - - - - -
7. alpha 7     - - - - - - - - - - - - - - - - - - - - - - - - - - - - - -
8. alpha 8     - - C - - - - - - - - - - - - - - - - - - - - - - - - - - -
9. alpha D     - - C - - - - - - A - - - - - - - G - - - - - - - - - - - -
10.alpha F     - - - - - - - - - - - - - - - - - - - - - - - - - - - - - -
11.alpha I     - - - - - - - - - - - - - - - - - - - - - - - - - - - - - -
12.alpha WA    - - - - - - - - - - - - - - - - - - - - - - - - - - - - - -

1.Consensus    A T G G G A A G A A T C T C T C C T T T C T C C T G C C T G 70          80          90
2. alpha I     - - - - - - - - - - - - - - - - - - - - - - - - - - - - - -
3. alpha C     - - - - - - - - - - - - - - - - - - - - - - - - - - - - - -
4. alpha H     - - - A - G - - - - - - - - - - - - - - - - - - - - - - - -
5. alpha 4B    - - - - - - - - - - - - - - - - A - - - - - - - - - - - - -
6. alpha 6     - - - A - G - - - - - - - - - - T - - - - - - - - - T - - -
7. alpha 7     - - - - - - - - - - - - - - - - - - - - - - - - - - - T - -
8. alpha 8     - - - C - - - - - - - - - - - - - - - - - - - - - - - - - -
9. alpha D     - - - A - C - - - - - - - - - - - - - C - - - - - - T - - -
10.alpha F     - - - - - - - - - - - - - - - - - - - - - - - - - - - - - -
11.alpha I     - - - - - - - - - - - - - - - - - - - - - - - - - - - - - -
12.alpha WA    - - - - - - - - - - - - - - - - A - - - - - - - - - - - - -

1.Consensus    A A G G A C A G A C A T G A C T T T G G A T T T C C C C A G 100         110         120
2. alpha I     - - - - - - - - - - - - - - - - - - - - - C - - - - - - - -
3. alpha C     - - - - - - - - - - C - - - - - - - - - - C - - - - - - - -
4. alpha H     - - - - - - - - - - - - - - - - - - - A - - - - - - - - - -
5. alpha 4B    - - - - - - - - - - - - - - T - - C - - - - - C - - - G - -
6. alpha 6     - - - - - - - - - - - - - - - - - C A - - - - - - - - - - -
7. alpha 7     - - - - - - - - - - - - - - A - - C A - - - - C - - A G - -
8. alpha 8     - - - - - - - - - - - - - - - - - - - A - - - C - - - - - -
9. alpha D     - T - - - - - - - - - - - - - - - - - - - - - - - - - - - -
10.alpha F     - - - - - - - - - - - - - - - - - - - - - - - C - - - - - A
11.alpha I     - - - - - - - - - - C - - - - - - - - - - C - - - - - - - -
12.alpha WA    - - - - - - - - - T - - - - T - - C - - - - - C - - - - - -
```

Figure 2C

```
1.Consensus    G A G G A G T T T G A T G G C A A C C A G T T C C A G A A G
                                 130         140         150
 2. alpha I    - - - - - - - - - - - - - - - - - - - - - - - - - - - - -
 3. alpha C    - - - - - - - - - - - - - - - - - - - - - - - - - - - - -
 4. alpha H    - - - - - A - - - - - - - - - - - - - - - - - - - - - - A
 5. alpha 4B   - - - - - - - - - - - - - C - - - - - - - - - - - - - - -
 6. alpha 6    - - - - - - - - - - - - - - - - - - - - - - - - - - - - -
 7. alpha 7    - - - - - - - - - - - - - C - - C - - - - - - - - - - - -
 8. alpha 8    - - - - - - - - - - - - A T - - A - - - - - - - - - - - -
 9. alpha D    - - - - - - - - - - - - - - - - - - - - - - - - - - - - -
10. alpha F    - - - - - - - - - - - - - - - - - - - - - - - - - - - - -
11. alpha I    - - - - - - - - - - - - - - - - - - - - - - - - - - - - -
12. alpha WA   - - - - T - - - - - - - - - - - - - - - - - - - - - - - -

1.Consensus    G C T C A A G C C A T C T C T G T C C T C C A T G A G A T G
                                 160         170         180
 2. alpha I    A - - - - - - - - - - - - - - - C - - - - - - - - - - - -
 3. alpha C    A - - - - - - - - - - - - - - - - - - - - - - - - - - - -
 4. alpha H    - - - - - - - - - - - - - - - - - - - - - - - - - - - - -
 5. alpha 4B   A - - - - - - - - - - - - - - - - - - - - - - - - - - - -
 6. alpha 6    - - - G - - - - - - - - - - - - - - - - - - - - - - G - -
 7. alpha 7    A - - - - - - - - - - - - - - - - - - - - - - - - - - - -
 8. alpha 8    - - - - - - - - - - - - - - - - - - - - - - - - - - - - -
 9. alpha D    - - - - C - - - - - - - - - - - - - - - - - - - - - C - -
10. alpha F    - - - - - - - - - - - - - - - - - - - - - - - - - - - - -
11. alpha I    A - - - - - - - - - - - - - - - - - - - - - - - - - - - -
12. alpha WA   - - - - - - - - - - - - - - - C - T - - - - - - - - - - -

1.Consensus    A T C C A G C A G A C C T T C A A T C T C T T C A G C A C A
                                 190         200         210
 2. alpha I    - - - - - - - - - - - - - - - - - - - - - - - - - - - - -
 3. alpha C    - - - - - - - - - - - - - - - - - - - - - - - - - - - - -
 4. alpha H    - - G - - - - - - - - - - - - - - - - - - - - - - - - - -
 5. alpha 4B   - - - - - - - - - - - - - - - - - - - - - - - - - - - - -
 6. alpha 6    - - T - - - - - - - - - - - - - - - - - - - - - - - - - -
 7. alpha 7    - - - - - - - - - - - - - - - - - - - - - - - - - - - - -
 8. alpha 8    - - - - - - - - - - - - - - - - - - - C - - - - - - - - -
 9. alpha D    - - - - - - - - - T - - - - - - C - - - - - T C - - - -
10. alpha F    - - - - - - - - - - - - - - - - - - - - - - - - - - - - -
11. alpha I    - - - - - - - - - - - - - - - - - - - - - - - - - - - - -
12. alpha WA   - - - - - - - - - - - - - - - - - - - - - - - - - - - - -

1.Consensus    A A G G A C T C A T C T G C T G C T T G G G A T G A G A G C
                                 220         230         240
 2. alpha I    G - - - - - - - - - - - - - - - - - - - - - A C - - - - -
 3. alpha C    G - - - - - - - - - - - - - - - - - - - - - A C - - - - -
 4. alpha H    - - - A - - - - - - - - - - - - - - - - - - - - - - - C -
 5. alpha 4B   G - - - - - - - - - - - - - - - - - - - - - A C - - - - -
 6. alpha 6    - - - - - - - - - - - - T - - - - - - - - - - - - - - - G
 7. alpha 7    G - - - - - - - - - - - - - - - - - - - - - A C - - - - -
 8. alpha 8    - - - - - - - - - - - - - T - - - - - - - - - - - - - C -
 9. alpha D    - - A - - T - - - - - - - - - - - - - - - - - - - - G A -
10. alpha F    - - - - - - - - - - - - - - - A - - - - - - A C - - - - -
11. alpha I    G - - - - - - - - - - - - - - - - - - - - - A C - - - - -
12. alpha WA   - - - - T - - - - - - - - - - - - - - - - - - - - - - C -
```

Figure 2D

```
1.Consensus    C T C C T A G A A A A A T T T T C C A C T G A A C T T T A C
                              250           260           270
 2. alpha I    - - - - - - - - - - - - - - - - - - - - - - - - - - - - - -
 3. alpha C    - - - - - - - - - - - - - - - - - - - - - - - - - - - - - -
 4. alpha H    - - - - - - - - - - - - - C - A - - T - - - - - - - - T -
 5. alpha 4B   - - - - - - - - - - - - - - - - - - - - - - - - - - - - - -
 6. alpha 6    - - T - - - - - C - - - C - C - A T - - - - - - - - - - - -
 7. alpha 7    - - - - - - - - - - - - - - - - - - - - - - - - - - - - - -
 8. alpha 8    - - T - - - - - T G - - - - C - A - - T C - - - - - - G - -
 9. alpha D    - - - - - - - - C - - - - - C - G - - - C - - - - - C - - -
10. alpha F    - - - - - - - - - - - - - - - - - - - - - - - - - A - -
11. alpha I    - - - - - - - - - - - - - - - - - - - - - - - - - - - - - -
12. alpha WA   - - - - - - - C - - - - - C - A - - T - - - - - - - - T -

1.Consensus    C A G C A A C T G A A T G A C C T G G A A G C C T G T G T G
                              280           290           300
 2. alpha I    - - - - - - - - - - - - - A - - - - - - - - - A - - - - - -
 3. alpha C    - - - - - - - - - - - - - A - - - - - - - - - A - - - - - -
 4. alpha H    - - - - - A - - - - - - - - - - - - - - - - - - - - - - - -
 5. alpha 4B   - - - - - - - - - - - - - - - - - - - - - - - A - - - - - -
 6. alpha 6    - - - - - G - - - - - - - - - - - - - - - - - - - - - - - -
 7. alpha 7    - - - - - - - - - - - - - - - - - - - - - - - A - - - - - -
 8. alpha 8    - - - - - G - - - - - - - - - - - - - - - - G T - - - - - -
 9. alpha D    - - - - - G - - - - - - T - - - - - - - - - - - - - - - - -
10. alpha F    - - - - - G - - - - - - A - - - - - - - - - - - C - - -
11. alpha I    - - - - - - - - - - - - - A - - - - - - - - - A - - - - - -
12. alpha WA   - - - - - - - - - - - - - - - A - - - - - - - - - - - - - -

1.Consensus    A T A C A G G A G G T T G G G G T G G A A G A G A C T C C C
                              310           320           330
 2. alpha I    - - - G - - - - - - - - - - - A - - - - - - - - - - -
 3. alpha C    - - - - - - - - - - - - - - - A - - - - - - - - - - -
 4. alpha H    - - - - - - - - - - - - - - - - - - - - - - - - - - - - - -
 5. alpha 4B   - - - - - - - - - - - - - - - - - - - - - - - - - - - - - -
 6. alpha 6    - - G - - - - - - - G T - - - - - - G - - G - - - - -
 7. alpha 7    - - - - - - - - - - - - - - - - - - - - - - - - - - - - - -
 8. alpha 8    - - G - - - - - A - - G - - - - - A T - - - T - - - -
 9. alpha D    - - G - - - - - A G A - - - - - G - - - A - - - - - -
10. alpha F    - - - - - - - - - - - - - - - - - - - - - - - - - - - - - -
11. alpha I    - - - - - - - - - - - - - A - - - - - - - - - - - - - - - -
12. alpha WA   - C - - - - - - - - - - - - - - - - - - - - - T - G - -

1.Consensus    C T G A T G A A T G A G G A C T C C A T C C T G G C T G T G
                              340           350           360
 2. alpha I    - - - - - - - - - - - - - - - - - - - - - - - - - - - - - -
 3. alpha C    - - - - - - - - - - - - - - - - - - - - - - - - - - - - - -
 4. alpha H    - - - - - - - - - - - - - - - - - - - - - - - - - - - - - -
 5. alpha 4B   - - - - - - - - - T - - - - - - - - - - - - - - - - - - - -
 6. alpha 6    - - - - - - - - - - - - - - - - - - - - - - - - - - - - - -
 7. alpha 7    - - - - - - - - - - - - - - - - - - - - - - - - - - - - - -
 8. alpha 8    - - - - - - - - - - - - - T - - - - - - - - - - - - - - - -
 9. alpha D    - - - - - - - T - C - C - - - - - - - - - - - - - - - - - -
10. alpha F    - - - - - - - - - T - - - - - - T - - - - - - - -
11. alpha I    - - - - - - - - - - - - - - - - - T - - - - - - - - - - - -
12. alpha WA   - - - - - - - - - - - - - - - - - - - - - - - - - - - - - -
```

```
1.Consensus   A G A T T A A G G A G G A A G G A T T G A    SEQ ID NO: 87
                              490         500
 2. alpha I   - - - - - - - - - - - - - - - - - - - - -    SEQ ID NO: 88
 3. alpha C   - T - - - - - - - - - - - - - - - - - - -    SEQ ID NO: 89
 4. alpha H   - - - - - - - - - - - - - - - - - - - - -    SEQ ID NO: 90
 5. alpha 4B  - - - - - - - - - - - - - - - - - - - - -    SEQ ID NO: 91
 6. alpha 6   - - G - - - - - - - O - - - - A - A - - -    SEQ ID NO: 92
 7. alpha 7   G - - - - - - - - - - - - - - - - - - - -    SEQ ID NO: 93
 8. alpha 8   - - - - - G - A - - - T - - - - A - - - -    SEQ ID NO: 94
 9. alpha D   - - - - - - - - - - - - - - - - A - A - -    SEQ ID NO: 95
10. alpha F   - - - - - - - - - - - - - - - - A - - - -    SEQ ID NO: 96
11. alpha I   - - - - - - - - - - - - - - - - - - - - -    SEQ ID NO: 97
12. alpha WA  G - - - - - - A - - - - - - - - - - - - -    SEQ ID NO: 98
```

METHODS AND COMPOSITIONS FOR POLYPEPTIDE ENGINEERING

This application is a continuation of, and claims priority to and the benefit of, U.S. application Ser. No. 08/769,062, filed Dec. 18, 1996, now U.S. Pat. No. 6,335,160 which is incorporated by reference in its entirety for all purposes.

COPYRIGHT NOTIFICATION

Pursuant to 37 C.F.R. § 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

Recursive sequence recombination entails performing iterative cycles of recombination and screening or selection to "evolve" individual genes, whole plasmids or viruses, multigene clusters, or even whole genomes (Stemmer, *Bio/Technology* 13:549–553 (1995)). Such techniques do not require the extensive analysis and computation required by conventional methods for polypeptide engineering. Recursive sequence recombination allows the recombination of large numbers of mutations in a minimum number of selection cycles, in contrast to traditional, pairwise recombination events.

Thus, recursive sequence recombination (RSR) techniques provide particular advantages in that they provide recombination between mutations in any or all of these, thereby providing a very fast way of exploring the manner in which different combinations of mutations can affect a desired result.

In some instances, however, structural and/or functional information is available which, although not required for recursive sequence recombination, provides opportunities for modification of the technique. In other instances, selection and/or screening of a large number of recombinants can be costly or time-consuming. A further problem can be the manipulation of large nucleic acid molecules. The instant invention addresses these issues and others.

SUMMARY OF THE INVENTION

One aspect of the invention is a method for evolving a protein encoded by a DNA substrate molecule comprising:
  (a) digesting at least a first and second DNA substrate molecule, wherein the at least a first and second substrate molecules differ from each other in at least one nucleotide, with a restriction endonuclease;
  (b) ligating the mixture to generate a library of recombinant DNA molecules;
  (c) screening or selecting the products of (b) for a desired property; and
  (d) recovering a recombinant DNA substrate molecule encoding an evolved protein.

A further aspect of the invention is a method for evolving a protein encoded by a DNA substrate molecule by recombining at least a first and second DNA substrate molecule, wherein the at least a first and second substrate molecules differ from each other in at least one nucleotide and comprise defined segments, the method comprising:
  (a) providing a set of oligonucleotide PCR primers, comprising at least one primer for each segment, wherein the primer sequence is complementary to at least one junction with another segment;
  (b) amplifying the segments of the at least a first and second DNA substrate molecules with the primers of step (a) in a polymerase chain reaction;
  (c) assembling the products of step (b) to generate a library of recombinant DNA substrate molecules;
  (d) screening or selecting the products of (c) for a desired property; and
  (e) recovering a recombinant DNA substrate molecule from (d) encoding an evolved protein.

A further aspect of the invention is a method of enriching a population of DNA fragments for mutant sequences comprising:
  (a) denaturing and renaturing the population of fragments to generate a population of hybrid double-stranded fragments in which at least one double-stranded fragment comprises at least one base pair mismatch;
  (b) fragmenting the products of (a) into fragments of about 20–100 bp;
  (c) affinity-purifying fragments having a mismatch on an affinity matrix to generate a pool of DNA fragments enriched for mutant sequences; and
  (d) assembling the products of (c) to generate a library of recombinant DNA substrate molecules.

A further aspect of the invention is a method for evolving a protein encoded by a DNA substrate molecule, by recombining at least a first and second DNA substrate molecule, wherein the at least a first and second substrate molecules share a region of sequence homology of about 10 to 100 base pairs and comprise defined segments, the method comprising:
  (a) providing regions of homology in the at least a first and second DNA substrate molecules by inserting an intron sequence between at least two defined segments;
  (b) fragmenting and recombining DNA substrate molecules of (a), wherein regions of homology are provided by the introns;
  (c) screening or selecting the products of (b) for a desired property; and
  (d) recovering a recombinant DNA substrate molecule from the products of (c) encoding an evolved protein.

A further aspect of the invention is a method for evolving a protein encoded by a DNA substrate molecule by recombining at least a first and second DNA substrate molecule, wherein the at least a first and second substrate molecules differ from each other in at least one nucleotide and comprise defined segments, the method comprising:
  (a) providing a set of oligonucleotide PCR primers, wherein for each strand of each segment a pair of primers is provided, one member of each pair bridging the junction at one end of the segment and the other bridging the junction at the other end of the segment, with the terminal ends of the DNA molecule having as one member of the pair a generic primer, and wherein a set of primers is provided for each of the at least a first and second substrate molecules;
  (b) amplifying the segments of the at least a first and second DNA substrate molecules with the primers of (a) in a polymerase chain reaction;
  (c) assembling the products of (b) to generate a pool of recombinant DNA molecules;
  (d) selecting or screening the products of (c) for a desired property; and (e) recovering a recombinant DNA substrate molecule from the products of (d) encoding an evolved protein.

A further aspect of the invention is a method for optimizing expression of a protein by evolving the protein, wherein the protein is encoded by a DNA substrate molecule, comprising:
- (a) providing a set of oligonucleotides, wherein each oligonucleotide comprises at least two regions complementary to the DNA molecule and at least one degenerate region, each degenerate region encoding a region of an amino acid sequence of the protein;
- (b) assembling the set of oligonucleotides into a library of full length genes;
- (c) expressing the products of (b) in a host cell;
- (d) screening the products of (c) for improved expression of the protein; and
- (e) recovering a recombinant DNA substrate molecule encoding an evolved protein from (d).

A further aspect of the invention is a method for optimizing expression of a protein encoded by a DNA substrate molecule by evolving the protein, wherein the DNA substrate molecule comprises at least one lac operator and a fusion of a DNA sequence encoding the protein with a DNA sequence encoding a lac headpiece dimer, the method comprising:
- (a) transforming a host cell with a library of mutagenized DNA substrate molecules;
- (b) inducing expression of the protein encoded by the library of (a);
- (c) preparing an extract of the product of (b);
- (d) fractionating insoluble protein from complexes of soluble protein and DNA; and
- (e) recovering a DNA substrate molecule encoding an evolved protein from (d).

A further aspect of the invention is a method for evolving functional expression of a protein encoded by a DNA substrate molecule comprising a fusion of a DNA sequence encoding the protein with a DNA sequence encoding filamentous phage protein to generate a fusion protein, the method comprising:
- (a) providing a host cell producing infectious particles expressing a fusion protein encoded by a library of mutagenized DNA substrate molecules;
- (b) recovering from (a) infectious particles displaying the fusion protein;
- (c) affinity purifying particles displaying the mutant protein using a ligand for the protein; and
- (d) recovering a DNA substrate molecule encoding an evolved protein from affinity purified particles of (c).

A further aspect of the invention is a method for optimizing expression of a protein encoded by a DNA substrate molecule comprising a fusion of a DNA sequence encoding the protein with a lac headpiece dimer, wherein the DNA substrate molecule is present on a first plasmid vector, the method comprising:
- (a) providing a host cell transformed with the first vector and a second vector comprising a library of mutants of at least one chaperonin gene, and at least one lac operator;
- (b) preparing an extract of the product of (a);
- (c) fractionating insoluble protein from complexes of soluble protein and DNA; and
- (d) recovering DNA encoding a chaperonin gene from (c).

A further aspect of the invention is a method for optimizing expression of a protein encoded by a DNA substrate molecule comprising a fusion of a DNA sequence encoding the protein with a filamentous phage gene, wherein the fusion is carried on a phagemid comprising a library of chaperonin gene mutants, the method comprising:
- (a) providing a host cell producing infectious particles expressing a fusion protein encoded by a library of mutagenized DNA substrate molecules;
- (b) recovering from (a) infectious particles displaying the fusion protein;
- (c) affinity purifying particles displaying the protein using a ligand for the protein; and
- (d) recovering DNA encoding the mutant chaperonin from affinity purified particles of (c).

A further aspect of the invention is a method for optimizing secretion of a protein in a host by evolving a gene encoding a secretory function, comprising:
- (a) providing a cluster of genes encoding secretory functions;
- (b) recombining at least a first and second sequence in the gene cluster of (a) encoding a secretory function, the at least a first and second sequences differing from each other in at least one nucleotide, to generate a library of recombinant sequences;
- (c) transforming a host cell culture with the products of (b), wherein the host cell comprises a DNA sequence encoding the protein;
- (d) subjecting the product of (c) to screening or selection for secretion of the protein; and
- (e) recovering DNA encoding an evolved gene encoding a secretory function from the product of (d).

A further aspect of the invention is a method for evolving an improved DNA polymerase comprising:
- (a) providing a library of mutant DNA substrate molecules encoding mutant DNA polymerase;
- (b) screening extracts of cells transfected with (a) and comparing activity with wild type DNA polymerase;
- (c) recovering mutant DNA substrate molecules from cells in (b) expressing mutant DNA polymerase having improved activity over wild-type DNA polymerase; and
- (d) recovering a DNA substrate molecule encoding an evolved polymerase from the products of (c).

A further aspect of the invention is a method for evolving a DNA polymerase with an error rate greater than that of wild type DNA polymerase comprising:
- (a) providing a library of mutant DNA substrate molecules encoding mutant DNA polymerase in a host cell comprising an indicator gene having a revertible mutation, wherein the indicator gene is replicated by the mutant DNA polymerase;
- (b) screening the products of (a) for revertants of the indicator gene;
- (c) recovering mutant DNA substrate molecules from revertants; and
- (d) recovering a DNA substrate molecule encoding an evolved polymerase from the products of (c).

A further aspect of the invention is a method for evolving a DNA polymerase, comprising:
- (a) providing a library of mutant DNA substrate molecules encoding mutant DNA polymerase, the library comprising a plasmid vector;
- (b) preparing plasmid preparations and extracts of host cells transfected with the products of (a);
- (c) amplifying each plasmid preparation in a PCR reaction using the mutant polymerase encoded by that plasmid, the polymerase being present in the host cell extract;

(d) recovering the PCR products of (c); and (e) recovering a DNA substrate molecule encoding an evolved polymerase from the products of (d).

A further aspect of the invention is a method for evolving a p-nitrophenol phosphonatase from a phosphonatase encoded by a DNA substrate molecule, comprising:

(a) providing library of mutants of the DNA substrate molecule, the library comprising a plasmid expression vector;

(b) transfecting a host, wherein the host phn operon is deleted;

(c) selecting for growth of the transfectants of (b) using a p-nitrophenol phosphonatase as a substrate;

(d) recovering the DNA substrate molecules from transfectants selected from (c); and (e) recovering a DNA substrate molecule from (d) encoding an evolved phosphonatase.

A further aspect of the invention is a method for evolving a protease encoded by a DNA substrate molecule comprising:

(a) providing library of mutants of the DNA substrate molecule, the library comprising a plasmid expression vector, wherein the DNA substrate molecule is linked to a secretory leader;

(b) transfecting a host;

(c) selecting for growth of the transfectants of (b) on a complex protein medium; and (d) recovering a DNA substrate molecule from (c) encoding an evolved protease.

A further aspect of the invention is a method for screening a library of protease mutants displayed on a phage to obtain an improved protease, wherein a DNA substrate molecule encoding the protease is fused to DNA encoding a filamentous phage protein to generate a fusion protein, comprising:

(a) providing host cells expressing the fusion protein;

(b) overlaying host cells with a protein net to entrap the phage;

(c) washing the product of (b) to recover phage liberated by digestion of the protein net;

(d) recovering DNA from the product of (c); and (e) recovering a DNA substrate from (d) encoding an improved protease.

A further aspect of the invention is a method for screening a library of protease mutants to obtain an improved protease, the method comprising:

(a) providing a library of peptide substrates, the peptide substrate comprising a fluorophore and a fluorescence quencher;

(b) screening the library of protease mutants for ability to cleave the peptide substrates, wherein fluorescence is measured; and (c) recovering DNA encoding at least one protease mutant from (b) A further aspect of the invention is a method for evolving an alpha interferon gene comprising:

(a) providing a library of mutant alpha interferon genes, the library comprising a filamentous phage vector;

(b) stimulating cells comprising a reporter construct, the reporter construct comprising a reporter gene under control of an interferon responsive promoter, and wherein the reporter gene is GFP;

(c) separating the cells expressing GFP by FACS;

(d) recovering phage from the product of (c); and (e) recovering an evolved interferon gene from the product of (d).

A further aspect of the invention is a method for screening a library of mutants of a DNA substrate encoding a protein for an evolved DNA substrate, comprising:

(a) providing a library of mutants, the library comprising an expression vector;

(b) transfecting a mammalian host cell with the library of (a), wherein mutant protein is expressed on the surface of the cell;

(c) screening or selecting the products of (b) with a ligand for the protein;

(d) recovering DNA encoding mutant protein from the products of (c); and (e) recovering an evolved DNA substrate from the products of (d).

A further aspect of the invention is a method for evolving a DNA substrate molecule encoding an interferon alpha, comprising:

(a) providing a library of mutant alpha interferon genes, the library comprising an expression vector wherein the alpha interferon genes are expressed under the control of an inducible promoter;

(b) transfecting host cells with the library of (a);

(c) contacting the product of (b) with a virus;

(d) recovering DNA encoding a mutant alpha interferon from host cells surviving step (c); and (e) recovering an evolved interferon gene from the product of (d).

A further aspect of the invention is a method for evolving the stability of a protein encoded by a DNA substrate molecule, the DNA substrate molecule comprising a fusion of a DNA sequence encoding the protein with a DNA sequence encoding a filamentous phage protein to generate a fusion protein, the method comprising:

(a) providing a host cell expressing a library of mutants of the fusion protein;

(b) affinity purifying the mutants with a ligand for the protein, wherein the ligand is a human serum protein, tissue specific protein, or receptor;

(c) recovering DNA encoding a mutant protein from the affinity selected mutants of (b); and (d) recovering an evolved gene encoding the protein from the product of (c).

A further aspect of the invention is a method for evolving a protein having at least two subunits, comprising:

(a) providing a library of mutant DNA substrate molecules for each subunit;

(b) recombining the libraries into a library of single chain constructs of the protein, the single chain construct comprising a DNA substrate molecule encoding each subunit sequence, the subunit sequence being linked by a linker at a nucleic acid sequence encoding the amino terminus of one subunit to a nucleic acid sequence encoding the carboxy terminus of a second subunit;

(c) screening or selecting the products of (B), (d) recovering recombinant single chain construct DNA substrate molecules from the products of (c);

(e) subjecting the products of (d) to mutagenesis; and (f) recovering an evolved single chain construct DNA substrate molecule from (e).

A further aspect of the invention is a method for evolving the coupling of a mammalian 7-transmembrane receptor to a yeast signal transduction pathway, comprising:

(a) expressing a library of mammalian G alpha protein mutants in a host cell, wherein the host cell expresses the mammalian 7-transmembrane receptor and a reporter gene, the receptor gene geing expressed under control of a pheromone responsive promoter;

(b) screening or selecting the products of (a) for expression of the reporter gene in the presence of a ligand for the 7-transmembrance receptor; and (c) recovering DNA encoding an evolved G alpha protein mutant from screened or selected products of (b).

A further aspect of the invention is a method for recombining at least a first and second DNA substrate molecule, comprising:

(a) transfecting a host cell with at least a first and second DNA substrate molecule wherein the at least a first and second DNA substrate molecules are recombined in the host cell;

(b) screening or selecting the products of (a) for a desired property; and (c) recovering recombinant DNA substrate molecules from (b).

A further aspect of the invention is a method for evolving a DNA substrate sequence encoding a protein of interest, wherein the DNA substrate comprises a vector, the vector comprising single-stranded DNA, the method comprising:

(a) providing single-stranded vector DNA and a library of mutants of the DNA substrate sequence;

(b) annealing single stranded DNA from the library of (a) to the single stranded vector DNA of (a);

(c) transforming the products of (b) into a host;

(d) screening the product of (c) for a desired property; and (e) recovering evolved DNA substrate DNA from the products of (d).

BRIEF DESCRIPTION OF THE DRAWINGS

FIGS. 2A–2G depict the alignment of alpha interferon amino acid and nucleic acid sequences (SEQ ID NO.s 75–86 and 87–98 respectively).

DESCRIPTION OF SPECIFIC EMBODIMENTS

Figure 1:
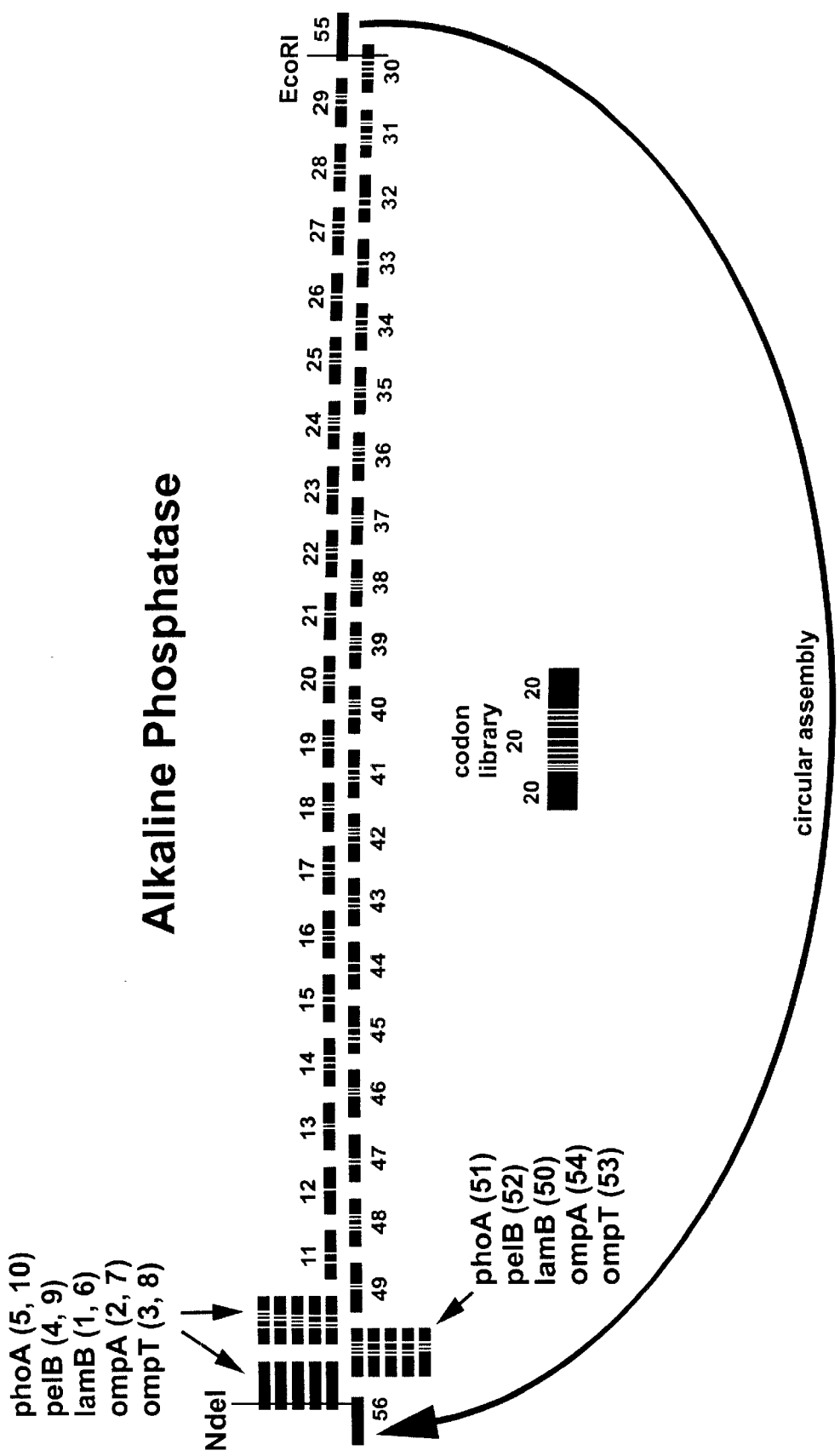
FIG. 1 depicts the alignment of oligo PCR primers for evolution of bovine calf intestinal alkaline phosphatase.

The invention provides a number of strategies for evolving polypeptides through recursive recombination methods. In some embodiments, the strategies of the invention can generally be classified as "coarse grain shuffling" and "fine grain shuffling." As described in detail below, these strategies are especially applicable in situations where some structural or functional information is available regarding the polypeptides of interest, where the nucleic acid to be manipulated is large, when selection or screening of many recombinants is cumbersome, and so on. "Coarse grain shuffling" generally involves the exchange or recombination of segments of nucleic acids, whether defined as functional domains, exons, restriction endonuclease fragments, or otherwise arbitrarily defined segments. "Fine grain shuffling" generally involves the introduction of sequence variation within a segment, such as within codons.

Coarse grain and fine grain shuffling allow analysis of variation occuring within a nucleic acid sequence, also termed "searching of sequence space." Although both techniques are meritorious, the results are qualitatively different. For example, coarse grain searches are often better suited for optimizing multigene clusters such as polyketide operons, whereas fine grain searches are often optimal for optimizing a property such as protein expression using codon usage libraries.

The strategies generally entail evolution of gene(s) is or segment(s) thereof to allow retention of function in a heterologous cell or improvement of function in a homologous or heterologous cell. Evolution is effected generally by a process termed recursive sequence recombination. Recursive sequence recombination can be achieved in many different formats and permutations of formats, as described in further detail below. These formats share some common principles. Recursive sequence recombination entails successive cycles of recombination to generate molecular diversity, i.e., the creation of a family of nucleic acid molecules showing substantial sequence identity to each other but differing in the presence of mutations. Each recombination cycle is followed by at least one cycle of screening or selection for molecules having a desired characteristic. The molecule(s) selected in one round form the starting materials for generating diversity in the next round. In any given cycle, recombination can occur in vivo or in vitro. Furthermore, diversity resulting from recombination can be augmented in any cycle by applying prior methods of mutagenesis (e.g., error-prone PCR or cassette mutagenesis, passage through bacterial mutator strains, treatment with chemical mutagens) to either the substrates for or products of recombination.

I. Formats for Recursive Sequence Recombination

Some formats and examples for recursive sequence recombination, sometimes referred to as DNA shuffling, evolution, or molecular breeding, have been described by the present inventors and co-workers in co-pending applications U.S. patent application Ser. No. 08/198,431, filed Feb. 17, 1994, Ser. No. PCT/US95/02126, filed, Feb. 17, 1995 (International Publication No. WO 95/22625), Ser. No. 08/425,684, filed Apr. 18, 1995, Ser. No. 08/537,874, filed Oct. 30, 1995, Ser. No. 08/564,955, filed Nov. 30, 1995, Ser. No. 08/621,859, filed Mar. 25, 1996, Ser. No. 08/621,430, filed Mar. 25, 1996, Ser. No. PCT/US96/05480, filed Apr. 18, 1996 (International Publication No. WO 96/33207), Ser. No. 08/650,400, filed May 20, 1996, Ser. No. 08/675,502, filed Jul. 3, 1996, Ser. No. 08/721,824, filed Sep. 27, 1996, and 08/722,660 filed Sep. 27, 1996; Stemmer, Science 270:1510 (1995); Stemmer et al., Gene 164:49–53 (1995); Stemmer, Bio/Technology 13:549–553 (1995); Stemmer, Proc. Natl. Acad. Sci. U.S.A. 91:10747–10751 (1994); Stemmer, Nature 370:389–391 (1994); Crameri et al., Nature Medicine 2(1):1–3 (1996); Crameri et al., Nature Biotechnology 14:315–319 (1996), each of which is incorporated by reference in its entirety for all purposes.

In general, the term "gene" is used herein broadly to refer to any segment or sequence of DNA associated with a biological function. Genes can be obtained from a variety of sources, including cloning from a source of interest or synthesizing from known or predicted sequence information, and may include sequences designed to have desired parameters.

A wide variety of cell types can be used as a recipient of evolved genes. Cells of particular interest include many bacterial cell types, both gram-negative and gram-positive, such as Rhodococcus, Streptomyces, Actinomycetes, Corynebacteria, Penicillium, Bacillus, *Escherichia coli*, Pseudomonas, Salmonella, and Erwinia. Cells of interest also include eukaryotic cells, particularly mammalian cells (e.g., mouse, hamster, primate, human), both cell lines and primary cultures. Such cells include stem cells, including embryonic stem cells, zygotes, fibroblasts, lymphocytes, Chinese hamster ovary (CHO), mouse fibroblasts (NIH3T3), kidney, liver, muscle, and skin cells. Other eukaryotic cells of interest include plant cells, such as maize, rice, wheat, cotton, soybean, sugarcane, tobacco, and arabidopsis; fish, algae, fungi (Penicillium, Fusarium, Aspergillus, Podospora, Neurospora), insects, yeasts (Picchia and Saccharomyces).

The choice of host will depend on a number of factors, depending on the intended use of the engineered host, including pathogenicity, substrate range, environmental hardiness, presence of key intermediates, ease of genetic manipulation, and likelihood of promiscuous transfer of genetic information to other organisms. A preferred host has the ability to replicate vector DNA, express proteins of interest, and properly traffic proteins of interest. Particularly advantageous hosts are *E. coli*, lactobacilli, Streptomycetes, Actinomycetes, fungi such as *Saccaromyces cerivisiae* or *Pischia pastoris*, Schneider cells, L-cells, COS cells, CHO cells, and transformed B cell lines such as SP2/0, J558, NS-1 and AG8-653.

The breeding procedure starts with at least two substrates that generally show substantial sequence identity to each other (i.e., at least about 50%, 70%, 80% or 90% sequence identity), but differ from each other at certain positions. The difference can be any type of mutation, for example, substitutions, insertions and deletions. Often, different segments differ from each other in perhaps 5–20 positions. For recombination to generate increased diversity relative to the starting materials, the starting materials must differ from each other in at least two nucleotide positions. That is, if there are only two substrates, there should be at least two divergent positions. If there are three substrates, for example, one substrate can differ from the second as a single position, and the second can differ from the third at a different single position. The starting DNA segments can be natural variants of each other, for example, allelic or species variants. The segments can also be from nonallelic genes showing some degree of structural and usually functional relatedness (e.g., different genes within a superfamily such as the immunoglobulin superfamily). The starting DNA segments can also be induced variants of each other. For example, one DNA segment can be produced by error-prone PCR replication of the other, or by substitution of a mutagenic cassette. Induced mutants can also be prepared by propagating one (or both) of the segments in a mutagenic strain. In these situations, strictly speaking, the second DNA segment is not a single segment but a large family of related segments. The different segments forming the starting materials are often the same length or substantially the same length. However, this need not be the case; for example; one segment can be a subsequence of another. The segments can be present as part of larger molecules, such as vectors, or can be in isolated form.

The starting DNA segments are recombined by any of the recursive sequence recombination formats provided herein to generate a diverse library of recombinant DNA segments. Such a library can vary widely in size from having fewer than 10 to more than $10^5$, $10^9$, or $10^{12}$ members. In general, the starting segments and the recombinant libraries generated include full-length coding sequences and any essential regulatory sequences, such as a promoter and polyadenylation sequence, required for expression. However, if this is not the case, the recombinant DNA segments in the library can be inserted into a common vector providing the missing sequences before performing screening/selection.

If the recursive sequence recombination format employed is an in vivo format, the library of recombinant DNA segments generated already exists in a cell, which is usually the cell type in which expression of the enzyme with altered substrate specificity is desired. If recursive sequence recombination is performed in vitro, the recombinant library is preferably introduced into the desired cell type before screening/selection. The members of the recombinant library can be linked to an episome or virus before introduction or can be introduced directly. In some embodiments of the invention, the library is amplified in a first host, and is then recovered from that host and introduced to a second host more amenable to expression, selection, or screening, or any other desirable parameter. The manner in which the library is introduced into the cell type depends on the DNA-uptake characteristics of the cell type, e.g., having viral receptors, being capable of conjugation, or being naturally competent. If the cell type is insusceptible to natural and chemical-induced competence, but susceptible to electroporation, one would usually employ electroporation. If the cell type is insusceptible to electroporation as well, one can employ biolistics. The biolistic PDS-1000 Gene Gun (Biorad, Hercules, Calif.) uses helium pressure to accelerate DNA-coated gold or tungsten microcarriers toward target cells. The process is applicable to a wide range of tissues, including plants, bacteria, fungi, algae, intact animal tissues, tissue culture cells, and animal embryos. One can employ electronic pulse delivery, which is essentially a mild electroporation format for live tissues in animals and patients. Zhao, *Advanced Drug Delivery Reviews* 17:257–262 (1995). Novel methods for making cells competent are described in co-pending application U.S. patent application Ser. No. 08/621,430, filed Mar. 25, 1996. After introduction of the library of recombinant DNA genes, the cells are optionally propagated to allow expression of genes to occur.

A. In Vitro Formats

One format for recursive sequence recombination utilizes a pool of related sequences. The sequences can be DNA or RNA and can be of various lengths depending on the size of the gene or DNA fragment to be recombined or reassembled. Preferably the sequences are from 50 bp to 100 kb.

The pool of related substrates can be fragmented, usually at random, into fragments of from about 5 bp to 5 kb or more. Preferably the size of the random fragments is from about 10 bp to 1000 bp, more preferably the size of the DNA fragments is from about 20 bp to 500 bp. The substrates can be digested by a number of different methods, such as DNAseI or RNAse digestion, random shearing or restriction enzyme digestion. The concentration of nucleic acid fragments of a particular length is often less than 0.1% or 1% by weight of the total nucleic acid. The number of different specific nucleic acid fragments in the mixture is usually at least about 100, 500 or 1000.

The mixed population of nucleic acid fragments are denatured by heating to about 80° C. to 100° C., more preferably from 900° C. to 960° C., to form single-stranded nucleic acid fragments. Single-stranded nucleic acid fragments having regions of sequence identity with other single-stranded nucleic acid fragments can then be reannealed by cooling to 20° C. to 75° C., and preferably from 40° C. to 65° C. Renaturation can be accelerated by the addition of polyethylene glycol ("PEG") or salt. The salt concentration is preferably from 0 mM to 600 mM, more preferably the salt concentration is from 10 mM to 100 mM. The salt may be such salts as $(NH_4)_2SO_4$, KCl, or NaCl. The concentration of PEG is preferably from 0% to 20%, more preferably from 5% to 10%. The fragments that reanneal can be from different substrates.

The annealed nucleic acid fragments are incubated in the presence of a nucleic acid polymerase, such as Taq or Klenow, $Mg^{++}$ at 1 mM–20 mM, and dNTP's (i.e. DATP, dCTP, dGTP and dTTP). If regions of sequence identity are large, Taq or other high-temperature polymerase can be used with an annealing temperature of between 45–65° C. If the areas of identity are small, Klenow or other low-temperature polymerases can be used with an annealing temperature of between 20–30° C. The polymerase can be added to the random nucleic acid fragments prior to annealing, simultaneously with annealing or after annealing.

The cycle of denaturation, renaturation and incubation of random nucleic acid fragments in the presence of polymerase is sometimes referred to as "shuffling" of the nucleic acid in vitro. This cycle is repeated for a desired number of times. Preferably the cycle is repeated from 2 to 100 times, more preferably the sequence is repeated from 10 to 40 times. The resulting nucleic acids are a family of double-stranded polynucleotides of from about 50 bp to about 100 kb, preferably from 500 bp to 50 kb. The population represents variants of the starting substrates showing substantial sequence identity thereto but also diverging at several positions. The population has many more members than the starting substrates. The population of fragments resulting from recombination is preferably first amplified by PCR, then cloned into an appropriate vector and the ligation mixture used to transform host cells.

In a variation of in vitro shuffling, subsequences of recombination substrates can be generated by amplifying the full-length sequences under conditions which produce a substantial fraction, typically at least 20 percent or more, of incompletely extended amplification products. The amplification products, including the incompletely extended amplification products are denatured and subjected to at least one additional cycle of reannealing and amplification. This variation, wherein at least one cycle of reannealing and amplification provides a substantial fraction of incompletely extended products, is termed "stuttering." In the subsequent amplification round, the incompletely extended products anneal to and prime extension on different sequence-related template species.

In a further variation, at least one cycle of amplification can be conducted using a collection of overlapping single-stranded DNA fragments of related sequence, and different lengths. Each fragment can hybridize to and prime polynucleotide chain extension of a second fragment from the collection, thus forming sequence-recombined polynucleotides. In a further variation, single-stranded DNA fragments of variable length can be generated from a single primer by Vent DNA polymerase on a first DNA template. The single stranded DNA fragments are used as primers for a second, Kunkel-type template, consisting of a uracil-containing circular single-stranded DNA. This results in multiple substitutions of the first template into the second (see Levichkin et al., *Mol. Biolocy* 29:572–577 (1995)).

Nucleic acid sequences can be recombined by recursive sequence recombination even if they lack sequence homology. Homology can be introduced using synthetic oligonucleotides as PCR primers. In addition to the specific sequences for the nucleic acid segment being amplified, all of the primers used to amplify one particular segment are synthesized to contain an additional sequence of 20–40 bases 5' to the gene (sequence A) and a different 20–40 base sequence 3' to the segment (sequence B). An adjacent segment is amplified using a 5' primer which contains the complementary strand of sequence B (sequence B'), and a 3' primer containing a different 20–40 base sequence (C). Similarly, primers for the next adjacent segment contain sequences C' (complementary to C) and D. In this way, small regions of homology are introduced, making the segments into site-specific recombination cassettes. Subsequent to the initial amplification of individual segments, the amplified segments can then be mixed and subjected to primerless PCR.

When domains within a polypeptide are shuffled, it may not be possible to introduce additional flanking sequences to the domains, due to the constraint of maintaining a continuous open reading frame. Instead, groups of oligonucleotides are synthesized that are homologous to the 3' end of the first domain encoded by one of the genes to be shuffled, and the 5' ends of the second domains encoded by all of the other genes to be shuffled together. This is repeated with all domains, thus providing sequences that allow recombination between protein domains while maintaining their order.

B. In Vivo Formats

1. Plasmid-Plasmid Recombination

The initial substrates for recombination are a collection of polynucleotides comprising variant forms of a gene. The variant forms usually show substantial sequence identity to each other sufficient to allow homologous recombination between substrates. The diversity between the polynucleotides can be natural (e.g., allelic or species variants), induced (e.g., error-prone PCR or error-prone recursive sequence recombination), or the result of in vitro recombination. Diversity can also result from resynthesizing genes encoding natural proteins with alternative codon usage. There should be at least sufficient diversity between substrates that recombination can generate more diverse products than there are starting materials. There must be at least two substrates differing in at least two positions. However, commonly a library of substrates of $10^3$–$10^8$ members is employed. The degree of diversity depends on the length of the substrate being recombined and the extent of the functional change to be evolved. Diversity at between 0.1–25% of positions is typical. The diverse substrates are incorporated into plasmids. The plasmids are often standard cloning vectors, e.g., bacterial multicopy plasmids. However, in some methods to be described below, the plasmids include mobilization (MOB) functions. The substrates can be incorporated into the same or different plasmids. Often at least two different types of plasmid having different types of selectable markers are used to allow selection for cells containing at least two types of vector. Also, where different types of plasmid are employed, the different plasmids can come from two distinct incompatibility groups to allow stable co-existence of two different plasmids within the cell. Nevertheless, plasmids from the same incompatibility group can still co-exist within the same cell for sufficient time to allow homologous recombination to occur.

Plasmids containing diverse substrates are initially introduced into cells by any method (e.g., chemical transformation, natural competence, electroporation, biolistics, packaging into phage or viral systems). Often, the plasmids are present at or near saturating concentration (with respect to maximum transfection capacity) to increase the probability of more than one plasmid entering the same cell. The plasmids containing the various substrates can be transfected simultaneously or in multiple rounds. For example, in the latter approach cells can be transfected with a first aliquot of plasmid, transfectants selected and propagated, and then infected with a second aliquot of plasmid.

Having introduced the plasmids into cells, recombination between substrates to generate recombinant genes occurs within cells containing multiple different plasmids merely by propagating the cells. However, cells that receive only one plasmid are unable to participate in recombination and the potential contribution of substrates on such plasmids to evolution is not fully exploited (although these plasmids may contribute to some extent if they are progapated in mutator cells). The rate of evolution can be increased by allowing all substrates to participate in recombination. Such can be achieved by subjecting transfected cells to electroporation. The conditions for electroporation are the same as those conventionally used for introducing exogenous DNA into cells (e.g., 1,000–2,500 volts, 400 μF and a 1–2 mM gap). Under these conditions, plasmids are exchanged between cells allowing all substrates to participate in recombination. In addition the products of recombination can undergo further rounds of recombination with each other or with the original substrate. The rate of evolution can also be increased by use of conjugative transfer. To exploit conjugative transfer, substrates can be cloned into plasmids having MOB genes, and tra genes are also provided in cis or in trans to the MOB genes. The effect of conjugative transfer is very similar to electroporation in that it allows plasmids to move between cells and allows recombination between any substrate and the products of previous recombination to occur, merely by propagating the culture. The rate of evolution can also be increased by fusing cells to induce exchange of plasmids or chromosomes. Fusion can be induced by chemical agents, such as PEG, or viral proteins, such as influenza virus hemagglutinin, HSV-1 gB and gD. The rate of evolution can also be increased by use of mutator host cells (e.g., Mut L, S, D, T, H in bacteria and Ataxia telangiectasia human cell lines).

The time for which cells are propagated and recombination is allowed to occur, of course, varies with the cell type but is generally not critical, because even a small degree of recombination can substantially increase diversity relative to the starting materials. Cells bearing plasmids containing recombined genes are subject to screening or selection for a desired function. For example, if the substrate being evolved contains a drug resistance gene, one would select for drug resistance. Cells surviving screening or selection can be subjected to one or more rounds of screening/selection followed by recombination or can be subjected directly to an additional round of recombination. "Screening" as used herein is intended to include "selection" as a type of screen.

The next round of recombination can be achieved by several different formats independently of the previous round. For example, a further round of recombination can be effected simply by resuming the electroporation or conjugation-mediated intercellular transfer of plasmids described above. Alternatively, a fresh substrate or substrates, the same or different from previous substrates, can be transfected into cells surviving selection/screening. Optionally, the new substrates are included in plasmid vectors bearing a different selective marker and/or from a different incompatibility group than the original plasmids. As a further alternative, cells surviving selection/screening can be subdivided into two subpopulations, and plasmid DNA from one subpopulation transfected into the other, where the substrates from the plasmids from the two subpopulations undergo a further round of recombination. In either of the latter two options, the rate of evolution can be increased by employing DNA extraction, electroporation, conjugation or mutator cells, as described above. In a still further variation, DNA from cells surviving screening/selection can be extracted and subjected to in vitro recursive sequence recombination.

After the second round of recombination, a second round of screening/selection is performed, preferably under conditions of increased stringency. If desired, further rounds of recombination and selection/screening can be performed using the same strategy as for the second round. With successive rounds of recombination and selection/screening, the surviving recombined substrates evolve toward acquisition of a desired phenotype. Typically, in this and other methods of recursive recombination, the final product of recombination that has acquired the desired phenotype differs from starting substrates at 0.10–25% of positions and has evolved at a rate orders of magnitude in excess (e.g., by at least 10-fold, 100-fold, 1000-fold, or 10,000 fold) of the rate of evolution driven by naturally acquired mutation of about 1 mutation per $10^9$ positions per generation (see Andersson et al., *Proc. Natl. Acad. Sci. U.S.A.* 93:906–907 (1996)). The "final product" may be transferred to another host more desirable for utilization of the "shuffled" DNA. This is particularly advantageous in situations where the more desirable host is less efficient as a host for the many cycles of mutation/recombination due to the lack of molecular biology or genetic tools available for other organisms such as *E. coli*.

2. Virus-Plasmid Recombination

The strategy used for plasmid-plasmid recombination can also be used for virus-plasmid recombination; usually, phage-plasmid recombination. However, some additional comments particular to the use of viruses are appropriate. The initial substrates for recombination are cloned into both plasmid and viral vectors. It is usually not critical which substrate(s) is/are inserted into the viral vector and which into the plasmid, although usually the viral vector should contain different substrate(s) from the plasmid. As before, the plasmid (and the virus) typically contains a selective marker. The plasmid and viral vectors can both be introduced into cells by transfection as described above. However, a more efficient procedure is to transfect the cells with plasmid, select transfectants and infect the transfectants with virus. Because the efficiency of infection of many viruses approaches 100% of cells, most cells transfected and infected by this route contain both a plasmid and virus bearing different substrates.

Homologous recombination occurs between plasmid and virus generating both recombined plasmids and recombined virus. For some viruses, such as filamentous phage, in which intracellular DNA exists in both double-stranded and single-stranded forms, both can participate in recombination. Provided that the virus is not one that rapidly kills cells, recombination can be augmented by use of electroporation or conjugation to transfer plasmids between cells. Recombination can also be augmented for some types of virus by allowing the progeny virus from one cell to reinfect other cells. For some types of virus, virus-infected-cells show resistance to superinfection. However, such resistance can be overcome by infecting at high multiplicity and/or using mutant strains of the virus in which resistance to superinfection is reduced.

The result of infecting plasmid-containing cells with virus depends on the nature of the virus. Some viruses, such as filamentous phage, stably exist with a plasmid in the cell and also extrude progeny phage from the cell. Other viruses, such as lambda having a cosmid genome, stably exist in a cell like plasmids without producing progeny virions. Other viruses, such as the T-phage and lytic lambda, undergo recombination with the plasmid but ultimately kill the host cell and destroy plasmid DNA. For viruses that infect cells without killing the host, cells containing recombinant plasmids and virus can be screened/selected using the same approach as for plasmid-plasmid recombination. Progeny virus extruded by cells surviving selection/screening can also be collected and used as substrates in subsequent rounds of recombination. For viruses that kill their host cells, recombinant genes resulting from recombination reside only in the progeny virus. If the screening or selective assay requires expression of recombinant genes in a cell, the recombinant genes should be transferred from the progeny virus to another vector, e.g., a plasmid vector, and retransfected into cells before selection/screening is performed.

For filamentous phage, the products of recombination are present in both cells surviving recombination and in phage extruded from these cells. The dual source of recombinant products provides some additional options relative to the plasmid-plasmid recombination. For example, DNA can be isolated from phage particles for use in a round of in vitro recombination. Alternatively, the progeny phage can be used to transfect or infect cells surviving a previous round of screening/selection, or fresh cells transfected with fresh substrates for recombination.

3. Virus-Virus Recombination

The principles described for plasmid-plasmid and plasmid-viral recombination can be applied to virus-virus recombination with a few modifications. The initial substrates for recombination are cloned into a viral vector. Usually, the same vector is used for all substrates. Preferably, the virus is one that, naturally or as a result of mutation, does not kill cells. After insertion, some viral genomes can be packaged in vitro or using a packaging cell line. The packaged viruses are used to infect cells at high multiplicity such that there is a high probability that a cell will receive multiple viruses bearing different substrates.

After the initial round of infection, subsequent steps depend on the nature of infection as discussed in the previous section. For example, if the viruses have phagemid (Sambrook et al., *Molecular Cloning*, CSH Press, 1987) genomes such as lambda cosmids or M13, F1 or Fd phagemids, the phagemids behave as plasmids within the cell and undergo recombination simply by propagating the cells. Recombination is particularly efficient between single-stranded forms of intracellular DNA. Recombination can be augmented by electroporation of cells.

Following selection/screening, cosmids containing recombinant genes can be recovered from surviving cells, e.g., by heat induction of a cos⁻ lysogenic host cell, or extraction of DNA by standard procedures, followed by repackaging cosmid DNA in vitro.

If the viruses are filamentous phage, recombination of replicating form DNA occurs by propagating the culture of infected cells. Selection/screening identifies colonies of cells containing viral vectors having recombinant genes with improved properties, together with infectious particles (i.e., phage or packaged phagemids) extruded from such cells. Subsequent options are essentially the same as for plasmid-viral recombination.

4. Chromosome Recombination

This format can be used to especially evolve chromosomal substrates. The format is particularly preferred in situations in which many chromosomal genes contribute to a phenotype or one does not know the exact location of the chromosomal gene(s) to be evolved. The initial substrates for recombination are cloned into a plasmid vector. If the chromosomal gene(s) to be evolved are known, the substrates constitute a family of sequences showing a high degree of sequence identity but some divergence from the chromosomal gene. If the chromosomal genes to be evolved have not been located, the initial substrates usually constitute a library of DNA segments of which only a small number show sequence identity to the gene or gene(s) to be evolved. Divergence between plasmid-borne substrate and the chromosomal gene(s) can be induced by mutagenesis or by obtaining the plasmid-borne substrates from a different species than that of the cells bearing the chromosome.

The plasmids bearing substrates for recombination are transfected into cells having chromosomal gene(s) to be evolved. Evolution can occur simply by propagating the culture, and can be accelerated by transferring plasmids between cells by conjugation or electroporation. Evolution can be further accelerated by use of mutator host cells or by seeding a culture of nonmutator host cells being evolved with mutator host cells and inducing intercellular transfer of plasmids by electroporation or conjugation. Preferably, mutator host cells used for seeding contain a negative selectable marker to facilitate isolation of a pure culture of the nonmutator cells being evolved. Selection/screening identifies cells bearing chromosomes and/or plasmids that have evolved toward acquisition of a desired function.

Subsequent rounds of recombination and selection/screening proceed in similar fashion to those described for plasmid-plasmid recombination. For example, further recombination can be effected by propagating cells surviving recombination in combination with electroporation or conjugative transfer of plasmids. Alternatively, plasmids bearing additional substrates for recombination can be introduced into the surviving cells. Preferably, such plasmids are from a different incompatibility group and bear a different selective marker than the original plasmids to allow selection for cells containing at least two different plasmids. As a further alternative, plasmid and/or chromosomal DNA can be isolated from a subpopulation of surviving cells and transfected into a second subpopulation. Chromosomal DNA can be cloned into a plasmid vector before transfection.

5. Virus-Chromosome Recombination

As in the other methods described above, the virus is usually one that does not kill the cells, and is often a phage or phagemid. The procedure is substantially the same as for plasmid-chromosome recombination. Substrates for recombination are cloned into the vector. Vectors including the substrates can then be transfected into cells or in vitro packaged and introduced into cells by infection. Viral genomes recombine with host chromosomes merely by propagating a culture. Evolution can be accelerated by allowing intercellular transfer of viral genomes by electroporation, or reinfection of cells by progeny virions. Screening/selection identifies cells having chromosomes and/or viral genomes that have evolved toward acquisition of a desired function.

There are several options for subsequent rounds of recombination. For example, viral genomes can be transferred between cells surviving selection/recombination by electroporation. Alternatively, viruses extruded from cells surviving selection/screening can be pooled and used to superinfect the cells at high multiplicity. Alternatively, fresh substrates for recombination can be introduced into the cells, either on plasmid or viral vectors.

II. Application of Recursive Sequence Recombination to Evolution of Polypeptides In addition to the techniques described above, some additionally advantageous modifications of these techniques for the evolution of polypeptides are described below. These methods are referred to as "define grain" and "coarse grain" shuffling. The coarse grain methods allow one to exchange chunks of genetic material between substrate nucleic acids, thereby limiting diversity in the resulting recombinants to exchanges or substitutions of domains, restriction fragments, oligo-encoded blocks of mutations, or other arbitrarily defined segments, rather than introducing diversity more randomly across the substrate. In contrast to coarse grain shuffling, fine grain shuffling methods allow the generation of all possible recombinations, or permutations, of a given set of very closely linked mutations, including multiple permutations, within a single segment, such as a codon.

In some embodiments, coarse grain or fine grain shuffling techniques are not performed as exhaustive searches of all possible mutations within a nucleic acid sequence. Rather, these techniques are utilized to provide a sampling of variation possible within a gene based on known sequence or structural information. The size of the sample is typically determined by the nature of the screen or selection process. For example, when a screen is performed in a 96-well microtiter format, it may be preferable to limit the size of the recombinant library to about 100 such microtiter plates for convenience in screening.

A. Use of Restriction Enzyme Sites to Recombine Mutations

In some situations it is advantageous to use restriction enzyme sites in nucleic acids to direct the recombination of mutations in a nucleic acid sequence of interest. These techniques are particularly preferred in the evolution of fragments that cannot readily be shuffled by existing methods due to the presence of repeated DNA or other problematic primary sequence motifs. They are also preferred for shuffling large fragments (typically greater than 10 kb), such as gene clusters that cannot be readily shuffled and "PCR-amplified" because of their size. Although fragments up to 50 kb have been reported to be amplified by PCR (Barnes, *Proc. Natl. Acad. Sci.* (*U.S.A.*) 91:2216–2220 (1994)), it can be problematic for fragments over 10 kb, and thus alternative methods for shuffling in the range of 10–50 kb and beyond are preferred. Preferably, the restriction endonucleases used are of the Class II type (Sambrook et al., *Molecular Cloning*, CSH Press, 1987) and of these, preferably those which generate nonpalindromic sticky end overhangs such as Alwn I, Sfi I or BstX1. These enzymes generate nonpalindromic ends that allow for efficient ordered reassembly with DNA ligase. Typically, restriction enzyme (or endonuclease) sites are identified by conventional restriction enzyme mapping techniques (Sambrook et al., *Molecular Cloning*, CSH Press, 1987), by analysis of sequence information for that gene, or by introduction of desired restriction sites into a nucleic acid sequence by synthesis (i.e. by incorporation of silent mutations).

The DNA substrate molecules to be digested can either be from in vivo replicated DNA, such as a plasmid preparation, or from PCR amplified nucleic acid fragments harboring the restriction enzyme recognition sites of interest, preferably near the ends of the fragment. Typically, at least two variants of a gene of interest, each having one or more mutations, are digested with at least one restriction enzyme determined to cut within the nucleic acid sequence of interest. The restriction fragments are then joined with DNA ligase to generate full length genes having shuffled regions. The number of regions shuffled will depend on the number of cuts within the nucleic acid sequence of interest. The shuffled molecules can be introduced into cells as described above and screened or selected for a desired property. Nucleic acid can then be isolated from pools (libraries) or clones having desired properties and subjected to the same procedure until a desired degree of improvement is obtained.

In some embodiments, at least one DNA substrate molecule or fragment thereof is isolated and subjected to mutagenesis. In some embodiments, the pool or library of religated restriction fragments are subjected to mutagenesis before the digestion-ligation process is repeated. "Mutagenesis" as used herein comprises such techniques known in the art as PCR mutagenesis, oligonucleotide-directed mutagenesis, site-directed mutagenesis, etc., and recursive sequence recombination by any of the techniques described herein.

An example of the use of this format is in the manipulation of polyketide clusters. Polyketide clusters (Khosla et al., *TIBTECH* 14, September 1996) are typically 10 to 100 kb in length, specifying multiple large polypeptides which assemble into very large multienzyme complexes. Due to the modular nature of these complexes and the modular nature of the biosynthetic pathway, nucleic acids encoding protein modules can be exchanged between different polyketide clusters to generate novel and functional chimeric polyketides. The introduction of rare restriction endonuclease sites such as SfiI (eight base recognition, nonpalindromic overhangs) at nonessential sites between polypeptides or in introns engineered within polypeptides would provide "handles" with which to manipulate exchange of nucleic acid segments using the technique described above.

B. Reassembly PCR

A further technique for recursively recombining mutations in a nucleic acid sequence utilizes "reassembly PCR". This method can be used to assemble multiple segments that have been separately evolved into a full length nucleic acid template such as a gene. This technique is performed when a pool of advantageous mutants is known from previous work or has been identified by screening mutants that may have been created by any mutagenesis technique known in the art, such as PCR mutagenesis, cassette mutagenesis, doped oligo mutagenesis, chemical mutagenesis, or propagation of the DNA template in vivo in mutator strains. Boundaries defining segments of a nucleic acid sequence of interest preferably lie in intergenic regions, introns, or areas of a gene not likely to have mutations of interest. Preferably, oligonucleotide primers (oligos) are synthesized for PCR amplification of segments of the nucleic acid sequence of interest, such that the sequences of the oligonucleotides overlap the junctions of two segments. The overlap region is typically about 10 to 100 nucleotides in length. Each of the segments is amplified with a set of such primers. The PCR products are then "reassembled" according to assembly protocols such as those used in Sections IA-B above to assemble randomly fragmented genes. In brief, in an assembly protocol the PCR products are first purified away from the primers, by, for example, gel electrophoresis or size exclusion chromatography. Purified products are mixed together and subjected to about 1–10 cycles of denaturing, reannealing, and extension in the presence of polymerase and deoxynucleoside triphosphates (dNTP's) and appropriate buffer salts in the absence of additional primers ("self-priming"). Subsequent PCR with primers flanking the gene are used to amplify the yield of the fully reassembled and shuffled genes. This method is necessarily "coarse grain" and hence only recombines mutations in a blockwise fashion, an advantage for some searches such as when recombining allelic variants of multiple genes within an operon.

In some embodiments, the resulting reassembled genes are subjected to mutagenesis before the process is repeated.

In some embodiments, oligonucleotides that incorporate uracil into the primers are used for PCR amplification. Typically uracil is incorporated at one site in the oligonucleotide. The products are treated with uracil glycosylase, thereby generating a single-stranded overhang, and are reassembled in an ordered fashion by a method such as disclosed by Rashtchian (*Current Biology*, 6:30–36 (1995)).

In a further embodiment, the PCR primers for amplification of segments of the nucleic acid sequence of interest are used to introduce variation into the gene of interest as follows. Mutations at sites of interest in a nucleic acid sequence are identified by screening or selection, by sequencing homologues of the nucleic acid sequence, and so on. Oligonucleotide PCR primers are then synthesized which encode wild type or mutant information at sites of interest. These primers are then used in PCR mutagenesis to generate libraries of full length genes encoding permutations of wild type and mutant information at the designated positions. This technique is typically advantagous in cases where the screening or selection process is expensive, cumbersome, or impractical relative to the cost of sequencing the genes of mutants of interest and synthesizing mutagenic oligonucleotides.

An example of this method is the evolution of an improved Taq polymerase, as described in detail below. Mutant proteins resulting from application of the method are identified and assayed in a sequencing reaction to identify mutants with improved sequencing properties. This is typically done in a high throughput format (see, for example, Broach et al. *Nature* 384 (Supp): 14–16 (1996)) to yield, after screening, a small number, e.g., about 2 to 100, of candidate recombinants for further evaluation. The mutant genes can then be sequenced to provide information regarding the location of the mutation. The corresponding mutagenic oligonucleotide primers can be synthesized from this information, and used in a reassembly reaction as described above to efficiently generate a library with an average of many mutations per gene. Thus, multiple rounds of this protocol allows the efficient search for improved variants of the Taq polymerase.

C. Enrichment for Mutant Sequence Information

In some embodiments of the invention, recombination reactions, such as those discussed above, are enriched for mutant sequences so that the multiple mutant spectrum, i.e. possible combinations of mutations, is more efficiently sampled. The rationale for this is as follows. Assume that a number, n, of mutant clones with improved activity is obtained, wherein each clone has a single point mutation at a different position in the nucleic acid sequence. If this population of mutant clones with an average of one mutation of interest per nucleic acid sequence is then put into a recombination reaction, the resulting population will still have an average of one mutation of interest per nucleic acid sequence as defined by a Poisson distribution, leaving the multiple mutation spectrum relatively unpopulated.

The amount of screening required to identify recombinants having two or more mutations can be dramatically reduced by the following technique. The nucleic acid sequences of interest are obtained from a pool of mutant clones and prepared as fragments, typically by digestion with a restriction endonuclease , sonication, or by PCR amplification. The fragments are denatured, then allowed to reanneal, thereby generating mismatched hybrids where one strand of a mutant has hybridized with a complementary strand from a different mutant or wild-type clone. The reannealed products are then fragmented into fragments of about 20–100 bp, for example, by the use of DNAseI. This fragmentation reaction has the effect of segregating regions of the template containing mismatches (mutant information) from those encoding wild type sequence. The mismatched hybrids can then be affinity purified using aptamers, dyes, or other agents which bind to mismatched DNA. A preferred embodiment is the use of mutS protein affinity matrix (Wagner et al., *Nucleic Acids Res.* 23(19):3944–3948 (1995); Su et al., *Proc. Natl. Acad. Sci.* (*U.S.A.*), 83:5057–5061(1986)) with a preferred step of amplifying the affinity-purified material in vitro prior to an assembly reaction. This amplified material is then put into a assembly PCR reaction as decribed above. Optionally, this material can be titrated against the original mutant pool (e.g., from about 100% to 10% of the mutS enriched pool) to control the average number of mutations per clone in the next round of recombination.

Another application of this method is in the assembly of gene constructs that are enriched for polymorphic bases occurring as natural or selected allelic variants or as differences between homologous genes of related species. For example, one may have several varieties of a plant that are believed to have heritable variation in a trait of interest (e.g., drought resistance). It then is of interest to construct a library of these variant genes containing many mutations per gene. MutS selection can be applied in combination with the assembly techniques described herein to generate such a pool of recombinants that are highly enriched for polymorphic ("mutant") information. In some embodiments, the pool of recombinant genes is provided in a transgenic host. Recombinants can be further evolved by PCR amplification of the transgene from transgenic organisms that are determined to have an improved phenotype and applying the formats described in this invention to further evolve them.

D. Intron-driven Recombination

In some instances, the substrate molecules for recombination have uniformly low homology, sporadically distributed regions of homology, or the region of homology is relatively small (for example, about 10–100 bp), such as phage displayed peptide ligands. These factors can reduce the efficiency and randomness of recombination in RSR. In some embodiments of the invention, this problem is addressed by the introduction of introns between coding exons in sequences encoding protein homologues. In further embodiments of the invention, introns can be used (Chong et al., *J. Biol. Chem.*, 271:22159–22168 (1996)).

In this method, a nucleic acid sequence, such as a gene or gene family, is arbitrarily defined to have segments. The segments are preferably exons. Introns are engineered between the segments. Preferably, the intron inserted between the first and second segments is at least about 10% divergent from the intron inserted between second and third segments, the intron inserted between second and third segments is at least about 10% divergent from the introns inserted between any of the previous segment pairs, and so on through segments n and n+1. The introns between any given set of exons will thus initially be identical between all clones in the library, whereas the exons can be arbitrarily divergent in sequence. The introns therefore provide homologous DNA sequences that will permit application of any of the described methods for RSR while the exons can be arbitrarily small or divergent in sequence, and can evolve to achieve an arbitrarily large degree of sequence divergence without a significant loss in efficiency in recombination. Restriction sites can also be engineered into the intronic nucleic acid sequence of interest so as to allow a directed reassemmbly of restriction fragments. The starting exon DNA may be synthesized de novo from sequence information, or may be present in any nucleic acid preparation (e.g., genomic, cDNA, libraries, and so on). For example, 1 to 10 nonhomologous introns can be designed to direct recombination of the nucleic acid sequences of interest by placing them between exons. The sequence of the introns can be all or partly obtained from known intron sequence. Preferably, the introns are self-splicing. Ordered sets of introns and exon libraries are assembled into functional genes by standard methods (Sambrook et al., *Molecular Cloning*, CSH Press (1987)).

Any of the formats for in vitro or in vivo recombination described herein can be applied for recursive exon shuffling. A preferred format is to use nonpalindromic restriction sites such as Sfi I placed into the intronic sequences to promote shuffling. Pools of selected clones are digested with Sfi I and religated. The nonpalindromic overhangs promote ordered reassembly of the shuffled exons. These libraries of genes can be expressed and screened for desired properties, then subjected to further recursive rounds of recombination by this process. In some embodiments, the libraries are subjected to mutagenesis before the process is repeated.

An example of how the introduction of an intron into a mammalian library format would be used advantageously is as follows. An intron containing a lox (Sauer et al., *Proc. Natl. Acad. Sci. (U.S.A.)*, 85:5166–5170 (1988)) site is arbitrarily introduced between amino acids 92 and 93 in each alpha interferon parental substrate. A library of $10^4$ chimeric interferon genes is made for each of the two exons (residues 1–92 and residues 93–167), cloned into a replicating plasmid vector, and introduced into target cells. The number $10^4$ is arbitrarily chosen for convenience in screening. An exemplary vector for expression in mammalian cells would contain an SV40 origin, with the host cells expressing SV40 large T antigen, so as to allow transient expression of the interferon constructs. The cells are challenged with a cytopathic virus such as vesicular stomatitis virus (VSV) in an interferon protection assay (e.g., Meister et al., *J. Gen. Virol.* 67:1633–1643, (1986)). Cells surviving due to expression of interferon are recovered, the two libraries of interferon genes are PCR amplified, and recloned into a vector that can be amplified in *E. coli*. The amplified plasmids are then transfected at high multiplicity (e.g. 10 micrograms of plasmid per $10^6$ cells) into a cre expressing host that can support replication of that vector. The presence of cre in the host cells promotes efficient recombination at the lox site in the interferon Intron, thus shuffling the selected sets of exons. This population of cells is then used in a second round of selection by viral challenge and the process is applied recursively. In this format, the cre recombinase is preferably expressed transiently on a cotransfected molecule that cannot replicate in the host. Thus, after segregation of recombinants from the cre expressing plasmid, no further recombination will occur and selection can be performed on genetically stable exon permutations. The method can be used with more than one intron, with recombination enhancing sequences other than cre/lox (e.g., int/xis, etc.), and with other vector systems such as but not limited to retroviruses, adenovirus or adeno-associated virus.

5. Synthetic Olicronucleotide Mediated Recombination

1. Oligo Bridge Across Sequence Space

In some embodiments of the invention, a search of a region of sequence space defined by a set of substrates, such as members of a gene family, having less than about 80%, more typically, less than about 50% homology, is desired. This region, which can be part or all of a gene or a gene is arbitrarily delineated into segments. The segment borders can be chosen randomly, based on correspondence with natural exons, based on structural considerations (loops, alpha helices, subdomains, whole domains, hydrophobic core, surface, dynamic simulations), and based on correlations with genetic mapping data.

Typically, the segments are then amplified by PCR with a pool of "bridge" oligonucleotides at each junction. Thus, if the set of five genes is broken into three segments A, B and C, and if there are five versions of each segment (A1, A2, ... C4, C5), twenty five oligonucleotides are made for each strand of the A-B junctions where each bridge oligo has 20 bases of homology to one of the A and one of the B segments. In some cases, the number of required oligonucleotides can be reduced by choosing segment boundaries that are identical in some or all of the gene family members. Oligonucleotides are similarly synthesized for the B-C junction. The family of A domains is amplified by PCR with an outside generic A primer and the pool of A-B junction oligonucleotides; the B domains with the A-B plus the B-C bridge oligonucleotides, and the C domains with the B-C bridge oligonucleotides plus a generic outside primer. Full length genes are made then made by assembly PCR or by the dUTP/uracil glycosylase methods described above. Preferably, products from this step are subjected to mutagenesis before the process of selection and recombination is repeated, until a desired level of improvement or the evolution of a desired property is obtained. This is typically determined using a screening or selection as appropriate for the protein and property of interest.

An illustration of this method is illustrated below for the recombination of eleven homologous human alpha interferon genes.

2. Site Directed Mutagenesis (SDM) with Oligonucleotides Encoding Homologue Mutations Followed by Shuffling In some embodiments of the invention, sequence information from one or more substrate sequences is added to a given "parental" sequence of interest, with subsequent recombination between rounds of screening or selection. Typically, this is done with site-directed mutagenesis performed by techniques well known in the art (Sambrook et al., *Molecular Cloning*, CSH Press (1987)) with one substrate as template and oligonucleotides encoding single or multiple mutations from other substrate sequences, e.g. homologous genes. After screening or selection for an improved phenotype of interest, the selected recombinant(s) can be further evolved using RSR techniques described herein. After screening or selection, site-directed mutagenesis can be done again with another collection of oligonucleotides encoding homologue mutations, and the above process repeated until the desired properties are obtained.

When the difference between two homologues is one or more single point mutations in a codon, degenerate oligonucleotides can be used that encode the sequences in both homologues. One oligo may include many such degenerate codons and still allow one to exhaustively search all permutations over that block of sequence. An example of this is provided below for the evolution of alpha interferon genes.

When the homologue sequence space is very large, it can be advantageous to restrict the search to certain variants. Thus, for example, computer modelling tools (Lathrop et al., *J. Mol. Biol.*, 255:641–665 (1996)) can be used to model each homologue mutation onto the target protein and discard any mutations that are predicted to grossly disrupt structure and function.

F. Recombination Directed by Host Machinery

In some embodiments of the invention, DNA substrate molecules are introduced into cells, wherein the cellular machinery directs their recombination. For example, a library of mutants is constructed and screened or selected for mutants with improved phenotypes by any of the techniques described herein. The DNA substrate molecules encoding the best candidates are recovered by any of the techniques described herein, then fragmented and used to transfect a mammalian host and screened or selected for improved function. The DNA substrate molecules are recovered from the mammalian host, such as by PCR, and the process is repeated until a desired level of improvement is obtained. In some embodiments, the fragments are denatured and reannealed prior to transfection, coated with recombination stimulating proteins such as recA, or co-transfected with a selectable marker such as NeoR to allow the positive selection for cells receiving recombined versions of the gene of interest.

For example, this format is preferred for the in vivo affinity maturation of an antibody by RSR. In brief, a library of mutant antibodies is generated, as described herein for the 48G7 affinity maturation. This library is FACS purified with ligand to enrich for antibodies with the highest 0.1–10% affinity. The V regions genes are recovered by PCR, fragmented, and cotransfected or electorporated with a vector into which reassembled V region genes can recombine. DNA substrate molecules are recovered from the cotranfected cells, and the process is repeated until the desired level of improvment is obtained. Other embodiments include reassembling the V regions prior to the electroporation so that an intact V region exon can recombine into an antibody expression cassette. Further embodiments include the use of this format for other eukaryotic genes or for the evolution of whole viruses.

G. Phagemid-Based Assembly

In some embodiments of the invention, a gene of interest is cloned into a vector that generates single stranded DNA, such as a phagemid. The resulting DNA substrate is mutagenzied by RSR in any method known in the art, transfected into host cells, and subjected to a screen or selection for a desired property or improved phenotype. DNA from the selected or screened phagemids is amplified, by, for example, PCR or plasmid preparation. This DNA preparation contains the various mutant sequences that one wishes to permute. This DNA is fragmented and denatured, and annealed with single-stranded DNA (ssDNA) phagemid template (ssDNA encoding the wild-type gene and vector sequences). A preferred embodiment is the use of dut(−) ung(−) host strains such as CJ236 (Sambrook et al., *Molecular Cloning* CSH Press (1987)) for the preparation of ssDNA.

Gaps in annealed template are filled with DNA polymerase and ligated to form closed relaxed circles. Since multiple fragments can anneal to the phagemid, the newly synthesized strand now consists of shuffled sequences. These products are transformed into a mutS strain of *E. coli* which is dut+ ung+. Phagemid DNA is recovered from the transfected host and subjected again to this protocol until the desired level of improvement is obtained. The gene encoding the protein of interest in this library of recovered phagemid DNA can be mutagenzied by any technique, including RSR, before the process is repeated.

III. Improved Protein Expression

While recombinant DNA technology has proved to be a very general method for obtaining large, pure, and homogeneous quantities of almost all nucleic acid sequences of interest, similar generality has not yet been achieved for the production of large amounts of pure, homogeneous protein in recombinant form. A likely explanation is that protein expression, folding, localization and stability is intrinsically more complex and unpredictable than for DNA. The yield of expressed protein is a complex function of transcription rates, translation rates, interactions with the ribosome, interaction of the nascent polypeptide with chaperonins and other proteins in the cell, efficiency of oligomerization, interaction with components of secretion and other protein trafficking pathways, protease sensitivity, and the intrinsic stability of the final folded state. Optimization of such complex processes is well suited for the application of RSR. The following methods detail strategies for application of RSR to the optimization of protein expression.

A. Evolution of Mutant Genes with Improved Expression Using RSR on Codon Usage Libraries The negative effect of rare *E. coli* codons on expression of recombinant proteins in this host has been clearly demonstrated (Rosenberg, et al., *J. Bact.* 175:716–22 (1993)). However, general rules for the choice of codon usage patterns to optimize expression of functional protein have been elusive. In some embodiments of the invention, protein expression is optimized by changing codons used in the gene of interest, based on the degeneracy of the genetic code. Typically, this is accomplished by synthesizing the gene using degenerate oligonucleotides. In some embodiments the degenerate oligonucleotides have the general structure of about 20 nucleotides of identity to a DNA substrate molecule encoding a protein of interest, followed by a region of about 20 degenerate nucleotides which encode a region of the protein, followed by another region of about 20 nucleotides of identity. In a preferred embodiment, the region of identity utilizes preferred codons for the host. In a further embodiment, the oligonucleotides are identical to the DNA substrate at least one 5' and one 3' nucleotide, but have at least 85% sequence homology to the DNA substrate molecule, with the difference due to the use of degenerate codons. In some embodiments, a set of such degenerate oligonucleotides is used in which each oligonucleotide overlaps with another by the general formula n−10, wherein n is the length of the oligonucleotide. Such oligonucleotides are typically about 20–1000 nucleotides in length. The assembled genes are then cloned, expressed, and screened or selected for improved expression. The assembled genes can be subjected to recursive recombination methods as descibed above until the desired improvement is achieved.

For example, this technique can be used to evolve bovine intestinal alkaline phosphatase (BIAP) for active expression in *E. coli*. This enzyme is commonly used as a reporter gene in assay formats such as ELISA. The cloned gene cannot be expressed in active form in a prokaryotic host such as *E. coli* in good yield. Development of such an expression system would allow one to access inexpensive expression technology for BIAP and, importantly, for engineered variants with improved activity or chemical coupling properties (such as chemical coupling to antibodies). A detailed example is provide in the Experimental Examples section.

B. Improved Folding

In some embodiments of the invention, proteins of interest when overexpressed or expressed in heterologous hosts form inclusion bodies, with the majority of the expressed protein being found in insoluble aggregates. Recursive sequence recombination techniques can be used to optimize folding of such target proteins. There are several ways to improve folding, including mutating evolving the target protein of interest and evolving chaperonin proteins.

1. Evolving A Target Protein a. Inclusion Body Fractionation Selection Using lac Headpiece Dimer Fusion Protein The lac repressor "headpiece dimers is a small protein containing two headpiece domains connected by a short peptide linker which binds the lac operator with sufficient affinity that polypeptide fusions to this headpiece dimer will remain bound to the plasmid that encodes them throughout an affinity purification process (Gates et al., *J. Mol. Biol.* 255:373–386 (1995)). This property can be exploited, as follows, to evolve mutant proteins of interest with improved folding properties. The protein of interest can be mammalian, yeast, bacterial, etc.

A fusion protein between the lac headpiece dimer and a target protein sequence is constructed, for example, as disclosed by Gates (supra). This construct, containing at least one lac operator, is mutagenized by technologies common in the arts such as PCR mutagenesis, chemical mutagenesis, oligo directed mutagenesis (Sambrook et al., *Molecular Cloninc* CSH Press (1987)). The resulting library is transformed into a host cell, and expression of the fusion protein is induced, preferably with arabinose. An extract or lysate is generated from a culture of the library expressing the construct. Insoluble protein is fractionated from soluble protein/DNA complexes by centrifugation or affinity chromatography, and the yield of soluble protein/DNA complexes is quantitated by quantitative PCR (Sambrook et al., *Molecular Cloning*, CSH Press, 1987) of the plasmid. Preferably, a reagent that is specific for properly folded protein, such as a monoclonal antibody or a natural ligand, is used to purify soluble protein/DNA complexes. The plasmid DNA from this step is isolated, subjected to RSR and again expressed. These steps are repeated until the yield of soluble protein/DNA complexes has reached a desired level of improvement. Individual clones are then screened for retention of functional properties of the protein of interest, such as enzymatic activity, etc.

This technique is generically useful for evolving solubility and other properties such as cellular trafficking of proteins heterologously expressed in a host cell of interest. For example, one could select for efficient folding and nuclear localization of a protein fused to the lac repressor headpiece dimer by encoding the protein on a plasmid encoding an SV40 origin of replication and a lac operator, and transiently expressing the fusion protein in a mammalian host expressing T antigen. Purification of protein/DNA complexes from nuclear HIRT extracts (Seed and Aruffo, *Proc. Natl. Acad. Sci.* (*U.S.A.*), 84:3365–3369 (1987)) would allow one to select for efficient folding and nuclear localization proteins.

b. Functional Expression of Protein Using Phase Display

A problem often encountered in phage display methods such as those disclosed by O'Neil et al. (*Current Biology*, 5:443–449 (1995)) is the inability to functionally express a protein of interest on phage. Without being limited to any one theory, improper folding of the protein of interest can be responsible for this problem. RSR can be used to evolve a protein of interest for functional expression on phage. Typically, a fusion protein is constructed between gene III or gene VIII and the target protein and then mutagenized, for example by PCR mutagenesis. The mutagenzied library is then expressed in a phage display format, a phage lysate is made, and these phage are affinity selected for those bearing functionally displayed fusion proteins using an affinity matrix containing a known ligand for the target protein. DNA from the functionally selected phage is purified, and the displayed genes of interest are shuffled and recloned into the phage display format. The selection, shuffling and recloning steps are repeated until the yield of phage with functional displayed protein has reached desired levels as defined, for example, by the fraction of phage that are retained on a ligand affinity matrix or the biological activity associated with the displayed phage. Individual clones are then screened to identify candidate mutants with improved display properties, desired level of expression, and functional properties of interest (e.g., ability to bind a ligand or receptor, lymphokine activity, enzymatic activity, etc.).

In some embodiments of the invention, a functional screen or selection is used to identify an evolved protein not expressed on a phage. The target protein, which cannot initially be efficiently expressed in a host of interest, is mutagenized and a functional screen or selection is used to identify cells expressing functional protein. For example, the protein of interest may complement a function in the host cell, cleave a calorimetric substrate, etc. Recursive sequence recombination is then used to rapidly evolve improved functional expression from such a pool of improved mutants.

For example, AMV reverse transcriptase is of particular commercial importance because it is active at a higher temperature (42° C.) and is more robust than many other reverse transcriptases. However, it is difficult to express in prokaryotic hosts such as *E. coli*, and is consequently expensive because it has to be purified from chicken cells. Thus an evolved AMV reverse transcriptase that can be expressed efficiently in *E. coli* is highly desirable.

In brief, the AMV reverse transcriptase gene (Papas et al., *J. Cellular Biochem* 20:95–103 (1982)) is mutagenized by any method common in the art. The library of mutant genes is cloned into a colE1 plasmid (Amp resistant) under control of the lac promoter in a polA12 (Ts) recA718 (Sweasy et al. *Proc. Natl. Acad. Sci. U.S.A.* 90:4626–630 (1993)) *E. coli* host. The library is induced with IPTG, and shifted to the nonpermissive temperature. This selects for functionally expressed reverse transcriptase genes under the selective conditions reported for selection of active HIV reverse transcriptase mutants reported by Kim et al. (*Proc. Natl. Acad. Sci.* (*U.S.A.*), 92:684–688 (1995)). The selected AMV RTX genes are recovered by PCR by using oligonucleotides flanking the cloned gene. The resulting PCR products are subjected to in vitro RSR, selected as described above, and the process is repeated until the level of functional expression is acceptable. Individual clones are then screened for RNA-dependent DNA polymerization and other properties of interest (e.g. half life at room temperature, error rate). The candidate clones are subjected to mutagenesis, and then tested again to yield an AMV RT that can be expressed in *E. coli* at high levels.

2. Evolved Chaperonins

In some embodiments of the invention, overexpression of a protein can lead to the accumulation of folding intermediates which have a tendency to aggregate. Without being limited to any one theory, the role of chaperonins is thought to be to stabilize such folding intermediates against aggregation; thus, overexpression of a protein of interest can lead to overwhelming the capacity of chaperoning. Chaperonin genes can be evolved using the techniques of the invention, either alone or in combination with the genes encoding the protein of interest, to overcome this problem.

Examples of proteins of interest which are especially suited to this approach include but are not limited to: cytokines; malarial coat proteins; T cell receptors; antibodies; industrial enzymes (e.g., detergent proteases and detergent lipases); viral proteins for use in vaccines; and plant seed storage proteins.

Sources of chaperonin genes include but are not limited to *E. coli* chaperonin genes encoding such proteins as thioredoxin, Gro ES/Gro EL, PapD, ClpB, DsbA, DsbB, DnaJ, DnaK, and GrpE; mammalian chaperonins such as Hsp70, Hsp72, Hsp73, Hsp40, Hsp60, Hsp10, Hdj1, TCP-1, Cpn60, BiP; and the homologues of these chaperonin genes in other species such as yeast (J. G. Wall and A. Pluckthun,

*Current Biology*, 6:507–516 (1995); Hartl, *Nature*, 381:571–580 (1996)). Additionally, heterologous genomic or cDNA libraries can be used as libraries to select or screen for novel chaperoning.

In general, evolution of chaperonins is accomplished by first mutagenizing chaperonin genes, screening or selecting for improved expression of the target protein of interest, subjecting the mutated chaperonin genes to RSR, and repeating selection or screening. As with all RSR techniques, this is repeated until the desired improvement of expression of the protein of interest is obtained. Two exemplary approaches are provide below.

a. Chaperonin Evolution in Trans to the Protein of Interest with a Screen or Selection for Improved Function In some embodiments the chaperonin genes are evolved independently of the gene(s) for the protein of interest. The improvement in the evolved chaperonin can be assayed, for example, by screening for enhancement of the activity of the target protein itself or for the activity of a fusion protein comprising the target protein and a selectable or screenable protein (e.g., GFP, alkaline phosphatase or beta-galactosidase).

b. Chaperonin Overon in cis

In some embodiments, the chaperonin genes and the target protein genes are encoded on the same plasmid, but not necessarily evolved together. For example, a lac headpiece dimer can be fused to the protein target to allow for selection of plasmids which encode soluble protein. Chaperonin genes are provided on this same plasmid ("cis") and are shuffled and evolved rather than the target protein. Similarly, the chaperonin genes can be cloned onto a phagemid plasmid that encodes a gene III or gene VIII fusion with a protein of interest. The cloned chaperonins are mutagenized and, as with the selection described above, phage expressing functionally displayed fusion protein are isolated on an affinity matrix. The chaperonin genes from these phage are shuffled and the cycle of selection, mutation and recombination are applied recursively until fusion proteins are efficiently displayed in functional form.

3. Improved Intracellular Localization

Many overexpressed proteins of biotechnological interest are secreted into the periplasm or media to give advantages in purification or activity assays. Optimization for high level secretion is difficult because the process is controlled by many genes and hence optimization may require multiple mutations affecting the expression level and structure of several of these components. Protein secretion in *E. coli*, for example, is known to be influenced by many proteins including: a secretory ATPase (SecA), a translocase complex (SecB, SecD, SecE, SecF, and SecY), chaperonins (DnaK, DnaJ, GroES, GroEL), signal peptidases (LepB, LspA, Ppp), specific folding catalysts (DsbA) and other proteins of less well defined function (e.g., Ffh, FtsY) (Sandkvist et al., *Curr. Op. Biotechnol.* 7:505–511 (1996)). Overproduction of wild type or mutant copies of these genes for these proteins can significantly increase the yield of mature secreted protein. For example, overexpression of secY or secY4 significantly increased the periplasmic yield of mature human IL6 from a hIL6-pre-OmpA fusion (Perez-Perez et al., *Bio-Technology* 12:178–180 (1994)). Analogously, overexpression of DnaK/DnaJ in *E. coli* improved the yield of secreted human granulocyte colony stimulating factor (Perez-Perez et al., *Biochem. Biophys. Res. Commun.* 210:524–529 (1995)).

RSR provides a route to evolution of one or more of the above named components of the secretory pathway. The following strategy is employed to optimize protein secretion in *E. coli*. Variations on this method, suitable for application to *Bacillus subtilis*, Pseudomonas, *Saccaromyces cerevisix*, *Pichia pastoris*, mammalian cells and other hosts are also described. The general protocol is as follows.

One or more of the genes named above are obtained by PCR amplification from *E. coli* genomic DNA using known flanking sequence, and cloned in an ordered array into a plasmid or cosmid vector. These genes do not in general occur naturally in clusters, and hence these will comprise artificial gene clusters. The genes may be cloned under the control of their natural promoter or under the control of another promoter such as the lac, tac, arabinose, or trp promoters. Typically, rare restriction sites such as Sfi I are placed between the genes to facilitate ordered reassembly of shuffled genes as described in the methods of the invention.

The gene cluster is mutagenized and introduced into a host cell in which the gene of interest can be inducibly expressed. Expression of the target gene to be secreted and of the cloned genes is induced by standard methods for the promoter of interest (e.g., addition of 1 mM IPTG for the lac promoter). The efficiency of protein secretion by a library of mutants is measured, for example by the method of colony blotting (Skerra et al., *Anal. Biochem.* 196:151–155 (1991)). Those colonies expressing the highest levels of secreted protein (the top 0.1–10%; preferably the top 1%) are picked. Plasmid DNA is prepared from these colonies and shuffled according to any of the methods of the invention.

Preferably, each individual gene is amplified from the population and subjected to RSR. The fragments are digested with Sfi I (introduced between each gene with nonpalindromic overhangs designed to promote ordered reassembly by DNA ligase) and ligated together, preferably at low dilution to promote formation of covalently closed relaxed circles (<1 ng/microliter). Each of the PCR amplified gene populations may be shuffled prior to reassembly into the final gene cluster. The ligation products are transformed back into the host of interest and the cycle of selection and RSR is repeated.

Analogous strategies can be employed in other hosts such as Pseudomonas, *Bacillus subtilis*, yeast and mammalian cells. The homologs of the *E. coli* genes listed above are targets for optimization, and indeed many of these homologs have been identified in other species (Pugsley, *Microb. Rev.* 57:50–108 (1993)). In addition to these homologs, other components such as the six polypeptides of the signal recognition particle, the trans-locating chain-associating membrane protein (TRAM), BiP, the Ssa proteins and other hsp70 homologs, and prsA (*B. subtilis*) (Simonen and Pulva, *Microb. Rev.* 57:109–137 (1993)) are targets for optimization by RSR. In general, replicating episomal vectors such as SV40-neo (Sambrook et al., *Molecular Cloning*, CSH Press (1987), Northrup et al., *J. Biol. Chem.* 268(4):2917–2923 (1993)) for mammalian cells or 2 micron or ars plasmids for yeast (Strathern et al., *The Molecular Biology of the Yeast Saccaromyces*, CSH Press (1982)) are used. Integrative vectors such as pJM 103, pJM 113 or pSGMU2 are preferred for *B. subtilis* (Perego, Chap. 42, pp. 615–624 in: *Bacillus subtilis and Other Gram-Positive Bacteria*, A. Sonenshein, J. Hoch, and R. Losick, eds., 1993).

For example, an efficiently secreted thermostable DNA polymerase can be evolved, thus allowing the performance of DNA polymerization assays with little or no purification of the expressed DNA polymerase. Such a procedure would be preferred for the expression of libraries of mutants of any protein that one wished to test in a high throughput assay, for example any of the pharmaceutical proteins listed in Table I, or any industrial enzyme. Initial constructs are made by fusing a signal peptide such as that from STII or OmpA to the amino terminus of the protein to be secreted. A gene cluster of cloned genes believed to act in the secretory pathway of interest are mutagenized and coexpressed with the target construct. Individual clones are screened for expresion of the gene product. The secretory gene clusters from improved clones are recovered and recloned and introduced back into the original host. Preferably, they are first subjected to mutagenesis before the process is repeated. This cycle is repeated until the desired improvement in expression of secreted protein is achieved.

IV. Evolved Polyveptide Properties

A. Evolved Transition State Analoa and Substrate Binding

There are many enzymes of industrial interest that have substantially suboptimal activity on the substrate of interest. In many of these cases, the enzyme obtained from nature is required to work either under conditions that are very different from the conditions under which it evolved or to have activity towards a substrate that is different from the natural substrate.

The application of evolutionary technologies to industrial enzymes is often significantly limited by the types of selections that can be applied and the modest numbers of mutants that can be surveyed in screens. Selection of enzymes or catalytic antibodies, expressed in a display format, for binding to transition state analogs (McCafferty et al., *Appl. Biochem. Biotechnol.* 47:157–173 (1994)) or substrate analogs (Janda et al., *Proc. Natl. Acad. Sci. (U.S.A.)* 91:2532–2536, (1994)) represnts a general strategy for selecting for mutants with with improved catalytic efficiency.

Phage display (O'Neil et al., *Current Biology* 5:443–449 (1995) and the other display formats (Gates et al., *J. Mol. Biol.* 255:373–386 (1995); Mattheakis et al., *Proc. Natl. Acad. Sci. (U.S.A.)* 91:9022–9026 (1994)) described herein represent general methodologies for applying affinity-based selections to proteins of interest. For example, Matthews and Wells (*Science* 260:1113–1117 (1993)) have used phage display of a protease substrate to select improved substrates. Display of active enzymes on the surface of phage, on the other hand, allows selection of mutant proteins with improved transition state analog binding. Improvements in affinity for transition state analogs correlate with improvements in catalytic efficiency. For example, Patten et al., *Science* 271:1086–1091 (1996) have shown that improvements in affinity of a catalytic antibody for its hapten are well correlated with improvements in catalytic efficiency, with an 80–fold improvement in kcat/Km being achieved for an esterolytic antibody.

For example, an enzyme used in antibiotic biosynthesis can be evolved for new substrate specificity and activity under desired conditions using phage display selections. Some antibiotics are currently made by chemical modifications of biologically produced starting compounds. Complete biosynthesis of the desired molecules is currently impractical because of the lack of an enzyme with the required enzymatic activity and substrate specificity (Skatrud, *TIBTECH* 10:324–329, September 1992). For example, 7-aminodeacetooxycephalosporanic acid (7-ADCA) is a precursor for semi-synthetically produced cephalosporins. 7-ADCA is made by a chemical ring expansion of penicillin G followed by enzymatic deacylation of the phenoxyacetal group. 7-ADCA can be made enzymatically from deacetylcephalosporin C (DAOC V), which could in turn be derived from penicillin V by enzymatic ring expansion if a suitably modified penicillin expandase could be evolved (Cantwell et al., *Curr. Genet.* 17:213–221 (1990)). Thus, 7-ADCA could in principle be produced enzymatically from penicillin V using a modified penicillin N expandase, such as mutant forms of the *S. clavuligerus* cefE gene (Skatrud, *TIBTECH* 10:324–329, September 1992). However, penicillin V is not accepted as a substrate by any known expandase with sufficient efficiency to be commercially useful. As outlined below, RSR techniques of the invention can be used to evolve the penicillin expandase encoded by cefE or other expandases so that they will use penicillin V as a substrate.

Phage display or other display format selections are applied to this problem by expressing libraries of cefE penicillin expandase mutants in a display format, selecting for binding to substrates or transition state analogs, and applying RSR to rapidly evolve high affinity binders. Candidates are further screened to identify mutants with improved enzymatic activity on penicillin V under desired reaction conditions, such as pH, temperature, solvent concentration, etc. RSR is applied to further evolve mutants with the desired expandase activity. A number of transition state analogs (TSA's) are suitable for this reaction. The following structure is the initial TSA that is used for selection of the display library of cefE mutants:

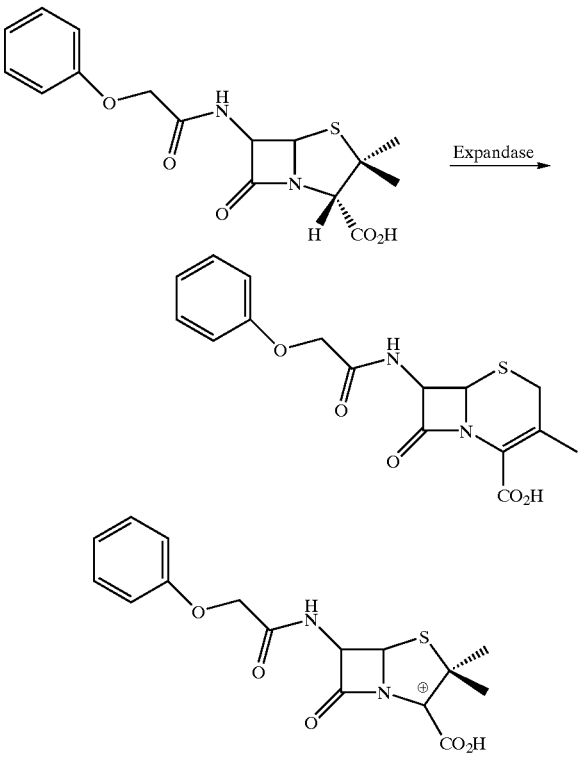

Libraries of the known penicillin expandases (Skatrud, *TIBTECH* 10:324–329(1992); Cantwell et al., *Curr. Genet.* 17:13–221 (1990)) are made as described herein. The display library is subjected to selection for binding to penicillin V and/or to transition state analog given above for the conversion of penicillin V to DAOC V. These binding selections may be performed under non-physiological reaction conditions, such as elevated temperature, to obtain mutants that are active under the new conditions. RSR is applied to evolve mutants with $2-10^5$ fold improvement in binding affinity for the selecting ligand. When the desired level of improved binding has been obtained, candidate mutants are expressed in a high throughput format and specific activity for expanding penicillin V to DAOC V is quantitatively measured. Recombinants with improved enzymatic activity are mutagenized and the process repeated to further evolve them.

Retention of TSA binding by a displayed enzyme (e.g., phage display, lac headpiece dimer, polysome display, etc.) is a good selection for retention of the overall integrity of the active site and hence can be exploited to select for mutants which retain activity under conditions of interest. Such conditions include but are not limited to: different pH optima, broader pH optima, activity in altered solvents such as DMSO (Seto et al., *DNA Sequence* 5:131–140 (1995)) or formamide (Chen et al., *Proc. Natl. Acad. Sci. (U.S.A.)* 90:5618–5622, (1993)) altered temperature, improved shelf life, altered or broadened substrate specificity, or protease resistance. A further example, the evolution of a p-nitrophenyl esterase, using a mammalian display format, is provided below.

B. Improvement of DNA and RNA Polymerases

Of particular commercial importance are improved polymerases for use in nucleic acid sequencing and polymerase chain reactions. The following properties are attractive candidates for improvement of a DNA sequencing polymerase: (1) suppression of termination by inosine in labelled primer format (H. Dierick et al., *Nucleic Acids Res.* 21:4427–4428 (1993)) (2) more normalized peak heights, especially with fluorescently labelled dideoxy terminators (Parker et al., *BioTechniques* 19:116–121 (1995)), (3) better sequencing of high GC content DNA (>60% GC) by, for example, tolerating >10% DMSO (D. Seto et al., *DNA Sequence* 5:131–140 (1995); Scheidl et al., *BioTechniques* 19(5) :691–694 (1995)), or (4) improved acceptance of novel base analogs such as inosine, 7-deaza dGTP (Dierick et al., *Nucleic Acids Res.* 21:4427–4428 (1993)) or other novel base analogs that improve the above properties.

Novel sequencing formats have been described which use matrix assisted laser desorption ionization time of flight (MALDT-TOF) mass spectroscopy to resolve dideoxy ladders (Smith, *Nature Biotechnology* 14:1084–1085 (1996)). It is noted in Smith's recent review that fragmentation of the DNA is the singular feature limiting the development of this method as a viable alternative to standard gel electrophoresis for DNA sequencing. Base analogs which stabilize the N-glycosidic bond by modifications of the purine bases to 7-deaza analogs (Kirpekar et al., *Rapid Comm. in Mass Spec.* 9:525–531 (1995)) or of the 2' hydroxyl (such as 2'-H or 2'-F) "relieve greatly the mass range limitation" of this technique (Smith, 1996). Thus, evolved polymerases that can efficiently incorporate these and other base analogs conferring resistance to fragmentation under MALDI-TOF conditions are valuable innovations.

Other polymerase properties of interest for improvement by RSR are low fidelity thermostable DNA polymerase for more efficient mutagenesis or as a useful correlate for acceptance of base analogs for the purposes described above; higher fidelity polymerase for PCR (Lundberg et al., *Gene* 108:1–6 (1991)); higher fidelity reverse transcriptase for retroviral gene therapy vehicles to reduce mutation of the therapeutic construct and of the retrovirus; improved PCR of GC rich DNA and PCR with modified bases (S. Turner and F. J. Jenkins, *BioTechniques* 19(1):48–52 (1995)).

Thus, in some embodiments of the invention, libraries of mutant polymerase genes are screened by direct high throughput screening for improved sequencing properties. The best candidates are then subjected to RSR. Briefly, mutant libraries of candidate polymerases such as Taq polymerase are constructed using standard methods such as PCR mutagenesis (Cadwell et al., *PCR Meth. ADP.* 2:28–33 (1992)) and/or cassette mutagenesis (Sambrook et al., Molecular Cloning, CSH Press (1987)). Incorporation of mutations into Taq DNA polymerase such as the active site residue from T7 polymerase that improves acceptance of dideoxy nucleotides (Tabor and Richardson, *J. Biol. Chem.* 265:8322–8328 (1990)) and mutations that inactivate the 5'—3' exonuclease activity (R. S. Ranu, *BioTechniaues* 18:390–396 (1995)) are incorporated into these libraries. The reassembly PCR technique, for example, as described above is especially suitable for this problem. Similarly, chimeric polymerase libraries are made by breeding existing thermophilic polymerases, sequenase, and *E. coli* polI with each other using the bridge oligonucleotide methods described above. The libraries are expressed in formats wherein human or robotic colony picking is used to replica pick individual colonies urn into 96 well plates where small cultures are grown, and polymerase Oexpression is induced.

A high throughput, small scale simple purification for polymerase expressed in each well is performed. For example, simple single-step purifications of His-tagged Taq expressed in *E. coli* have been described (Smirnov et al., *Russian J. Bioorganic Chem.* 21(5):341–342 (1995)), and could readily be adapted for a 96-well expression and purification format.

A high throughput sequencing assay is used to perform sequencing reactions with the purified samples. The data is analyzed to identify mutants with improved sequencing properties, according to any of these criteria: higher quality ladders on GC-rich templates, especially greater than 60% GC, including such points as fewer artifactual termination products and stronger signals than given with the wild-type enzyme; less termination of reactions by inosine in primer labelled reactions, e.g., fluorescent labelled primers; less variation in incorporation of signals in reactions with fluorescent dideoxy nucleotides at any given position; longer sequencing ladders than obtained with the wild-type enzyme, such as about 20 to 100 nucleotides; improved acceptance of other known base analogs such as 7-deaza purines; improved acceptance of new base analogs from combinatorial chemistry libraries (See, for example, Hogan, *Nature* 384(Supp):17–(1996).

The best candidates are then subjected to mutagenesis, and then selected or screened for the improved sequencing properties decribed above.

In another embodiment, a screen or selection is performed as follows. The replication of a plasmid can be placed under obligate control of a polymerase expressed in *E. coli* or another microorganism. The effectiveness of this system has been demonstrated for making plasmid replication dependent on mammalian polymerase beta (Sweasy et al., *Proc. Natl. Acad. Sci. (U.S.A.)* 90:4626–4630, (1993)), Taq polymerase (Suzuki et al., *Proc. Natl. Acad. Sci. (U.S.A.)* 93:9670–9675 (1996)), or HIV reverse transcriptase (Kim et al., *Proc. Natl. Acad. Sci. (U.S.A.)* 92:684–688 (1995)). The mutant polymerase gene is placed on a plasmid bearing a colE1 origin and expressed under the control of an arabinose promoter. The library is enriched for active polymerases essentially as described by Suzuki et al., (supra), with polymerase expression being induced by the presence of arabinose in the culture.

A further quantitative screen utilizes the presence of GFP (green fluorescence protein) on the same plasmid, replica plating onto arabinose at the nonpermissive temperature in the absence of a selective antibiotic, and using a fluorimeter to quantitatively measure fluorescence of each culture. GFP activity correlates with plasmid stability and copy number which is in turn dependent on expression of active polymerase.

A polymerase with a very high error rate would be a superior sequencing enzyme, as it would have a more normalized signal for incorporation of base analogs such as the currently used fluorescently labelled dideoxies because it will have reduced specificity and selectivity. The error rates of currently used polymerases are on the order of $10^{-5}$ to $10^{-6}$, orders of magnitude lower than what can be detected given the resolving power of the gel systems. An error rate of 1%, and possibly as high as 10%, could not be detected by current gel systems, and thus there is a large window of opportunity to increase the "sloppiness" of the enzyme. An error-prone cycling polymerase would have other uses such as for hypermutagenesis of genes by PCR.

In some embodiments, the system described by Suzuki (Suzuki et al., *Proc. Natl. Acad. Sci.* (*U.S.A.*) 96:9670–9675 (1996)) is used to make replication of a reporter plasmid dependent on the expressed polymerase. This system puts replication of the first 200–300 bases next to the ColE1 origin directly under the control of the expressed polymerase (Sweasy and Loeb, *J. Bact.* 177:2923–2925 (1995); Sweasy et al., *Proc. Natl. Acad. Sci.* (*U.S.A.*) 90:4626–4630 (1993)). A screenable or selectable reporter gene containing stop codons is positioned in this region, such as LacZ alpha containing one, two or three stop codons. The constructs are grown on arabinose at the nonpermissible temperature, allowed to recover, and plated on selective lactose minimal media that demands reversion of the stop codons in the reporter cassette. Mutant polymerases are recovered from the survivors by PCR. The survivors are enriched for mutators because their mutator phenotype increases the rate of reversion of stop codons in the reporter lacZ alpha fragment.

The polymerase genes from the survivors are subjected to RSR, then the polymerase mutants are retransformed into the indicator strain. Mutators can be visually screened by plating on arabinose/Xgal plates at the nonpermissive temperature. Mutator polymerases will give rise to colonies with a high frequency of blue papillae due to reversion of the stop codon(s). Candidate papillators can be rescreened by picking a non-papillating region of the most heavily papillated colonies (i.e, "best" colonies) and replating on the arabinose/ Xgal indicator medium to further screen for colonies with increased papillation rates. These steps are repeated until a desired reversion rate is achieved (e.g., $10^{-2}$ to $10^{-3}$ mutations per base pair per replication).

Colonies which exhibit high frequency papillation are candidates for encoding an error prone polymerase. These candidates are screened for improved sequencing properties essentially as for the high throughput screen described above. Briefly, mutant Taq proteins are expressed and purified in a 96-well format. The purified proteins are used in sequencing reactions and the sequence data are analyzed to identify mutants that exhibit the improvements outlined herein. Mutants with improved properties are subjected to RSR and rescreened for further improvements in function.

In some embodiments, GFP containing stop codons instead of lacz alpha with stop codons is used for the construction. Cells with reverted stop codons in GFP are selected by fluorescence activated cell sorter (FACS). In general, FACS selection is performed by gating the brightest about 0.1–10%, preferably the top 0.1 to 1%, and collected according to a protocol similar to that of Dangl et al., (*Cytometry* 2(6):395–401 (1982)). In other embodiments, the polA gene is flanked with lox sites or other targets of a site specific recombinase. The recombinase is induced, thus allowing one to inducibly delete the polA gene (Medberry et al., *Nucleic Acid Res.* 23:485–490 (1995)). This would allow one to perform "Loeb-type" selections at any temperature and in any host. For example, one could set up such a selection in a recA deficient mesophile or thermophile by placing the polA homologue in an inducibly deletable format and thus apply the selection for active polymerase under more general conditions.

In further embodiments, this general system is preferred for directed in vivo mutagenesis of genes. The target gene is cloned into the region near a plasmid origin of replication that puts its replication obligately under control of the error prone polymerase. The construct is passaged through a polA(ts) recA strain and grown at the nonpermissive temperature, thus specifically mutagenizing the target gene while replicating the rest of the plasmid with high fidelity.

In other embodiments, selection is based on the ability of mutant DNA polymerases to PCR amplify DNA under altered conditions or by utilizing base analogs. The mutant polymerases act on the template that encodes them in a PCR amplification, thus differentially replicating those polymerases.

In brief, an initial library of mutants is replica plated. Polymerase preparations are done in a 96-well format. Crude plasmid preparations are made of the same set. Each plasmid prep is PCR-amplified using the polymerase prep derived from that plasmid under the conditions for which one wishes to optimize the polymerase (e.g., added DMSO or formamide, altered temperature of denaturation or extension, altered buffer salts, PCR with base analogs such a-thiol dNTP's for use with mass spectroscopy sequencing, PCR of GC rich DNA (>60% GC),PCR with novel base analogs such as 7-deaza purines, 2' fluoro dNTP's, rNTP's, PCR with inosine, etc.). The amplified genes are pooled, cloned,and subjected to mutagenesis, and the process repeated until an improvement is achieved.

C. Evolved Phosphonatase

Alkaline phosphatase is a widely used reporter enzyme for ELISA assays, protein fusion assays, and in a secreted form as a reporter gene for mammalian cells. The chemical lability of p-nitrophenyl phosphate (pNPP) substrates and the existence of cellular phosphatases that cross-react with pNPP is an important limitation on the sensitivity of assays using this reporter gene. A reporter gene with superior signal to noise properties can be developed based on hydrolysis of p-nitrophenyl phosphonates, which are far more stable to base catalyzed hydrolysis than the corresponding phosphates. Additionally, there are far fewer naturally occurring cellular phosphonatases than alkaline phosphatases. Thus a p-nitrophenyl phosphonatase is an attractive replacement for alkaline phosphatase because the background due to chemical and enzymatic hydrolysis is much lower. This will allow one to make ELISA's more sensitive for detecting very small concentrations of antigen.

Chen et al. (*J. Mol. Biol.* 234:165–178 (1993)) have shown that a *Staph. aureus* beta-lactamase can hydrolyze p-nitrophenyl phosphonate esters with single turnover kinetics. The active site Ser70 (the active site nucleophile for beta lactam hydrolysis) forms a covalent intermediate with the substrate. This is analogous to the first step in hydrolysis of beta lactams, and this enzyme can be evolved by RSR to hydrolyze phosphonates by a mechanism analogous to beta lactam hydrolysis. Metcalf and Wanner have described a cryptic phosphonate utilizing operon (phn) in *E. coli*, and have constructed strains bearing deletions of the phn operon (*J. Bact.* 175:3430–3442 (1993)). This paper discloses selections for growth of *E. coli* on phosphate free minimal media where the phosphorous is derived from hydrolysis of alkyl phosphonates by genes in the phn operon. Thus, one could select for evolved p-nitrophenyl phosphonatases that are active using biochemical selections on defined minimal media. Specifically, an efficient phosphonatase is evolved as follows. A library of mutants of the Staph. aureus beta lactamase or of one of the E. coli phn enzymes is constructed. The library is transformed into E. coli mutants wherein the phn operon has been deleted, and selected for growth on phosphate free MOPS minimal media containing p-nitrophenyl phosphonate. RSR is applied to selected mutants to further evolve the enzyme for improved hydrolysis of p-nitrophenyl phosphonates.

D. Evolved Deterrent Proteases

Proteases and lipases are added in large quantities to detergents to enzymatically degrade protein and lipid stains on clothes. The incorporation of these enzymes into detergents has significantly reduced the need for surfactants in detergents with a consequent reduction in the cost of formulation of detergents and improvement in stain removal properties. Proteases with improved specific activity, improved range of protein substrate specificity, improved shelf life, improved stability at elevated temperature, and reduced requirements for surfactants would add value to these products.

As an example, subtilisin can be evolved as follows. The cloned subtilisin gene (von der Osten et al., *J. Biotechnol.* 28:55–68 (1993)) can be subjected to RSR using growth selections on complex protein media by virtue of secreted subtilisin degrading the complex protein mixture. More specifically, libraries of subtilisin mutants are constructed in an expression vector which directs the mutant protein to be secreted by *Bacillus subtilus*. Bacillus hosts transformed with the libraries are grown in minimal media with complex protein formulation as carbon and/or nitrogen source. Subtilisin genes are recovered from fast growers and subjected to RSR, then screened for improvement in a desired property.

E. Escape of Phage from a "Protein Net"

In some embodiments, selection for improved proteases is performed as follows. A library of mutant protease genes is constructed on a display phage and the phage grown in a multiwell format or on plates. The phage are overlayed with a "protein net" which ensnares the phage. The net can consist of a protein or proteins engineered with surface disulphides and then crosslinked with a library of peptide linkers. A further embodiment employs an auxiliary matrix to further trap the phage. The phage are further incubated, then washed to collect liberated phage wherein the displayed protease was able to liberate the phage from the protein net. The protease genes are then subjected to RSR for further evolution. A further embodiment employs a library of proteases encoded by but not displayed on a phagemid wherein streptavidin is fused to pIII by a peptide linker. The library of protease mutants is evolved to cleave the linker by selecting phagemids on a biotin column between rounds of amplification.

In a further embodiment, the protease is not necessarily provided in a display format. The host cells secrete the protease encoded by but not surface diplayed by a phagemid, while constrained to a well, for example, in a microtiter plate. Phage display format is preferred where an entire high titre lysate is encased in a protein net matrix, and the phage expressing active and broad specificity proteases digesting the matrix to be liberated for the next round of amplification, mutagenesis, and selection.

In a further embodiment, the phage are not constrained to a well but, rather, protein binding filters are used to make a colony of plaque lifts and are screened for activity with chromogenic or fluorogenic substrates. Colonies or plaques corresponding to positive spots on the filters are picked and the encoded protease genes are recovered by, for example, PCR. The protease genes are then subjected to RSR for further evolution.

F. Screens for Improved Protease Activity

Peptide substrates containing fluorophores attached to the carboxy terminus and fluorescence quenching moieties on the amino terminus, such as those described by Holskin, et al, (*Anal. Biochem.* 227:148–55 (1995)) (e.g., (4-4'-dimethylaminophenazo)benzoyl-arg-gly-val-val-asn-ala-ser-ser-arg-leu-ala-5-(2'-aminoethyl)-amino]-naphthalene-1-sulfonic acid) (SEQ ID NO. 99) are used to screen protease mutants for broadened or altered specificity. In brief, a library of peptide substrates is designed with a fluorophore on the amino terminus and a potent fluorescence quencher on the carboxy terminus, or vice versa. Supernatants containing secreted proteases are incubated either separately with various members of the library or with a complex cocktail. Those proteases which are highly active and have broad specificity will cleave the majority of the peptides, thus releasing the fluorophore from the quencher and giving a positive signal on a fluorimeter. This technique is amenable to a high density multiwell format.

G. Improving pharmaceutical proteins using RSR

Table I lists proteins that are of particular commercial interest to the pharmaceutical industry. These proteins are all candidates for RSR evolution to improve function, such as ligand binding, shelf life, reduction of side effects through enhanced specificity, etc. All are well-suited to manipulation by the techniques of the invention. Additional embodiments especially applicable to this list are described below.

First, high throughput methods for expressing and purifying libraries of mutant proteins, similar to the methods described above for Taq polymerase, are applied to the proteins of Table I. These mutants are screened for activity in a functional assay. For example, mutants of IL2 are screened for resistance to plasma or tissue proteases with retention of activity for the low affinity IL2 receptor but with loss of activity on the high affinity IL2 receptor. The genes from mutants with improved activity relative to wild-type are recovered, and subjected to RSR to improve the phenotype further.

Preferably, the libraries are generated in a display format such that the mature folded protein is physically linked to the genetic information that encodes it. Examples include phage display using filamentous phage (O'Neil et al., *Current Biology* 5:443–449 (1995)) or bacteriophage lambda gene V display (Dunn, *J. Mol. Biol.* 248:497–506 (1995)), peptides on plasmids (Gates et al., *J. Mol. Biol.* 255:373–386 (1995)) where the polypeptide of interest is fused to a lac headpiece dimer and the nascent translation product binds to a lac operator site encoded on the plasmid or PCR product, and polysome display (Mattheakis et al., *Proc. Natl. Acad. Sci. (U.S.A.)* 91:9022–9026 (1994)) where ribosomes are stalled on mRNA molecules such that the nascent polypeptide is exposed for interaction with cognate ligands without disrupting the stalled ribosome/mRNA complex. Selected complexes are subjected to RT-PCR to recover the genes.

When so displayed, affinity binding of the recombinant phage is often done using a receptor for the protein of interest. In some cases it is impractical to obtain purified receptor with retention of all desired biological characteristics (for example, 7-transmembrane (7-TM) receptors). In such cases, one could use cells expressing the receptor as the panning substrate. For example, Barry et al. (*Nat. Med.* 2:299–305 (1996)) have described successful panning of M13 libraries against whole cells to obtain phage that bind to the cells expressing a receptor of interest. This format could be generally applied to any of the proteins listed in Table I.

In some embodiments, the following method can be used for selection. A lysate of phage encoding IFN alpha mutants, for example, can be used directly at suitable dilution to stimulate cells with a GFP reporter construct (Crameri et al., *Nat. Biotech.* 14:315–319 (1996)) under the control of an IFN responsive promoter, such as an MHC class I promoter. Phage remaining attached after stimulation, expression and FACS purification of the responsive cells, can be purified by FACS. Preferably, the brightest cells are collected. The phage are collected and their DNA subjected to RSR until the level of desired improvement is achieved.

Thus, for example, IL-3 is prepared in one of these display formats and subjected to RSR to evolve an agonist with a desired level of activity. A library of IL3 mutants on a filamentous phage vector is created and affinity selected ("panned") against purified IL3 receptor to obtain mutants with improved affinity. The mutant IL-3 genes are recovered by PCR, subjected to RSR, and recloned into the display vector. The cycle is repeated until the desired affinity or agonist activity is achieved.

Many proteins of interest are expressed as dimers or higher order multimeric forms. In some embodiments, the display formats descibed above preferentially are applied to a single chain version of the protein. Mutagenesis, such as RSR, can be used in these display formats to evolve improved single chain derivatives of multimeric factors which initially have low but detectable activity. This strategy is described in more detail below.

H. Whole Cell Selections

In some embodiments, the eukaryotic cell is the unit of biological selection. The following general protocol can be used to apply RSR to the improvement of proteins using eukaryotic cells as the unit of selection: (1) transfection of libraries of mutants into a suitable host cell, (2) expression of the encoded gene product(s) either transiently or stably, (3) functional selection for cells with an improved phenotype (expression of a receptor with improved affinity for a target ligand; viral resistance, etc., (4) recovery of the mutant genes by, for example, PCR followed by preparation of HIRT supernatants with subsequent tranformation of *E. coli*, (5) RSR and (6) repetition of steps (1)–(5) until the desired degree of improvement is achieved.

For example, previous work has shown that one can use mammalian surface display to functionally select cells expressing cloned genes, such as using an antibody to clone the gene for an expressed surface protein (Reviewed by Seed, *Curr. Opin. Biotechnol.* 6:567–573 (1995)). Briefly, cells are transiently transfected with libraries of cloned genes residing on replicating episomal vectors. An antibody directed against the protein of interest (whose gene one wishes to clone) is immobilized on a solid surface such as a plastic dish, and the transfected cells expressing the protein of interest are affinity selected.

For example, the affinity of an antibody for a ligand can be improved using mammalian surface display and RSR. Antibodies with higher affinity for their cognate ligands are then screened for improvement of one or more of the following properties: (1) improved therapeutic properties (increased cell killing, neutralization of ligands, activation of signal transduction pathways by crosslinking receptors), (2) improved in vivo imaging applications (detection of the antibody by covalent/noncovalent binding of a radionuclide or any agent detectable outside of the body by noninvasive means, such as NMR), (3) improved analytical applications (ELISA detection of proteins or small molecules), and (4) improved catalysts (catalytic antibodies). The methods described are general and can be extended to any receptor-ligand pair of interest. A specific example is provided in the experimental section.

The use of a one mutant sequence-one transfected cell protocol is a preferred design feature for RSR based protocols because the point is to use functional selection to identify mutants with improved phenotypes and, if the transfection is not done in a "clonal" fashion, the functional phenotype of any given cell is the result of the sum of many transfected sequences. Protoplast fusion is one method to achieve this end, since each protoplast contains typically greater than 50 copies each of a single plasmid variant. However, it is a relatively low efficiency process (about $10^3$–$10^4$ transfectants), and it does not work well on some non-adherent cell lines such as B cell lines. Retroviral vectors provide a second alternative, but they are limited in the size of acceptable insert (>10 kb) and consistent, high expression levels are sometimes difficult to achieve. Random integration results in varying expression levels, thus introducing noise and limiting one's ability to distinguish between improvements in the affinity of the mutant protein vs. increased expression. A related class of strategies that can be used effectively to achieve "one gene-one cell" DNA transfer and consistent expression levels for RSR is to use a viral vector which contains a lox site and to introduce this into a host that expresses cre recombinase, preferably transiently, and contains one or more lox sites integrated into its genome, thus limiting the variability of integration sites (Rohlman et al. *Nature Biotech.* 14:1562–1565 (1996)).

An alternative strategy is to transfect with limiting concentrations of plasmid (i.e., about one copy per cell) using a vector that can replicate in the target cells, such as is the case with plasmids bearing SV40 origins transfected into COS cells. This strategy requires that either the host cell or the vector supply a replication factor such as SV40 large T antigen. Northrup et al. (*J. Biol. Chem.* 268:2917–2923 (1993)) describe a strategy wherein a stable transfectant expressing SV40 large T antigen is then transfected with vectors bearing SV40 origins. This format gave consistently higher transient expression and demonstrable plasmid replication, as assayed by sensitivity to digestion by Dpn I. Transient expression (i.e, non-integrating plasmids) is a preferred format for cellular display selections because it reduces the cycle time and increases the number of mutants that can be screened.

The expression of SV40 large T antigen or other replication factors may have deleterious effects on or may work inefficiently in some cells. In such cases, RSR is applied to the replication factor itself to evolve mutants with improved activity in the cell type of interest. A generic protocol for evolving such a factor is as follows:

The target cell is transfected with GFP cloned onto a vector containing SV40 large T antigen, an SV40 origin, and a reporter gene such as GFP; a related format is cotransfection with limiting amounts of the SV40 large T antigen expression vector and an excess of a reporter such as GFP cloned onto an SV40 origin containing plasmid. Typically after 1–10 days of transient expression, the brightest cells are purified by FACS. SV40 large T antigen mutants are recovered by PCR, and subjected to mutagenesis. The cycle is repeated until the desired level of improvement is obtained.

I. Autocrine Selection

In some embodiments, mutant proteins are selected or screened based on their ability to exert a biological effect in an autocrine fashion on the cell expressing the mutant protein. For example, a library of alpha interferon genes can be selected for induction of more potent or more specific antiviral activity as follows. A library of interferon alpha mutants is generated in a vector which allows for induction of expression (i.e. under control of a metallothionein promoter) and efficient secretion in a multiwell format (96-well for example) with one or a few independent clones per well. In some embodiments, the promoter is not inducible,and may be constitutive.

Expression of the cloned interferon genes is induced. The cells are challenged with a cytotoxic virus against which one wishes to evolve an optimized interferon (for example vesicular stomatitis virus or HIV). Surviving cells are recovered. The cloned interferon genes are recovered by PCR amplification, subjected to RSR, and cloned back into the transfection vector and retransfected into the host cells. These steps are repeated until the desired level of antiviral activity is evolved.

In some embodiments, the virus of interest is not strongly cytotoxic. In this case a conditionally lethal gene, such as herpes simplex virus thymidine kinase, is cloned into the virus and after challenge with virus and recovery, conditionally lethal selective conditions are applied to kill cells that are infected with virus. An example of a conditionally lethal gene is herpes TK, which becomes lethal upon treating cells expressing this gene with the thymidine analog acyclovir. In some embodiments, the antiproliferative activity of the cloned interferons is selected by treating the cells with agents that kill dividing cells (for example, DNA alkylating agents).

In some embodiments, potent cytokines are selected by expressing and secreting a library of cytokines in cells that have GFP or another reporter under control of a promoter that is induced by the cytokine, such as the MHC class I promoter being induced by evolved variants of alpha interferon. The signal transduction pathway is configured such that the wild type cytokine to be evolved gives a weak but detectable signal.

In some embodiments of the invention, proteins are evolved by RSR to have improved half life in serum. A preferred method for improving half-life is evolving the affinity of a protein of interest for a long lived serum protein, such as an antibody or other abundant serum protein. Examples of how affinity for an antibody can enhance serum half life include the co-administration of IL2 and anti-IL2 antibodies which increases serum half-life and anti-tumor activity of human recombinant IL2 (Courtney et al., *Immunopharmacology* 28:223–232 (1994)).

The eight most abundant human serum proteins are serum albumin, immunoglobulins, lipoproteins, haptoglobin, fibrinogen, transferrin, alpha-1 antitrypsin, and alpha-2 macroglobulin (Doolittle, chapter 6, *The Plasma Proteins* F. Putnam, ed.; Academic Press, 1984). These and other abundant serum proteins such as ceruloplasmin and fibronectin are the primary targets against which to evolve binding sites on therapeutic proteins such as in Table I for the purpose of extending half-life. In the case of antibodies, the preferred strategy is to evolve affinity for constant regions rather than variable regions in order to minimize individual variation in the concentration of the relevant target epitope (antibody V region usage between different individuals is significantly variable).

Binding sites of the desired affinity are evolved by applying phage display, peptides on plasmid display or polysome display selections to the protein of interest. One could either mutagenize an existing binding site or otherwise defined region of the target protein, or append a peptide library to the N terminus, C terminus, or internally as a functionally nondisruptive loop.

In other embodiments of the invention, half life is improved by derivatization with PEG, other polymer conjugates or half-life extending chemical moieties. These are established methods for extending half-life of therapeutic proteins (R. Duncan, *Clin. Pharmacokinet* 27:290–306 (1994); Smith et al., *TIBTECH* 11 397–403 (1993)) and can have the added benefit of reducing immunogenicity (R. Duncan, *Clin. Pharmacokinet* 27:290–306 (1994)). However, derivatization can also result in reduced affinity of the therapeutic protein for its receptor or ligand. RSR is used to discover alternative sites in the primary sequence that can be substituted with lysine or other appropriate residues for chemical or enzymatic conjugation with half-life extending chemical moieties, and which result in proteins with maximal retention of biological activity.

A preferred strategy is to express a library of mutants of the protein in a display format, derivatize the library with the agent of interest (i.e. PEG) using chemistry that does not biologically inactivate the display system, select based on affinity for the cognate receptor, PCR amplify the genes encoding the selected mutants, shuffle, reassemble, reclone into the display format, and iterate until a mutant with the desired activity post modification is obtained. An alternative format is to express, purify and derivatize the mutants in a high throughput format, screen for mutants with optimized activity, recover the corresponding genes, subject the genes to RSR and repeat.

In further embodiments of the invention, binding sites for target human proteins that are localized in particular tissues of interest are evolved by RSR. For example, an interferon that localizes efficiently to the liver can be engineered to contain a binding site for a liver surface protein such as hepatocyte growth factor receptor. Analogously, one could evolve affinity for abundant epitopes on erythrocytes such as ABO blood antigens to localize a given protein to the blood stream.

In further embodiments of the invention, the protein of interest is evolved to have increased stability to proteases. For example, the clinical use of IL2 is limited by serious side effects that are related to the need to administer high doses. High doses are required due to the short half life (3–5 min, Lotze et al., *JAMA* 256(22):3117–3124 (1986)) and the consequent need for high doses to maintain a therapeutic level of IL2. One of the factors contributing to short half-lives of therapeutic proteins is proteolysis by serum proteases. Cathepsin D, a major renal acid protease, is responsible for the degradation of IL2 in Balb/c mice (Ohnishi et al., *cancer Res.* 50:1107–1112 (1990)). Furthermore, Ohnishi showed that treatment of Balb/c mice with pepstatin, a potent inhibitor of this protease, prolongs the half life of recombinant human IL2 and augments lymphokine-activated killer cell activity in this mouse model.

Thus, evolution of protease resistant variants of IL2 or any of the proteins listed in Table I that are resistant to serum or kidney proteases is a preferred strategy for obtaining variants with extended serum half lives.

A preferred protocol is as follows. A library of the mutagenized protein of interest is expressed in a display system with a gene-distal epitope tag (i.e. on the N-terminus of a phage display construct such that if it is cleaved off by proteases, the epitope tag is lost). The expressed proteins are treated with defined proteases or with complex cocktails such as whole human serum. Affinity selection with an antibody to the gene distal tag is performed. A second selection demanding biological function (e.g., binding to cognate receptor) is performed. Phage retaining the epitope tag (and hence protease resistant) are recovered and subjected to RSR. The process is repeated until the desired level of resistance is attained.

In other embodiments, the procedure is performed in a screening format wherein mutant proteins are expressed and purified in a high throughput format and screened for protease resistance with retention of biological activity.

In further embodiments of the invention, the protein of interest is evolved to have increased shelf life. A library of the mutagenized nucleic acid squence encoding the protein of interest is expressed in a display format or high throughput expression format, and exposed for various lengths of time to conditions for which one wants to evolve stability (heat, metal ions, nonphysiological pH of, for example, <6 or >8, lyophilization, freeze-thawing). Genes are recovered from from survivors, for example, by PCR. The DNA is subjected to mutagenesis, such as RSR, and the process repeated until the desired level of improvement is achieved.

K. Evolved Single Chain Versions of Multisubunit Factors

As discussed above, in some embodiments of the invention, the substrate for evolution by RSR is preferably a single chain contruction. The possibility of performing asymetric mutagenesis on constructs of homomultimeric proteins provides important new pathways for further evolution of such constructs that is not open to the proteins in their natural homomultimeric states. In particular, a given mutation in a homomultimer will result in that change being present in each identical subunit. In single chain constructs, however, the domains can mutate independently of each other.

Conversion of multisubunit proteins to single chain constructs with new and useful properties has been demonstrated for a number of proteins. Most notably, antibody heavy and light chain variable domains have been linked into single chain Fv's (Bird et al., *Science* 242:423–426 (1988)), and this strategy has resulted in antibodies with improved thermal stability (Young et al., *FEBS Lett* 377:135–139 (1995)), or sensitivity to proteolysis (Solar et al., *Prot. Eng.* 8:717–723 (1995)). A functional single chain version of IL5, a homodimer, has been constructed, shown to have affinity for the IL5 receptor similar to that of wild type protein, and this construct has been used to perform assymetric mutagenesis of the dimer (Li et al., *J. Biol. Chem.* 271:1817–1820 (1996)). A single chain version of urokinase-type plasminogen activator has been made, and it has been shown that the single chain construct is more resistant to plasminogen activator inhibitor type 1 than the native homodimer (Higazi et al., *Blood* 87:354 5–3549 (1996)). Finally, a single-chain insulin-like growth factor I/insulin hybrid has been constructed and shown to have higher affinity for chimeric insulin/IGF-1 receptors than that of either natural ligand (Kristensen et al., *Biochem. J.* 305:981–986 (1995)).

In general, a linker is constructed which joins the amino terminus of one subunit of a protein of interest to the carboxyl terminus of another subunit in the complex. These fusion proteins can consist of linked versions of homodimers, homomultimers, heterodimers or higher order heteromultimers. In the simplest case, one adds polypeptide linkers between the native termini to be joined. Two significant variations can be made. First, one can construct diverse libraries of variations of the wild type sequence in and around the junctions and in the linkers to facilitate the construction of active fusion proteins. Secondly, Zhang et al., (*Biochemistry* 32:12311–12318 (1993)) have described circular permutations of T4 lysozyme in which the native amino and carboxyl termini have been joined and novel amino and carboxyl termini have been engineered into the protein. The methods of circular permutation, libraries of linkers, and libraries of junctional sequences flanking the linkers allow one to construct libraries that are diverse in topological linkage strategies and in primary sequence. These libraries are expressed and selected for activity. Any of the above mentioned strategies for screening or selection can be used, with phage display being preferable in most cases. Genes encoding active fusion proteins are recovered, mutagenized, reselected, and subjected to standard RSR protocols to optimize their function. Preferably, a population of selected mutant single chain constructs is PCR amplified in two seprate PCR reactions such that each of the two domains is amplified separately. Oligonucleotides are derived from the 5' and 3' ends of the gene and from both strands of the linker. The separately amplified domains are shuffled in separate reactions, then the two populations are recombined using PCR reassembly to generate intact single chain constructs for further rounds of selection and evolution.

V. Improved Properties of Pharmaceutical Proteins

A. Evolved Specificity for Receptor or Cell Type of Interest

The majority of the proteins listed in Table I are either receptors or ligands of pharmaceutical interest. Many agonists such as chemokines or interleukins agonize more than one receptor. Evolved mutants with improved specificity may have reduced side effects due to their loss of activity on receptors which are implicated in a particular side effect profile. For most of these ligand/receptors, mutant forms with improved affinity would have improved pharmaceutical properties. For example, an antagonistic form of RANTES with improved affinity for CKR5 should be an improved inhibitor of HIV infection by virtue of achieving greater receptor occupancy for a given dose of the drug. Using the selections and screens outlined above in combination with RSR, the affinities and specificities of any of the proteins listed in Table I can be improved. For example, the mammalian display format could be used to evolve TNF receptors with improvea affinity for TNF.

Other examples include evolved interferon alpha variants that arrest tumor cell proliferation but do not stimulate NK cells, IL2 variants that stimulate the low affinity IL2 receptor complex but not the high affinity receptor (or vice versa), superantigens that stimulate only a subset of the V beta proteins recognized by the wild type protein (preferably a single V beta), antagonistic forms of chemokines that specifically antagonize only a receptor of interest, antibodies with reduced cross-reactivity, and chimeric factors that specifically activate a particular receptor complex. As an example of this latter case, one could make chimeras between IL2 and IL4, 7, 9, or 15 that also can bind the IL2 receptor alpha, beta and gamma chains (Theze et al., *Imm. Today* 17:481–486 (1996)), and select for chimeras that retain binding for the intermediate affinity IL2 receptor complex on monocytes but have reduced affinity for the high affinity IL2 alpha, beta, gamma receptor complex on activated T cells.

B. Evolved Aaonists with Increased Potency

In some embodiments of the invention, a preferred strategy is the selection or screening for mutants with increased agonist activity using the whole cell formats described above, combined with RSR. For example, a library of mutants of IL3 is expressed in active form on phage as described by Gram et al. (*J. Immun. Meth.* 161:169–176

(1993)). Clonal lysates resulting from infection with plaque-purified phage are prepared in a high through-put format such as a 96-well microtiter format. An IL3-dependent cell line expressing a reporter gene such as GFP is stimulated with the phage lysates in a high throughput 96-well. Phage that result in positive signals at the greatest dilution of phage supernatants are recovered; alternatively, DNA encoding the mutant IL3 can be recovered by PCR. In some embodiments, single cells expressing GFP under control of an IL3 responsive promoter can stimulated with the IL3 phage library, and the positive FACS sorted. The nucleic acid is then subjected to PCR, and the process repeated until the desired level of improvement is obtained.

TABLE I

POLYPEPTIDE CANDIDATES FOR EVOLUTION

Name

Alpha-1 antitrypsin
Angiostatin
Antihemolytic factor
Apolipoprotein
Apoprotein
Atrial natriuretic factor
Atrial natriuretic polypeptide
Atrial peptides
C-X-C chemokines (e.g., T39765, NAP-2, ENA-78, Gro-a, Gro-b, Gro-c, IP-10, GCP-2, NAP-4, SDF-1, PF4, MIG)
Calcitonin
CC chemokines (e.g., Monocyte chemoattractant protein-1, Monocyte chemoattractant protein-2, Monocyte chemoattractant protein-3, Monocyte inflammatory protein-1 alpha, Monocyte inflammatory protein-1 beta, RANTES, I309, R83915, R91733, HCC1, T58847, D31065, T64262)
CD40 ligand
Collagen
Colony stimulating factor (CSF)
Complement factor 5a
Complement inhibitor
Complement receptor 1
Factor IX
Factor VII
Factor VIII
Factor X
Fibrinogen
Fibronectin
Glucocerebrosidase
Gonadotropin
Hedgehog proteins (e.g., Sonic, Indian, Desert)
Hemoglobin (for blood substitute; for radiosensitization)
Hirudin
Human serum albumin
Lactoferrin
Luciferase
Neurturin
Neutrophil inhibitory factor (NIF)
Osteogenic protein
Parathyroid hormone
Protein A
Protein G
Relaxin
Renin
Salmon calcitonin
Salmon growth hormone
Soluble complement receptor I
Soluble I-CAM 1
Soluble interleukin receptors (IL-1, 2, 3, 4, 5, 6, 7, 9, 10, 11, 12, 13, 14, 15)
Soluble TNF receptor
Somatomedin
Somatostatin
Somatotropin
Streptokinase

TABLE I-continued

POLYPEPTIDE CANDIDATES FOR EVOLUTION

Name

Superantigens, i.e., Staphylococcal enterotoxins (SEA, SEB, SEC1, SEC2, SEC3, SED, SEE), Toxic shock syndrome toxin (TSST-1), Exfoliating toxins A and B, Pyrogenic exotoxins A, B, and C, and M. arthritidis mitogen
Superoxide dismutase
Thymosin alpha 1
Tissue plasminogen activator
Tumor necrosis factor beta (TNF beta)
Tumor necrosis factor receptor (TNFR)
Tumor necrosis factor-alpha (TNF alpha)
Urokinase C. Evolution of Components of Eukaryotic Signal Transduction or Transcriptional Pathways Using the screens and selections listed above, RSR can be used in several ways to modify eukaryotic signal transduction or transcriptional pathways. Any component of a signal transduction pathway of interest, of the regulatory regions and transcriptional activators that interact with this region and with chemicals that induce transcription can be evolved. This generates regulatory systems in which transcription is activated more potently by the natural inducer or by analogues of the normal inducer. This technology is preferred for the development and optimization of diverse assays of biotechnological interest. For .example, dozens of 7 transmembrane receptors (7-TM) are validated targets for drug discovery (see, for example, Siderovski et al., *Curr Biol.*, 6(2):211–212 (1996); An et al., *FEBS Lett.*, 375(1–2):121–124 (1995); Raport et al., *Gene*, 163(2):295–299 (1995); Song et al., *Genomics*, 28(2):347–349 (1995); Strader et al. *FASEB J.*, 9(9):745–754 (1995); Benka et al., *FEBS Lett.*, 363(1–2):49–52 (1995); Spiegel, *J. Clin Endocrinol. Metab.*, 81(7):2434–2442 (1996); Post et al., *FASEB J.*, 10(7):741–749 (1996); Reisine et al., *Ann NY Acad. Sci.*, 780:168–175 (1996); Spiegel, *Annu. Rev. Physiol.*, 58:143–170 (1996); Barak et al., *Biochemistry*, 34(47):15407–15414 (1995); and Shenker, *Baillieres Clin. Endocrinol. Metab.*, 9(3):427–451 (1995)). The development of sensitive high throughput assays for agonists and antagonists of these receptors is essential for exploiting the full potential of combinatorial chemistry in discovering such ligands. Additionally, biodetectors or biosensors for different chemicals can be developed by evolving 7-TM's to respond agonistically to novel chemicals or proteins of interest. In this case, selection would be for contructs that are activated by the new chemical or polypeptide to be detected. Screening could be done simply with fluorescence or light activated cell sorting, since the desired improvement is coupled to light production.

In addition to detection of small molecules such as pharmaceutical drugs and environmental pollutants, biosensors can be developed that will respond to any chemical for which there are receptors, or for which receptors can be evolved by recursive sequence recombination, such as hormones, growth factors, metals and drugs. The receptors may be intracellular and direct activators of transcription, or they may be membrane bound receptors that activate transcription of the signal indirectly, for example by a phosphorylation cascade. They may also not act on transcription at all, but may produce a signal by some post-transcriptional modification of a component of the signal generating pathway. These receptors may also be generated by fusing domains responsible for binding different ligands with different signalling domains. Again, recursive sequence recombination can be used to increase the amplitude of the signal agenerated to optimize expression and functioning of chimeric receptors, and to alter the specificity of the chemicals detected by the receptor.

For example, G proteins can be evolved to efficiently couple mammalian 7-TM receptors to yeast signal transduction apathways. There are 23 presently known G alpha protein loci in mammals which can be grouped by sequence and functional similarity into four groups, Gs (Gna, Gna1), Gi (Gnai-2, Gnai-3, Gnai-1, Gnao, Gnat-1, Gnat-2, Gnaz), Gq (Gnaq, Gna-11, Gna-14, Gna-15) and G12 (Gna-12, Gna-13) (B. Nurnberg et al., *J. Mol. Med.*, 73:123–132 (1995)). They possess an endogenous GTP-ase activity allowing reversible functional coupling between ligand-bound receptors and downstream effectors such as enzymes and ion channels. G alpha proteins are complexed noncovalently with G beta and G gamma proteins as well as to their cognate 7-TM receptor(s). Receptor and signal specificity are controlled by the particular combination of G alpha, G beta (of which there are five known loci) and G gamma (seven known loci) subunits. Activation of the heterotrimeric complex by ligand bound receptor results in dissociation of the complex into G alpha monomers and G beta, gamma dimers which then transmit signals by associating with downstream effector proteins. The G alpha subunit is believed to be the subunit that contacts the 7-TM, and thus it is a focal point for the evolution of chimeric or evolved G alpha subunits that can transmit signals from mammalian 7-TM's to yeast downstream genes.

Yeast based bioassays for mammalian receptors will greatly facilitate the discovery of novel ligands. Kang et al. (*Mol. Cell Biol.* 10:2582–2590 (1990)) have described the partial complementation of yeast strains bearing mutations in SCG1 (GPA1), a homologue of the alpha subunits of G proteins involved in signal transduction in mammalian cells, by mammalian and hybrid yeast/mammalian G alpha proteins. These hybrids have partial function, such as complementing the growth defect in scg1 strains, but do not allow mating and hence do not fully complement function in the pheromone signal transduction pathway. Price et al. (*Mol. Cell Biol.* 15:6188–6195 (1995)) have expressed rat somatostatin receptor subtype 2 (SSTR2) in yeast and demonstrated transmission of ligand binding signals by this 7-TM receptor through yeast and chimeric mammalian/yeast G alpha subunits ("coupling") to a HIS3 reporter gene, under control of the pheromone responsive promoter FUS-1 enabling otherwise HIS3(−) cells to grow on minimal medium lacking histidine.

Such strains are useful as reporter strains for mammalian receptors, but suffer from important limitations as exemplified by the study of Kang et al., where there appears to be a block in the transmission of signals from the yeast pheromone receptors to the mammalian G proteins. In general, to couple a mammalian 7-TM receptor to yeast signal transduction pathways one couples the mammalian receptor to yeast, mammalian, or chimeric G alpha proteins, and these will in turn productively interact with downstream components in the pathway to induce expression of a pheromone responsive promoter such as FUS-1. Such functional reconstitution is commonly referred to as "coupling".

The methods described herein can be used to evolve the coupling of mammalian 7-TM receptors to yeast signal transduction pathways. A typical approach is as follows: (1) clone a 7-TM of interest into a yeast strain with a modified pheromone response pathway similar to that described by Price (e.g., strains deficient in FAR1, a negative regulator of $G_1$ cyclins, and deficient in SST2 which causes the cells to be hypersensitive to the presence of pheromone), (2) construct libraries of chimeras between the mammalian G alpha protein(s) known or thought to interact with the GPA1 or homologous yeast G alpha proteins, (3) place a selectable reporter gene such as HIS3 under control of the pheromone responsive promoter FUSl (Price et al., *Mol. Cell Biol.* 15:6188–6195 (1995)). Alternatively, a screenable gene such as luciferase may be placed under the control of the FUS1 promoter; (4) transform library (2) into strain (3) (HIS(−)), (5) screen or select for expression of the reporter in response to the ligand of interest, for example by growing the library of transformants on minimal plates in the presence of ligand to demand HIS3 expression, (6) recover the selected cells, and and apply RSR to evolve improved expression of the reporter under the control of the pheromone responsive promoter FUS1.

A second important consideration in evolving strains with optimized reporter constructs for signal transduction pathways of interest is optimizing the signal to noise ratio (the ratio of gene expression under inducing vs noninducing conditions). Many 7-TM pathways are leaky such that the maximal induction of a typical reporter gene is 5 to 10-fold over background. This range of signal to noise may be insufficient to detect small effects in many high through put assays. Therefore, it is of interest to couple the 7-TM pathway to a second nonlinear amplification system that is tuned to be below but near the threshold of activation in the uninduced state. An example of a nonlinear amplification system is expression of genes driven by the lambda PL promoter. Complex cooperative interactions between lambda repressor bound at three adjacent sites in the cI promoter result in very efficient repression above a certain concentration of repressor. Below a critical threshold dramatic induction is seen and there is a window within which a small decrease in repressor concentration leads to a large increase in gene expression (Ptashne, *A Genetic Switch:Phage Lambda and Higher Organisms*, Blackwell Scientific Publ. Cambridge, Mass., 1992). Analogous effects are seen for some eukaryotic promoters such as those regulated by GAL4. Placing the expression of a limiting component of a transcription factor for such a promoter (GAL4) under the control of a GAL4 enhanced 7-TM responsive promoter results in small levels of induction of the 7-TM pathway signal being amplified to a much larger change in the expression of a reporter construct also under the control of a GAL4 dependent promoter.

An example of such a coupled system is to place GAL4 under control of the FUS-1 pheromone responsive promoter and to have the-intracellular GAL4 (itself a transcriptional enhancer) level positively feedback on itself by placing a GAL4 binding site upstream of the FUS-1 promoter. A reporter gene is also put under the control of a GAL4 activated promoter. This system is designed so that GAL4 expression will nonlinearly self-amplify and co-amplify expression of a reporter gene such as luciferase upon reaching a certain threshold in the cell. RSR can be used to great advantage to evolve reporter constructs with the desired signaling properties, as follows: (1) A single plasmid construct is made which contains both the GAL4/pheromone pathway regulated GAL4 gene and the GAL4 regulated reporter gene. (2) This construct is mutagenized and transformed into the appropriately engineered yeast strain expressing a 7-TM and chimeric yeast/mammalian protein of interest. (3) Cells are stimulated with agonists and screened (or selected) based on the activity of the reporter gene. In a preferred format, luciferase is the reporter gene and activity is quantitated before and after stimulation with the agonist, thus allowing for a quantitative measurement of signal to noise for each colony. (4) Cells with improved reporter properties are recovered, the constructs are shuffled, and RSR is applied to further evolve the plasmid to give optimal signal noise characteristics.

These approaches are general and illustrate how any component of a signal transduction pathway or transcription factor could be evolved using RSR and the screens and selections described above. For example, these specific methods could be used to evolve 7-TM receptors with specificity for novel ligands, specificity of nuclear receptors for novel ligands (for example to obtain herbicide or other small molecule-inducible expression of genes of interest in transgenic plants, such that a given set of genes can be induced upon treatment with a given chemical agent), specificity of transcription factors to be responsive to viral factors (thus inducing antiviral or lethal genes in cells expressing this transcription factor [transgenics or cells treated with gene therapy constructs]), or specificity of transcription factors for activity in cancer cells (for example p53 deficient cells, thus allowing one to infect with gene therapy constructs expressing conditionally lethal genes in a tumor specific fashion).

The following examples are offered by way of illustration, not by way of limitation.

EXPERIMENTAL EXAMPLES
I. Evolution of BIAP

A preferred strategy to evolve BIAP is as follows. A codon usage libary is constructed from 60-mer oligonucleotides such that the central 20 bases of each oligo specifies the wild type protein, but encodes the wild-type protein sequence with degenerate codons. Preferably, very rare codons for the prokaryotic host of choice, such as *E. coli*, are not used. The 20 bases at each end of the oligo use non-degenerate, but preferred, codons in *E. coli*. The oligonucleotides are assembled into full-length genes as described above. The assembled products are cloned into an expression vector by techniques well known in the art. In some embodiments, the codon usage library is expressed with a library of secretory leader sequences, each of which directs the encoded BIAP protein to the *E. coli* periplasm. A library of leader sequences is used to optimize the combination of leader sequence and mutant. Examples of leader sequences are reviewed by Schatz et al. (*Ann Rev. Genet.* 24:215–248 (1990)). The cloned BIAP genes are expressed under the control of an inducible promoter such as the arabinose promoter. Arabinose-induced colonies are screened by spraying with a substrate for BIAP, bromo-chloro-indolyl phosphate (BCIP). The bluest colonies are picked visually and subjected to the RSR procedures described herein.

The oligonucleotides for construction of the codon usage library are listed in Table II. The corresponding locations of these promoters is provided in FIG. 1.

TABLE II

```
1.AACCCTCCAG TTCCGAACCC CATATGATGA TCACCCTGCG TAAACTGCCG
2.AACCCTCCAG TTCCGAACCC CATATGAAAA AAACCGCT
3.AACCCTCCAG TTCCGAACCC ATATACATAT GCGTGCTAAA
4.AACCCTCCAG TTCCGAACCC CATATGAAAT ACCTGCTGCC GACC
5.AACCCTCCAG TTCCGAACCC GATATACATA TGAAACAGTC
6.TGGTGTTATG TCTGCTCAGG CDATGGCDGT DGAYTTYCAY CTGGTTCCGG
  TTGAAGAGGA
7.GGCTGGTTTC GCTACCGTTG CDCARGCDGC DCCDAARGAY CTGGTTCCGG
  TTGAAGAGGA
8.CACCCCGATC GCTATCTCTT CYTTYGCDTC YACYGGYTCY CTGGTTCCGG
  TTGAAGAGGA
9.GCTGCTGGCT GCTCAGCCGG CDATGGCDAT GGAYATYGGY CTGGTTCCGG
  TTGAAGAGGA
10.TGCCGCTGCT GTTCACCCCG GTDACYAARG CDGCDCARGT DCTGGTTCCG
   GTTGAAGAGG A
11.CCCGGCTTTC TGGAACCGTC ARGCDGCDCA RGCDCTGGAC GTTGCTAAAA
   AACTGCAGCC
12.ACGTTATCCT GTTCCTGGGT GAYGGYATGG GYGTDCCDAC CGTTACCGCT
   ACCCGTATCC
13.AAACTGGGTC CGGAAACCCC DCTGGCDATG GAYCARTTYC CGTACGTTGC
   TCTGTCTAAA
14.GGTTCCGGAC TCTGCTGGTA CYGCDACYGC DTAYCTGTGC GGTGTTAAAG
   GTAACTACCG
15.CTGCTCGTTA CAACCAGTGC AARACYACYC GYGGYAAYGA AGTTACCTCT
   GTTATGAACC
16.TCTGTTGGTG TTGTTACCAC YACYCGYGTD CARCAYGCDT CTCCGGCTGG
   TGCTTACGCT
17.GTACTCTGAC GCTGACCTGC CDGCDGAYGC DCARATGAAC GGTTGCCAGG
   ACATCGCTGC
18.ACATCGACGT TATCCTGGGT GGYGGYCGYA ARTAYATGTT CCCGGTTGGT
   ACCCCGGACC
19.TCTGTTAACG GTGTTCGTAA RCGYAARCAR AAYCTGGTDC AGGCTTGGCA
   GGCTAAACAC
20.GAACCGTACC GCTCTGCTGC ARGCDGCDGA YGAYTCYTCT GTTACCCACC
   TGATGGGTCT
21.AATACAACGT TCAGCAGGAC CAYACYAARG AYCCDACYCT GCAGGAAATG
   ACCGAAGTTG
22.AACCCGCGTG GTTTCTACCT GTTYGTDGAR GGYGGYCGYA TCGACCACGG
   TCACCACGAC
23.GACCAAGCT GGTATGTTCG AYAAYGCDAT YGCDAARGCT AACGAACTGA
   CCTCTGAACT
24.CCGCTGACCA CTCTCACGTT TTYTCYTTYG GYGGYTAYAC CCTGCGTGGT
   ACCTCTATCT
25.GCTCTGGACT CTAAATCTTA YACYTCYATY CTGTAYGGYA ACGGTCCGGG
   TTACGCTCTG
```

TABLE II-continued

```
26. CGTTAACGAC TCTACCTCTG ARGAYCCDTC YTAYCARCAG CAGGCTGCTG
    TTCCGCAGGC
27. AAGACGTTGC TGTTTTCGCT CGYGGYCCDC ARGCDCAYCT GGTTCACGGT
    GTTGAAGAAG
28. ATGGCTTTCG CTGGTTGCGT DGARCCDTAY ACYGAYTGYA ACCTGCCGGC
    TCCGACCACC
29. TGCTCACCTG GCTGCTTMAC CDCCDCCDCT GGCDCTGCTG GCTGGTGCTA
    TGCTGCTCCT C
30. TTCCGCCTCT AGAGAATTCT TARTACAGRG THGGHGCCAG GAGGAGCAGC
    ATAGCACCAG CC
31. AAGCAGCCAG GTGAGCAGCG TCHGGRATRG ARGTHGCGGT GGTCGGAGCC
    GGCAGGTT
32. CGCAACCAGC GAAAGCCATG ATRTGHGCHA CRAARGTYTC TTCTTCAACA
    CCGTGAACCA
33. GCGAAAACAG CAACGTCTTC RCCRCCRTGR GTYTCRGAHG CCTGCGGAAC
    AGCAGCCTGC
34. AGAGGTAGAG TCGTTAACGT CHGGRCGRGA RCCRCCRCCC AGAGCGTAAC
    CCGGACCGTT
35. AAGATTTAGA GTCCAGAGCT TTRGAHGGHG CCAGRCCRAA GATAGAGGTA
    CCACGCAGGG
36. ACGTGAGAGT GGTCAGCGGT HACCAGRATC AGRGTRTCCA GTTCAGAGGT
    CAGTTCGTTA
37. GAACATACCA GCTTCGGTCA GHGCCATRTA HGCYTTRTCG TCGTGGTGAC
    CGTGGTCGAT
38. GGTAGAAACC ACGCGGGTTA CGRGAHACHA CRCGCAGHGC AACTTCGGTC
    ATTTCCTGCA
39. TCCTGCTGAA CGTTGTATTT CATRTCHGCH GGYTCRAACA GACCCATCAG
    GTGGGTAACA
40. CAGCAGAGCG GTACGGTTCC AHACRTAYTG HGCRCCYTGG TGTTTAGCCT
    GCCAAGCCTG
41. TACGAACACC GTTAACAGAA GCRTCRTCHG GRTAYTCHGG GTCCGGGGTA
    CCAACCGGGA
42. CCCAGGATAA CGTCGATGTC CATRTTRTTH ACCAGYTGHG CAGCGATGTC
    CTGGCAACCG
43. CAGGTCAGCG TCAGAGTACC ARTTRCGRTT HACRGTRTGA GCGTAAGCAC
    CAGCCGGAGA
44. TGGTAACAAC ACCAACAGAT TTRCCHGCYT TYTTHGCRCG GTTCATAACA
    GAGGTAACTT
45. CACTGGTTGT AACGAGCAGC HGCRGAHACR CCRATRGTRC GGTAGTTACC
    TTTAACACCG
46. ACCAGCAGAG TCCGGAACCT GRCGRTCHAC RTTRTARGTT TTAGACAGAG
    CAACGTACGG
47. GGGTTTCCGG ACCCAGTTTA CCRTTCATYT GRCCYTTCAG GATACGGGTA
    GCGGTAACGG
48. CCCAGGAACA GGATAACGTT YTTHGCHGCR GTYTGRATHG GCTGCAGTTT
    TTTAGCAACG
49. ACGGTTCCAG AAAGCCGGGT CTTCCTCTTC AACCGGAACC AG
50. CCTGAGCAGA CATAACACCA GCHGCHACHG CHACHGCCAG CGGCAGTTTA
    CGCAGGGTGA
51. ACCGGGGTGA ACAGCAGCGG CAGCAGHGCC AGHGCRATRG TRGACTGTTT
    CATATGTATA TC
52. GCCGGCTGAG CAGCCAGCAG CAGCAGRCCH GCHGCHGCGG TCGGCAGCAG
    GTAGTTTCA
53. AAGAGATAGC GATCGGGGTG GTCAGHACRA TRCCCAGCAG TTTAGCACGC
    ATATGTATAT
54. CAACGGTAGC GAAACCAGCC AGHGCHACHG CRATHGCRAT AGCGGTTTTT
    TTCATATG
55  AGAATTCTCT AGAGGCGGAA ACTCTCCAAC TCCCAGGTT
56. TGAGAGGTTG AGGGTCCAAT TGGGAGGTCA AGGCTTGGG       (SEQ ID NOS. 1-56, respectively)
```

All oligonucleotides listed 5' to 31. The code for degenerate positions is: R: A or G; Y: C or T; H: A or C or T; D: A or G or T.

II. MaGmalian Surface Display

During an immune response antibodies naturally undergo a process of affinity maturation resulting in mutant antibodies with improved affinities for their cognate antigens. This process is driven by somatic hypermutation of antibody genes coupled with clonal selection (Berek and Milstein, *Immun. Rev.* 96:23–41 (1987)). Patten et al. (*Science* 271:1086–1091 (1996)) have reconstructed the progression of a catalytic antibody from the germline sequence, which binds a p-nitrophenylphosphonate hapten with an affinity of 135 micromolar, to the affinity matured sequence which has acquired nine somatic mutations and binds with an affinity of 10 nanomolar. The affinity maturation of this antibody can be recapitulated and improved upon using cassette mutagenesis of the CDR's (or random mutagenesis such as with PCR), mammalian display, FACS selection for improved binding, and RSR to rapidly evolve improved affinity by recombining mutations encoding improved binding.

Genomic antibody expression shuttle vectors similar to those describede by Gascoigne et al. (*Proc. Natl. Sci. (U.S.A.)* 84:2936–2940 (1987)) are constructed such that libraries of mutant V region exons can be readily cloned into the shuttle vectors. The kappa construct is cloned onto a plasmid encoding puromycin resistance and the haeavy chain is cloned onto a neomycin resestance encoding vector. The cDNA derived variable region sequences encoding the mature and germline heavy and light chain V regions are reconfigured by PCR mutagenesis into genomic exons flanked by Sfi I sites with complementary Sfi I sites placed at the appropriate locations in the genomic shuttle vectors. The oligonucleotides used to create the intronic Sfi I sites flanking the VDY exon are: 5' Sfi I: 5'-TTCCATTTCA TACATGGCCG AAGGGGCCGT GCCATAGAGGA TTTT-3' (SEQ. ID NO. 100); 3'Sfi I: 5'-TTCTAAATG CATGTTGGCC TCCTTGGCCG GATTCTGAGC CTTCAGGACC A-3' (SEQ. ID NO. 101). Standard PCR mutagenesis protocols are applied to produce libraries of mutants wherein the following sets of residues (numbered according to Kabat, *Sequences of Proteins of Immunological Interest*, U.S. Dept of Health and Human Services, 1991) are randomized to NNK codons (GATC,GATC,GC):

| Chain | CDR | Mutated residues |
|---|---|---|
| V-L | 1 | 30, 31, 34 |
| V-L | 2 | 52, 53, 55 |
| V-H' | 2 | 55, 56, 65 |
| V-H | "4" | 74, 76, 78 |

Stable transfectant lines are made for each of the two light and heavy chain constructs (mature and germline) using the B cell myeloma AG8-653 (a gift from J. Kearney) as a host using standard electroporation protocols. Libraries of mutant plasmids encoding the indicated libraries of V-L mutants are transfected into the stable transformant expressing the germline V-H; and the V-H mutants are transfected into the germline V-L stable transfectant line. In both cases, the libraries are introduced by protoplast fusion (Sambrook et al., *Molecular Cloning*, CSH Press (1987)) to ensure that the majority of transfected cells receive one and only one mutant plasmid sequence (which would not be the case for electroporation where the majority of the transfected cells would receive many plasmids, each expressing a different mutant sequence).

The p-nitrophenylphosphonate hapten (JWJ-1) recognized by this antibody is synthesized as described by Patten et al. (*Science* 271:1086–1091 (1996)). JWJ-1 is coupled directly to 5-(((2-aminoethyl)thio)acetyl)fluorescein (Molecular Probes, Inc.) by formation of an amide bond using a standard coupling chemistry such as EDAC (March, *Advanced Organic Chemistry*, Third edition, John Wiley and Sons, 1985) to give a monomeric JWJ-1-FITC probe. A "dimeric" conjugate (two molecules of JWJ-1 coupled to a FACS marker) is made in order to get a higher avidity probe, thus making low affinity interactions (such as with the germline antibody) more readily detected by FACS. This is generated by staining with Texas Red conjugated to an anti-fluorescein antibody in the presence of two equivalents of JWJ-1-FITC. The bivalent structure of IgG then provides a homogeneous bivalent reagent. A spin column is used to remove excess JWJ-1-FITC molecules that are not bound to the anti-FITC reagent. A tetravalent reagent is made as follows. One equivalent of biotin is coupled with EDAC to two equivalents of ethylenediamine, and this is then be coupled to the free carboxylate on JWJ-1. The biotiylated JWJ-1 product is purified by ion exchange chromatography and characterized by mass spectrometry. FITC labelled avidin is incubated with the biotinylated JWJ-1 in order to generate a tetravalent probe.

The FACS selection is performed as follows, according to a protocol similar to that of Panka et al. (*Proc. Natl. Acad. Sci. (U.S.A.)* 85:3080–3084 (1988)). After transfection of libraries of mutant antibody genes by the method of protoplast fusion (with recovery for 36–72 hours), the cells are incubated on ice with fluorescently labelled hapten. The incubation is done on ice to minimize pinocytosis of the FITC conjugate which may contribute to nonspecific background. The cells are then sorted on the FACS either with or without a washing step. FACSing without a washing step is preferable because the off rate for the germline antibody prior to affinity maturation is expected to be very fast (>0.1 sec-1; Patten et al., *Science* 271:1086–1091 (1996)); a washing step adds a complicating variable. The brightest 0.1–10% of the cells are collected.

Four parameters are manipulated to optimize the selection for increased binding: monomeric vs dimeric vs tetrameric hapten, concentration of hapten used in the staining reaction (low concentration selects for high affinity Kd's), time between washing and FACS (longer time selects for low off rates), and selectivity in the gating (i.e. take the top 0.1% to 10%, more preferably the top 0.1%). The constructs expressing the germline, mature, and both combinations of half germline are used as controls to optimize this selectivity.

Plasmids are recovered from the FACS selected cells by the transformation of an *E. coli* host with Hirt supernatants. Alternatively, the mutant V gene exons are PCR-amplified from the FACS selected cells. The recovered V gene exons are subjected to RSR, recloned into the corresponding genomic shuttle vector, and the procedure recursively applied until the mean fluorescence intensity has increased. A relevant positive control for improved binding is transfection with the affinity matured 48G7 exons (Patten et al., op. cit.).

In a further experiment, equal numbers of germline and each of the two half germline transfectants are mixed. The brightest cells are selected under conditions described above. The V genes are recovered by PCR, recloned into expression vectors, and co-transfected, either two plasmids per *E. coli* followed by protoplast fusion, or by bulk electroporation. The mean fluorescent intensity of the transfectants should increase due to enrichment of mature relative to germline V regions.

This methodology can be applied to evolve any receptor-ligand or binding partner interaction. Natural expression formats can be used to express libraries of mutants of any receptor for which one wants to improve the affinity for the natural or novel ligands. Typical examples would be improvement of the affinity of T cell receptors for ligands of interest (i.e. MHC/tumor peptide antigen complexes) or TNF receptor for TNF (soluble forms of TNF receptors are used therapeutically to neutralize TNF activity).

This format can also be used to select for mutant forms of ligands by expressing the ligand in a membrane bound form with an engineered membrane anchor by a strategy analogous to that of Wettstein et al. (*J. Exp. Med.* 174:219–28 (1991)). FACS selection is then performed with fluorescently labelled receptor. In this format one could, for example, evolve improved receptor antagonists from naturally occurring receptor antagonists (IL1 receptor antagonist, for example). Mutant forms of agonists with improved affinity for their cognate receptors could also be evolved in this format. These mutants would be candidates for improved agonists or potent receptor antagonists, analogous to reported antagonistic mutant forms of IL3.

III. Evolution of Alpha Interferon

There are at hand 18 known non-allelic human interferon-alpha (INF-α) genes, with highly related primary structures (78–95% identical) and with a broad range of biological activities. Many hybrid interferons with interesting biological activities differing from the parental molecules have been described (reviewed by Horisberger and Di Marco, *Pharm. Ther.* 66:507–534 (1995)). A consensus human alpha interferon, IFN-Con1, has been constructed synthetically wherein the most common residue in fourteen known IFN-α's has been put at each position, and it compares favorably with the naturally occurring interferons (Ozes et al., *J. Interferon Res.* 12:55–59 (1992)). This IFN contains 20 amino acid changes relative to IFN-α2a, the INF-α to which it is most closely related. IFN-Con1 has 10-fold higher specific antiviral activity than any known natural IFN subtype. IFN-α Con1 has in vitro activities 10 to 20 fold higher than that of recombinant IFN α-2a (the major IFN used clinically) in antiviral, antiproliferative and NK cell activation. Thus, there is considerable interest in producing interferon hybrids which combine the most desirable traits from two or more interferons. However, given the enormous number of potential hybrids and the lack of a crystal structure of IFN-α or of the IFN-α receptor, there is a perceived impasse in the development of novel hybrids (Horisberger and Di Marco, *Pharm. Ther.* 66:507–534 (1995)).

The biological effects of IFN-α's are diverse, and include such properties as induction of antiviral state (induction of factors that arrest translation and degrade mRNA); inhibition of cell growth; induction of Class I and Class II MHC; activation of monocytes and macrophages; activation of natural killer cells; activation of cytotoxic T cells; modulation of Ig synthesis in B cells; and pyrogenic activity.

The various IFN-α's subtypes have unique spectra of activities on different target cells and unique side effect profiles (Ortaldo et al., *Proc. Natl. Acad. Sci. (U.S.A.)* 81:4926–4929 (1984); Overall et al., *J. Interferon Res.* 12:281–288 (1992); Fish and Stebbing, *Biochem. Biophys. Res. Comm.* 112:537–546 (1983); Weck et al., *J. Gen. Virol.* 57:233–237 (1981)). For example, human IFNα has very mild side effects but low antiviral activity. Human IFNα8 has very high antiviral activity, but relatively severe side effects. Human IFNα7 lacks NK activity and blocks NK stimulation by other INFα's. Human IFN-αJ lacks the ability to stimulate NK cells, but it can bind to the IFN-α receptor on NK cells and block the stimulatory activity of IFN-αA (Langer et al., *J. Interferon Res.* 6:97–105 (1986)).

The therapeutic applications of interferons are limited by diverse and severe side effect profiles which include flu-like symptoms, fatigue, neurological disorders including hallucination, fever, hepatic enzyme elevation, and leukopenia. The multiplicity of effects of IFN-α's has stimulated the hypothesis that there may be more than one receptor or a multicomponent receptor for the IFN-α family (R. Hu et al., *J. Biol. Chem.* 268:12591–12595 (1993)). Thus, the existence of abundant naturally occurring diversity within the human alpha IFN's (and hence a large sequence space of recombinants) along with the complexity of the IFN-α receptors and activities creates an opportunity for the construction of superior hybrids.

A. Complexity of the Sequence Space

Figure 2F:
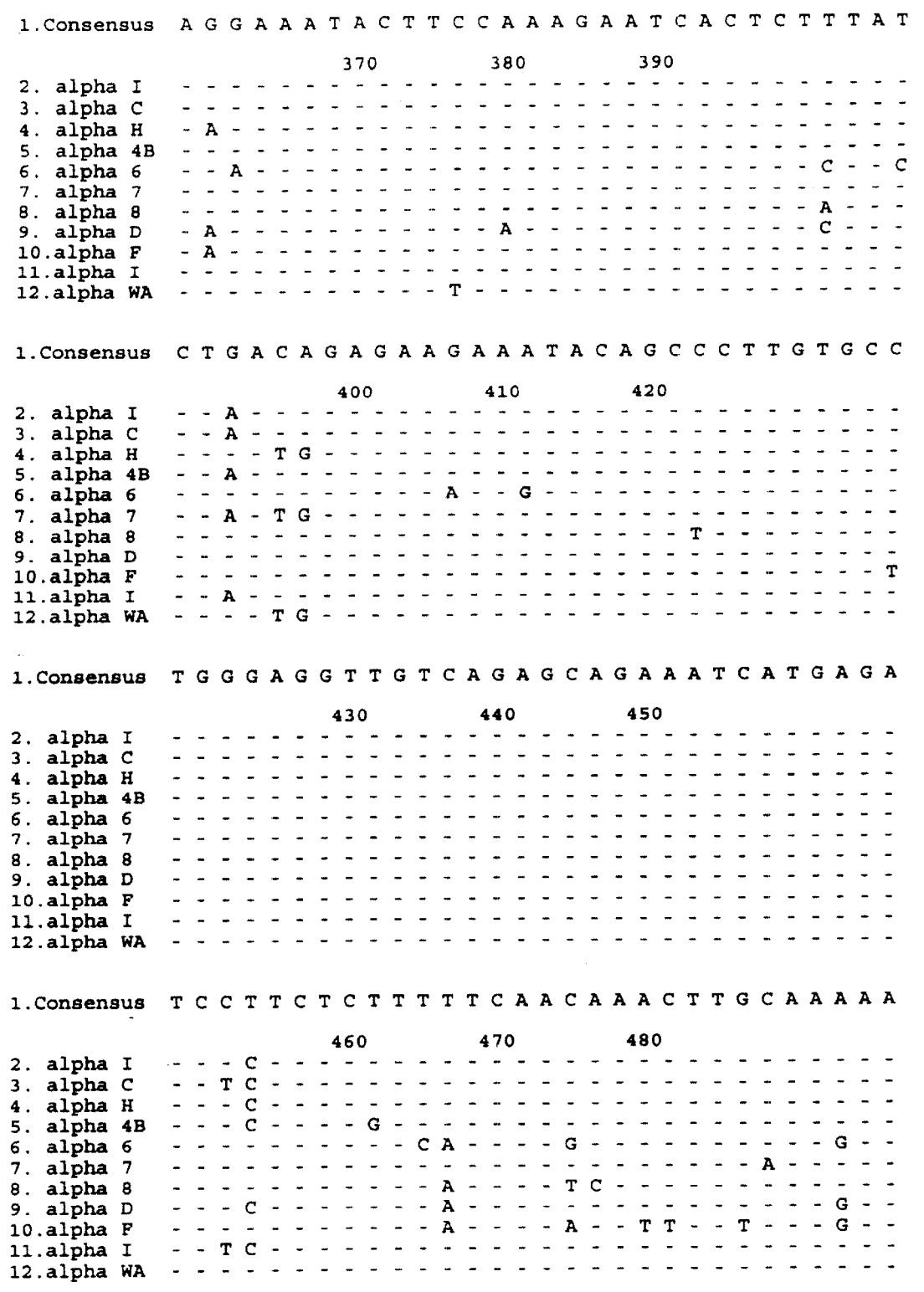

FIG. 2 shows the protein sequences of 11 human IFN-α's. The differences from consensus are indicated. Those positions where a degenerate codon can capture all of the diversity are indicated with an asterisk. Examination of the aligned sequences reveals that there are 57 positions with two, 15 positions with three, and 4 positions with four possible amino acids encoded in this group of alpha interferon genes. Thus, the potential diversity encoded by permutation of all of this naturally occurring diversity is: $2^{57} \times 3^{15} \times 4^4 = 5.3 \times 10^{26}$. Among these hybrids, of the 76 polymorphisms spread over a total of 175 sites in the 11 interferon genes, 171 of the 175 changes can be incorporated into homologue libraries using single degenerate codons at the corresponding positions. For example, Arg, Trp and Gly can all be encoded by the degenerate codon [A,T,G]GG. Using such a strategy, $1.3 \times 10^{25}$ hybrids can be captured with a single set of degenerate oligonucleotides. As is evident from Tables III to VI, 27 oligonucleotides is sufficient to shuffle all eleven human alpha interferons. Virtually all of the natural diversity is thereby encoded and fully permuted due to degeneracies in the nine "block" oligonucleotides in Table V.

B. Properties of a "Coarse Grain" Search of Homologue Sequence Space

The modelled structure of IFN alpha (Kontsek, *Acta Vir.* 38:345–360 (1994)) has been divided into nine segments based on a combination of criteria of maintaining secondary structure elements as single units and placing/choosing placement of the segment boundaries in regions of high identity. Hence, one can capture the whole family with a single set of mildly degenerate oligonucleotides. Table III and FIG. 2 give the precise locations of these boundaries at the protein and DNA levels respectively. It should be emphasized that this particular segmentation scheme is arbitrary and that other segmentation schemes could also be pursued. The general strategy does not depend on placement of recombination boundaries at regions of high identity between the family members or on any particular algorithm for breaking the structure into segments.

TABLE III

Segmentation Scheme for Alpha Interferon

| Segment | Amino Acids | # Alleles | # Permutations of all Sequence Variations |
|---|---|---|---|
| 1 | 1–21 | 5 | 1024 |
| 2 | 22–51 | 10 | $6.2 \times 10^4$ |
| 3 | 52–67 | 6 | 96 |
| 4 | 68–80 | 7 | 1024 |
| 5 | 81–92 | 7 | 192 |
| 6 | 93–115 | 10 | $2.5 \times 10^5$ |
| 7 | 116–131 | 4 | 8 |
| 8 | 132–138 | 4 | 8 |
| 9 | 139–167 | 9 | 9216 |

Many of the IFN's are identical over some of the segments, and thus there are less than eleven different "alleles" of each segment. Thus, a library consisting of the permutations of the segment "alleles" would have a potential complexity of $2.1 \times 10^7$ (5 segment #1's times 10 segment #2's x. . . x9 segment # 9's). This is far more than can be examined in most of the screening procedures described, and thus this is a good problem for using RSR to search the sequence space.

C. Detailed Strategies for Using RSR to Search the IFN-alpha Homolooue Sequence Space The methods described herein for oligo directed shuffling (i.e. bridge oligonucleotides) are employed to construct libraries of interferon alpha hybrids, and the general methods described above are employed to screen or select these mutants for improved function. As there are numerous formats in which to screen or select for improved interferon activity, many of which depend on the unique properties of interferons, exemplary descriptions of IFN based assays are described below.

D. A Protocol for a Coarse Grain Search of Hybrid IFN Alpha Secuence Space

In brief, libraries are constructed wherein the 11 homologous forms of the nine segments are permuted (note that in many cases two homologues are identical over a given segment). All nine segments are PCR- amplified out of all eleven IFN alpha genes with the eighteen oligonucleotides listed in Table IV, and reassembled into full length genes with oligo directed recombination. An arbitrary number, e.g., 1000, clones from the library are prepared in a 96-well expression/purification format. Hybrids with the most potent antiviral activities are screened. Nucleic acid is recovered by PCR amplification, and subjected to recombination using bridge oligonucleotides. These steps are repeated until candidates with desired properties are obtained.

E. Strategies for Examining the Space of $>10^{26}$ Fine Grain Hybrids

In brief, each of the nine segments is synthesized with one degenerate oligo per segment. Degeneracies are chosen to capture all of the IFN-alpha diversity that can be captured with a single degenerate codon without adding any non-natural sequence. A second set of degenerate oligonucleotides encoding the nine segments is generated wherein all of the natural diversity is captured, but additional non-natural mutations are included at positions where necessitated by the constraints of the genetic code. In most cases all of the diversity can be captured with a single degenerate codon; in some cases a degenerate codon will capture all of the natural diversity but will add one non-natural mutation; at a few postions it is not possible to capture the natural diversity without putting in a highly degenerate codon which will create more than one non-natural mutation. It is at these positions that this second set of oligonucleotides will differ from the first set by being more inclusive. Each of the nine synthetic segments is then amplified by PCR with the 18 PCR oligonucleotides. Full length genes using the oligo directed recombination method are generated, transfected into a host, and assayed for hybrids with desired properties. The best hybrids from (erg, the top 10%, 1% or 0.1%; preferably the top 1%) are subjected to RSR and the process repeated until a candidate with the desired properties is obtained.

F. "Non-gentle" Fine Grain Search

On the one hand, one could make libraries wherein each segment is derived from the degenerate synthetic oligonucleotides which will encode random permutations of the homologue diversity. In this case, the initial library will very sparsely search the space of $>10^{25}$ possible fine grain hybrids that are possible with this family of genes. One could proceed by breeding positives together from this search. However, there would be a large number of differences between independent members of such libraries, and consequently the breeding process would not be very "gentle" because pools of relatively divergent genes would be recombined at each step.

G. "Gentle" Fine Grain Search

One way to make this approach more gentle" would be to obtain a candidate starting point and to gently search from there. This starting point could be either one of the natural IFN-alpha's (such as IFN alpha-2a which is the one that is being used most widely therapeutically, the characterized IFN-Con1 consensus interferon, or a hit from screening the shuffled IFN-alpha's described above. Given a starting point, one would make separate libraries wherein one breeds the degenerate segment libraries one at a time into the founder sequence. Improved hits from each library would then be bred together to gently build up mutations all throughout the molecule.

H. Functional Cellular Assays

The following assays, well known in the art, are used to screen IFN alpha mutants: inhibition of viral killing; standard error of 30–50%; inhibition of plaque forming units; very low standard error (can measure small effects); reduced viral yield (useful for nonlethal, nonplaque forming viruses); inhibition of cell growth (3H-thymidine uptake assay; activation of NK cells to kill tumor cells; suppression of tumor formation by human INF administered to nude mice engrafted with human tumors (skin tumors for example).

Most of these assays are amenable to high throughput screening. Libraries of recombinant IFN alpha mutants are expressed and purified in high throughput formats such as expression, lysis and purification in a 96-well format using anti-IFN antibodies or an epitope tag and affinity resin. The purified IFN preparations are screened in a high throughput format, scored, and the mutants encoding the highest activities of interest are subjected to further mutagenesis, such as RSR, and the process repeated until a desired level of activity is obtained.

I. Phage Display

Standard phage display formats are used to display biologically active IFN. Libraries of chimeric IFN genes are expressed in this format and are selected (positively or negatively) for binding (or reduced binding) to one or more purified IFN receptor preparations or to one or more IFN receptor expressing cell types.

J. GFP or Luciferase Under Control of IFN-Alpha Dependent Promoter

Protein expressed by mutants can be screened in high throughput format on a reporter cell line which expresses GFP or luciferase under the control of an IFN alpha responsive promoter, such as an MHC Class I promoter driving GFP expression.

K. Stimulation of Target Cells with Intact Infections Particles

Purification of active IFN will limit the throughput of the assays described above. Expression of active IFN alpha on filamentous phage M13 would allow one to obtain homogenous preparations of IFN mutants in a format where thousands or tens of thousands of mutants could readily be handled. Gram et al. (*J. Imm. Meth.* 161:169–176 (1993)) have demonstrated that human IL3, a cytokine with a protein fold similar in topology to IFN alpha, can be expressed on the surface of M13 and that the resultant phage can present active IL3 to IL3 dependent cell lines. Similarly, Saggio et al. (*Gene* 152:35–39 (1995)) have shown that human ciliary neurotrophic factor, a four helix bundle cytokine, is biologically active when expressed on phage at concentrations similar to those of the soluble cytokine. Analogously, libraries of IFN alpha mutants on M13 can be expressed and lysates of defined titre used to present biologically active IFN in the high throughput assays and selections described herein.

The following calculation supports the feasibility of applying this technology to IFN alpha. Assuming (1) titres of $1\times10^{10}$ phage/ml with five active copies of interferon displayed per phage, and (2) that the displayed interferon is equivalently active to soluble recombinant interferon (it may well be more potent due to multi-valency), the question then is whether one can reasonably expect to see biological activity.

$$(1\times10^{10}\text{ phage/ml})\times(5\text{ IFN molecules/phage})\times(1\text{ mole}/6\times10^{23}\text{ molecules})\times(26{,}000\text{ gm/mole})\times(10^{9}\text{ ng/gm}) = 2.2\text{ ng/ml}$$

The range of concentration used in biological assays is: 1 ng/ml for NK activation, 0.1–10 ng/ml for antiproliferative activity on Eskol cells, and 0.1–1 ng/ml on Daudi cells (Ozes et al., *J. Interferon Res.* 12:55–59 (1992)). Although some subtypes are glycosylated, interferon alpha2a and consensus interferon are expressed in active recombinant form in *E. coli*, so at least these two do not require glycosylation for activity. Thus, IFN alpha expressed on filamentous phage is likely to be biologically active as phage lysates without further purification. Libraries of IFN chimeras are expressed in phage display formats and scored in the assays described above and below to identify mutants with improved properties to be put into further rounds of RSR.

When one phage is sufficient to activate one cell due to the high valency state of the displayed protein (five per phage in the gene III format; hundreds per phage in the gene VIII format; tens in the lambda gene V format), then a phage lysate can be used directly at suitable dilution to stimulate cells with a GFP reporter construct under the control of an IFN responsive promoter. Assuming that the phage remain attached after stimulation, expression and FACS purification of the responsive cells, one could then directly FACS purify hybrids with improved activity from very large libraries (up to and perhaps larger than $10^7$ phage per FACS run).

A second way in which FACS is used to advantage in this format is the following. Cells can be stimulated in a multi-well format with one lysate per well and a GFP type reporter construct. All stimulated cells are FACS purified to collect the brightest cells, and the IFN genes recovered and subjected to RSR, with iteration of the protocol until the desired level of improvement is obtained. In this protocol the stimulation is performed with individual concentrated lysates and hence the requirement that a single phage be sufficient to stimulate the cell is relaxed. Furthermore, one can gate to collect the brightest cells which, in turn, should have the most potent phage attached to them.

L. Cell Surface Display Protocol for IFN Alpha Mutants

A sample protocol follows for the cell surface display of IFN alpha mutants. This form of display has at least two advantages over phage display. First, the protein is displayed by a eukaryotic cell and hence can be expressed in a properly glycosylated form which may be necessary for some IFN alphas (and other growth factors). Secondly, it is a very high valency display format and is preferred in detecting activity from very weakly active mutants.

In brief, a library of mutant IFN's is constructed wherein a polypeptide signal for addition of a phosphoinositol tail has been fused to the carboxyl terminus, thus targeting the protein for surface expression (Wettstein et al., *J. Exp. Med.* 174:219–28 (1991)). The library is used to transfect reporter cells described above (luciferase reporter gene) in a microtiter format. Positives are detected with a charge coupling device(CCD) camera. Nucleic acids are recovered either by HIRT and retransformation of the host or by PCR, and are subjected to RSR for further evolution.

M. Autocrine Display Protocol for Viral Resistance

A sample protocol follows for the autocrine display of IFN alpha mutants. In brief, a library of IFN mutants is generated in a vector which allows for induction of expression (i.e. metallothionein promoter) and efficient secretion. The recipient cell line carrying an IFN responsive reporter cassette [GFP or luciferase] is induced by transfection with the mutant IFN constructs. Mutants which stimulate the IFN responsive promoter are detected by by FACS or CCD camera.

A variation on this format is to challenge transfectants with virus and select for survivors. One could do multiple rounds of viral challenge and outgrowth on each set of transfectants prior to retrieving the genes. Multiple rounds of killing and outgrowth allow an exponential amplification of a small advantage and hence provide an advantage in detecting small improvements in viral killing.

TABLE IV

Oligonucleotides needed for blockwise recombination: 18
Oligonucleotides for alpha interferon shuffling 1. 5'-TGT[G/A]ATCTG[C/T]CT[C/G]AGACC
2. 5'-GGCACAAATG [G/A/C]G [A/C]AGAATCTCTC
3. 5'-AGAGATTCT [G/T]C [C/T/G]CATTTGTGCC
4. 5'-CAGTTCCAGAAG [A/G]CT [G/C][C/A]AGCCATC
5. 5'-GATGGCT [T/G][G/C]AG [T/C]CTTCTGGAACTG
6. 5'-CTTCAATCTCTTCA[G/C]CACA
7. 5'-TGTG [G/C]TGAAGAGATTGAAG
8. 5'-GGA[T/A][G/C]AGA[C/G][C/G]CTCCTAGA
9. 5'-TCTAGGAG[G/C][G/C]TCT[G/C][T/A]TCC
10. 5'-GAACTT [T/G/A][T/A]CCAGCAA[A/C]TGAAT
11. 5'-ATTCA[T/G]TTGCTGG[A/T][A/T/C]AAGTTC
12. 5'-GGACT [T/C]CATCCTGGCTGTG
13. 5'-CACAGCCAGGATG [G/A]AGTCC
14. 5'-AAGAATCACTCTTTATCT
15. 5'-AGATAAAGAGTGATTCTT
16. 5'-TGGGAGGTTGTCAGAGCAG
17. 5'-CTGCTCTGACAACCTCCCA
18. 5'-TCA[A/T]TCCTT[C/A]CTC[T/C]TTAA
    (SEQ ID NOS. 57–74, respectively)

Brackets indicate degeneracy with equal mixture of the specified bases at those positions. The purpose of the degeneracy is to allow this one set of primers to prime all members of the IFN family with similar efficiency. The choice of the oligo driven recombination points is important because they will get "overwritten" in each cycle of breeding and hence cannot coevolve with the rest of the sequence over many cycles of selection.

TABLE V

Oligonucleotides needed for "fine grain" recombination of natural diversity over each of the nine blocks

| Block | #Length of oligo required |
| --- | --- |
| 1 | 76 |
| 2 | 95 |
| 3 | 65 |
| 4 | 56 |
| 5 | 51 |
| 6 | 93 |
| 7 | 50 |
| 8 | 62 |
| 9 | 80 |

TABLE VI

Amino acids that can be reached by a single step mutation in the codon of interest.

| Wild-Type Amino Acid | Amino acids reachable by one mutation |
| --- | --- |
| W | C, R, G, L |
| Y | F, S, C, H, N, D |
| F | L, I, V, S, Y, C |
| L | S, W, F, I, M, V, P |
| V | F, L, I, M, A, D, E, G |
| I | F, L, M, V, T, N, K, S, R |
| A | S, P, T, V, D, E, G |
| G | V, A, D, E, R, S, C, W |
| M | L, I, V, T, K, R |
| S | F, L, Y, C, W, P, T, A, R, G, N, T, I |

TABLE VI-continued

| Amino acids that can be reached by a single step mutation in the codon of interest. | |
|---|---|
| Wild-Type Amino Acid | Amino acids reachable by one mutation |
| T | S, P, A, I, M, N, K, S, R |
| P | S, T, A, L, H, Q, R |
| C | F, S, Y, R, G, W |
| N | Y, H, K, D, S, T, I |
| Q | Y, H, K, E, L, P, R |
| H | Y, Q, N, D, L, P, R |
| D | Y, H, N, E, V, A, G |
| E | Q, K, D, V, A, G |
| R | L, P, H, Q, C, W, S, G, K, T, I, M |
| K | Q, N, E, R, T, I, M |

Based on this Table, the polymorphic positions in IFN alpha where all of the diversity can be captured by a degenerate codon have been identified. Oligonucleotides of the length indicated in Table V above with the degeneracies inferred from Table VI are synthesized.

Although the foregoing invention has been described in some detail by way of illustration and example for purposes of clarity of understanding, it will be obvious that certain changes and modifications may be practiced within the scope of the appended claims.

All references cited herein are expressly incorporated in their entirety for all purposes.

What is claimed is:

1. A method of producing nucleic acids encoding mutagenized polypeptides, the method comprising:
   (a) selecting a plurality of homologous polypeptide sequences;
   (b) using computer modeling tools to model variances in amino acid sequence between the homologous polypeptide sequences;
   (c) selecting amino acid variations between the homologous polypeptide sequences based on the computer modeling information;
   (d) providing a plurality of overlapping polynucleotides comprising subsequences of nucleic acids encoding the plurality of homologous polypeptide sequences, and wherein the plurality of polynucleotides comprises subsequences encoding the amino acid variations selected in step (c); and,
   (e) reassembling the plurality of polynucleotides into nucleic acid sequences encoding mutagenized polypeptides.

2. The method of claim 1, wherein the homologous polypeptide sequences comprise allelic or species variants of one another.

3. The method of claim 1, wherein at least one of the homologous polypeptide sequences is a mutagenized variant.

4. The method of claim 1, wherein the homologous polypeptide squences are encoded by different members of a gene family.

5. The method of claim 1, wherein the homologous polypeptide sequences of step (a) are selected from the group consisting of proteins listed it Table I or alpha interferon.

6. The method of claim 1, wherein the homologous polypeptide sequences comprise at least about 50% sequence identity, at least about 70% sequence identity, at least about 80% sequence identity, or at least about 90% sequence identity.

7. The method of claim 1, wherein the amino acid variations are non-disruptive of polypeptide structure or function.

8. The method of claim 1, wherein each, overlapping polynucleotide is single-stranded.

9. The method of claim 1, wherein the plurality of overlapping palynucleotides comprises defined segments of the nucleic acids.

10. The method of claim 1, wherein the plurality of overlapping polynucleotides is reassembled in vitro.

11. The method of claim 1, wherein the plurality of overlapping polynucleotides is reassembled in vitro.

12. The method of claim 1, wherein the overlapping polynucleotides of step (d) are produced by a polymerase chain reaction.

13. The method of claim 1, wherein regions of overlap between members of the plurality of overlapping polynucleotides comprise about 10 to about 100 nucleotides in length.

14. The plurality of overlapping polynucleotides provided in step (d) of claim 1.

15. The method of claim 1, wherein step (e) comprises rassembling the plurality of polynucleotides using reassembly PCR.

16. The method of claim 1, wherein the nucleic acid sequences of step (a) comprise a library of nucleic acid sequences.

17. The method of claim 1, wherein the nucleic acid sequences of step (e) comprise sequences encoding full length genes.

18. The method of claim 1, wherein the subsequences encoding the ano acid vaation comprise at least one set of degenerate polynucleotides.

19. The method of claim 18, wherein the degenerate polynucleotides each comprise one or more degenerate codons.

20. The method of claim 1, further comprising fragmenting one or more of the nucleic acids encoding the plurality of homologous polypeptide sequences of step (d) to produce a set of nucleic acid fragments and wherein step (e) comprises reassembling the plurality of polynucleotides and the set of nucleic acid fragments into the nucleic acid sequences encoding the mutagenized polypeptides.

21. The method of claim 20, wherein the nucleic acids encoding the plurality of homologous polypeptide sequences are fragmented by one or more of, enzymatic digestion, DNase digestion, RNase digestion, restriction enzyme digestion, sonication, or shearing.

22. The method of claim 20, wherein each member of the set of nucleic alid fragments is from 5 bp to 5 kb in size.

23. The method of claim 1, wherein at least one member of the plurality of overlapping polynucleotides corresponds to an exon of at least one of the nucleic acids encoding the plurality of homologous polypeptide sequences.

24. The method of claim 23, wherein the exon encodes a structural element of a polypeptide selected from the group consisting of: loops, alpha helices, subdomains, whole domains, and hydrophobic cores.

25. The method of claim 1, further comprising:

(f) screening or selecting expressed polypeptides encoded by the nucleic acid sequences of step (e) for one or more desired properties.

26. The method of claim 25, wherein step (f) comprises:

(i) introducing the nucleic acid sequences into a cell population;

(ii) expressing the nucleic acid sequences in the cell population to produce one or more expressed polypeptides; and, (iii) selecting or screening one or more members of the cell population or the one of more expressed polypeptides for the one or more desired properties.

27. The method of claim 25, further comprising:

(g) repeating steps (d)–(f) using at least one polypeptide screened or selected in step (f) as at least one source of amino acid variation to be included in the polynucleotides provided in step (d).

* * * * *

SEQUENCE LISTING

```
<160> NUMBER OF SEQ ID NOS: 101

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 1
aaccctccag ttccgaaccc catatgatga tcaccctgcg taaactgccg              50

<210> SEQ ID NO 2
<211> LENGTH: 38
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 2
aaccctccag ttccgaaccc catatgaaaa aaaccgct                           38

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 3
aaccctccag ttccgaaccc atatacatat gcgtgctaaa                         40

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: degenerate
      oligonucleotide used for codon usage library
```

<400> SEQUENCE: 4
aaccctccag ttccgaaccc catatgaaat acctgctgcc gacc                44

<210> SEQ ID NO 5
<211> LENGTH: 40
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 5
aaccctccag ttccgaaccc gatatacata tgaaacagtc                     40

<210> SEQ ID NO 6
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 6
tggtgttatg tctgctcagg cdatggcdgt dgayttycay ctggttccgg ttgaagagga    60

<210> SEQ ID NO 7
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 7
ggctggtttc gctaccgttg cdcargcdgc dccdaargay ctggttccgg ttgaagagga    60

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 8 cacccgatc gctatctctt cyttygcdtc yacyggytcy ctggttccgg ttgaagagga    60

<210> SEQ ID NO 9
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 9
gctgctggct gctcagccgg cdatggcdat ggayatyggy ctggttccgg ttgaagagga    60

<210> SEQ ID NO 10
<211> LENGTH: 61
<212> TYPE: DNA
<213> ORGANISM: Artificial Sequence
<220> FEATURE:
<223> OTHER INFORMATION: Description of Artificial Sequence: degenerate
      oligonucleotide used for codon usage library

```
<400> SEQUENCE: 10
tgccgctgct gttcaccccg gtdacyaarg cdgcdcargt dctggttccg gttgaagagg      60
a                                                                     61

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 11
cccggctttc tggaaccgtc argcdgcdca rgcdctggac gttgctaaaa aactgcagcc      60

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 12
acgttatcct gttcctgggt gayggyatgg gygtdccdac cgttaccgct acccgtatcc     60

<210> SEQ ID NO 13
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 13
aaactgggtc cggaaacccc dctggcdatg gaycarttyc cgtacgttgc tctgtctaaa     60

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 14
ggttccggac tctgctggta cygcdacygc dtayctgtgc ggtgttaaag gtaactaccg     60

<210> SEQ ID NO 15
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 15
ctgctcgtta caaccagtgc aaracyacyc gyggyaayga agttacctct gttatgaacc     60

<210> SEQ ID NO 16
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library
```

<400> SEQUENCE: 16
tctgttggtg ttgttaccac yacycgygtd carcaygcdt ctccggctgg tgcttacgct      60

<210> SEQ ID NO 17
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 17
gtactctgac gctgacctgc cdgcdgaygc dcaratgaac ggttgccagg acatcgctgc      60

<210> SEQ ID NO 18
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 18
acatcgacgt tatcctgggt ggyggycgya artayatgtt cccggttggt accccggacc      60

<210> SEQ ID NO 19
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 19
tctgttaacg gtgttcgtaa rcgyaarcar aayctggtdc aggcttggca ggctaaacac      60

<210> SEQ ID NO 20
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 20
gaaccgtacc gctctgctgc argcdgcdga ygaytcytct gttacccacc tgatgggtct      60

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 21
aatacaacgt tcagcaggac cayacyaarg ayccdacyct gcaggaaatg accgaagttg      60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

```
<400> SEQUENCE: 22
aacccgcgtg gtttctacct gttygtdgar ggyggycgya tcgaccacgg tcaccacgac        60

<210> SEQ ID NO 23
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 23
gaccgaagct ggtatgttcg ayaaygcdat ygcdaargct aacgaactga cctctgaact        60

<210> SEQ ID NO 24
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 24
ccgctgacca ctctcacgtt ttytcyttyg gyggytayac cctgcgtggt acctctatct        60

<210> SEQ ID NO 25
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 25
gctctggact ctaaatctta yacytcyaty ctgtayggya acggtccggg ttacgctctg        60

<210> SEQ ID NO 26
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 26
cgttaacgac tctacctctg argayccdtc ytaycarcag caggctgctg ttccgcaggc        60

<210> SEQ ID NO 27
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 27
aagacgttgc tgttttcgct cgyggyccdc argcdcayct ggttcacggt gttgaagaag        60

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 28
```
atggctttcg ctggttgcgt dgarccdtay acygaytgya acctgccggc tccgaccacc        60

<210> SEQ ID NO 29
<211> LENGTH: 61
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 29
tgctcacctg gctgcttmac cdccdccdct ggcdctgctg gctggtgcta tgctgctcct        60
c                                                                        61

<210> SEQ ID NO 30
<211> LENGTH: 62
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 30
ttccgcctct agagaattct tartacagrg thgghgccag gaggagcagc atagcaccag        60
cc                                                                       62

<210> SEQ ID NO 31
<211> LENGTH: 58
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 31
aagcagccag gtgagcagcg tchggratrg argthgcggt ggtcggagcc ggcaggtt          58

<210> SEQ ID NO 32
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 32
cgcaaccagc gaaagccatg atrtghgcha craargtytc ttcttcaaca ccgtgaacca        60

<210> SEQ ID NO 33
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 33
gcgaaaacag caacgtcttc rccrccrtgr gtytcrgahg cctgcggaac agcagcctgc        60

<210> SEQ ID NO 34
<211> LENGTH: 60
<212> TYPE: DNA
<213> ORGANISM: Artificial Sequence
<220> FEATURE:
<223> OTHER INFORMATION: Description of Artificial Sequence: degenerate oligonucleotide used for codon usage library

<400> SEQUENCE: 34
agaggtagag tcgttaacgt chggrcgrga rccrccrccc agagcgtaac ccggaccgtt    60

<210> SEQ ID NO 35
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 35
aagatttaga gtccagagct ttrgahgghg ccagrccraa gatagaggta ccacgcaggg    60

<210> SEQ ID NO 36
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 36
acgtgagagt ggtcagcggt haccagratc agrgtrtcca gttcagaggt cagttcgtta    60

<210> SEQ ID NO 37
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 37
gaacatacca gcttcggtca ghgccatrta hgcyttrtcg tcgtggtgac cgtggtcgat    60

<210> SEQ ID NO 38
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 38
ggtagaaacc acgcgggtta cgrgahacha crcgcaghgc aacttcggtc atttcctgca    60

<210> SEQ ID NO 39
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 39
tcctgctgaa cgttgtattt catrtchgch ggytcraaca gacccatcag gtgggtaaca    60

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 40
cagcagagcg gtacggttcc ahacrtaytg hgcrccytgg tgtttagcct gccaagcctg     60

<210> SEQ ID NO 41
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 41
tacgaacacc gttaacagaa gcrtcrtchg grtaytchgg gtccggggta ccaaccggga     60

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 42
cccaggataa cgtcgatgtc catrttrtth accagytghg cagcgatgtc ctggcaaccg     60

<210> SEQ ID NO 43
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 43
caggtcagcg tcagagtacc arttrcgrtt hacrgtrtga gcgtaagcac cagccggaga     60

<210> SEQ ID NO 44
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 44
tggtaacaac accaacagat ttrcchgcyt tytthgcrcg gttcataaca gaggtaactt     60

<210> SEQ ID NO 45
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 45
cactggttgt aacgagcagc hgcrgahacr ccratrgtrc ggtagttacc tttaacaccg     60

<210> SEQ ID NO 46
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

```
<400> SEQUENCE: 46
accagcagag tccggaacct grcgrtchac rttrtargtt ttagacagag caacgtacgg      60

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 47
gggtttccgg acccagttta ccrttcatyt grccyttcag gatacgggta gcggtaacgg      60

<210> SEQ ID NO 48
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 48
cccaggaaca ggataacgtt ytthgchgcr gtytgrathg gctgcagttt tttagcaacg      60

<210> SEQ ID NO 49
<211> LENGTH: 42
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 49
acggttccag aaagccgggt cttcctcttc aaccggaacc ag                        42

<210> SEQ ID NO 50
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 50
cctgagcaga cataacacca gchgchachg chachgccag cggcagttta cgcagggtga      60

<210> SEQ ID NO 51
<211> LENGTH: 62
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 51
accggggtga acagcagcgg cagcaghgcc aghgcratrg trgactgttt catatgtata      60
tc                                                                    62

<210> SEQ ID NO 52
<211> LENGTH: 59
<212> TYPE: DNA
<213> ORGANISM: Artificial Sequence
<220> FEATURE:
<223> OTHER INFORMATION: Description of Artificial Sequence: degenerate
      oligonucleotide used for codon usage library
```

<400> SEQUENCE: 52
gccggctgag cagccagcag cagcagrcch gchgchgcgg tcggcagcag gtagtttca      59

<210> SEQ ID NO 53
<211> LENGTH: 60
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 53
aagagatagc gatcggggtg gtcaghacra trcccagcag tttagcacgc atatgtatat     60

<210> SEQ ID NO 54
<211> LENGTH: 58
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 54
caacggtagc gaaaccagcc aghgchachg crathgcrat agcggttttt ttcatatg      58

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 55
agaattctct agaggcggaa actctccaac tcccaggtt                             39

<210> SEQ ID NO 56
<211> LENGTH: 39
<212> TYPE: DNA
<213> ORGANISM: Artificial Sequence
<220> FEATURE:
<223> OTHER INFORMATION: Description of Artificial Sequence: degenerate
      oligonucleotide used for codon usage library

<400> SEQUENCE: 56
tgagaggttg agggtccaat tgggaggtca aggcttggg                             39

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 57
tgtratctgy ctsagacc                                                    18

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: degenerate
      oligonucleotide used for alpha interferon -continued shuffling

<400> SEQUENCE: 58
ggcacaaatg vgmagaatct ctc                                   23

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 59
agagattctk cbcatttgtg cc                                    22

<210> SEQ ID NO 60
<211> LENGTH: 24
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 60
cagttccaga agrctsmagc catc                                  24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 61
gatggctksa gycttctgga actg                                  24

<210> SEQ ID NO 62
<211> LENGTH: 19
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 62
cttcaatctc ttcascaca                                        19

<210> SEQ ID NO 63
<211> LENGTH: 19
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 63
tgtgstgaag agattgaag                                        19

<210> SEQ ID NO 64
<211> LENGTH: 18

```
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 64
ggawsagass ctcctaga                                                 18

<210> SEQ ID NO 65
<211> LENGTH: 18
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 65
tctaggagss tctswtcc                                                 18

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 66
gaacttdwcc agcaamtgaa t                                             21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 67
attcakttgc tggwhaagtt c                                             21

<210> SEQ ID NO 68
<211> LENGTH: 19
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 68
ggactycatc ctggctgtg                                                19

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 69
```
cacagccagg atgragtcc                                                19

<210> SEQ ID NO 70
<211> LENGTH: 18
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 70
aagaatcact ctttatct                                                 18

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 71
agataaagag tgattctt                                                 18

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 72
tgggaggttg tcagagcag                                                19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 73
ctgctctgac aacctccca                                                19

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: degenerate
      oligonucleotide used for alpha interferon
      shuffling

<400> SEQUENCE: 74
tcawtccttm ctcyttaa                                                 18

<210> SEQ ID NO 75
<211> LENGTH: 166
<212> TYPE: PRT
<213> ORGANISM: consensus alpha interferon

<400> SEQUENCE: 75

```
Cys Asp Leu Pro Gln Thr His Ser Leu Gly Asn Arg Arg Ala Leu Ile
 1               5                  10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
            35                  40                  45

Gln Lys Ala Gln Ala Ile Ser Val Leu His Glu Met Ile Gln Gln Thr
        50                  55                  60

Phe Asn Leu Phe Ser Thr Lys Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 76
<211> LENGTH: 166
<212> TYPE: PRT
<213> ORGANISM: human alpha interferon

<400> SEQUENCE: 76

Cys Asp Leu Pro Gln Thr His Ser Leu Gly Asn Arg Arg Ala Leu Ile
 1               5                  10                  15

Leu Leu Ala Gln Met Gly Arg Ile Ser Pro Phe Ser Cys Leu Lys Asp
            20                  25                  30

Arg His Asp Phe Gly Leu Pro Gln Glu Glu Phe Asp Gly Asn Gln Phe
            35                  40                  45

Gln Lys Thr Gln Ala Ile Pro Val Leu His Glu Met Ile Gln Gln Thr
        50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
        130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 77
<211> LENGTH: 166
<212> TYPE: PRT
```

<213> ORGANISM: human alpha interferon

<400> SEQUENCE: 77

Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg Pro Asp Phe Gly Leu Pro Gln Glu Glu Phe Asp Gly Asn Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asn Leu
                85                  90                  95

Glu Ala Cys Val Ile Gln Glu Val Gly Met Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 78
<211> LENGTH: 166
<212> TYPE: PRT
<213> ORGANISM: human alpha interferon

<400> SEQUENCE: 78

Cys Asn Leu Ser Gln Thr His Ser Leu Asn Asn Arg Arg Thr Leu Met
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Gly Asn Gln Phe
        35                  40                  45

Gln Lys Ala Gln Ala Ile Ser Val Leu His Glu Met Met Gln Gln Thr
    50                  55                  60

Phe Asn Leu Phe Ser Thr Lys Asn Ser Ser Ala Ala Trp Asp Glu Thr
65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Lys Lys Tyr Phe Gln Arg Ile Thr
            115                 120                 125

Leu Tyr Leu Met Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

```
<210> SEQ ID NO 79
<211> LENGTH: 166
<212> TYPE: PRT
<213> ORGANISM: human alpha interferon

<400> SEQUENCE: 79

Cys Asp Leu Pro Gln Thr His Ser Leu Gly Asn Arg Ala Leu Ile
 1               5                  10                  15

Leu Leu Ala Gln Met Gly Arg Ile Ser His Phe Ser Cys Leu Lys Asp
                20                  25                  30

Arg His Asp Phe Gly Phe Pro Glu Glu Glu Phe Asp Gly His Gln Phe
            35                  40                  45

Gln Lys Thr Gln Ala Ile Ser Val Leu His Glu Met Ile Gln Gln Thr
        50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Arg Leu Arg Arg Lys Asp
                165

<210> SEQ ID NO 80
<211> LENGTH: 166
<212> TYPE: PRT
<213> ORGANISM: human alpha interferon

<400> SEQUENCE: 80

Cys Asp Leu Pro Gln Thr His Ser Leu Gly His Arg Arg Thr Met Met
 1               5                  10                  15

Leu Leu Ala Gln Met Arg Arg Ile Ser Leu Phe Ser Cys Leu Lys Asp
                20                  25                  30

Arg His Asp Phe Arg Phe Pro Gln Glu Glu Phe Asp Gly Asn Gln Phe
            35                  40                  45

Gln Lys Ala Glu Ala Ile Ser Val Leu His Glu Val Ile Gln Gln Thr
        50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe Ser Ser Arg Asn Leu Gln Glu
145                 150                 155                 160

Arg Leu Arg Arg Lys Glu
```

```
                        165

<210> SEQ ID NO 81
<211> LENGTH: 166
<212> TYPE: PRT
<213> ORGANISM: human alpha interferon

<400> SEQUENCE: 81

Cys Asp Leu Pro Gln Thr His Ser Leu Arg Asn Arg Ala Leu Ile
  1               5                  10                  15

Leu Leu Ala Gln Met Gly Arg Ile Ser Pro Phe Ser Cys Leu Lys Asp
                 20                  25                  30

Arg His Glu Phe Arg Phe Pro Glu Glu Glu Phe Asp Gly His Gln Phe
             35                  40                  45

Gln Lys Thr Gln Ala Ile Ser Val Leu His Glu Met Ile Gln Gln Thr
         50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asp Leu
                 85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
            115                 120                 125

Leu Tyr Leu Met Glu Lys Lys Tyr Ser Pro Cys Ala Trp Glu Val Val
        130                 135                 140

Arg Ala Glu Ile Met Arg Ser Phe Ser Phe Ser Thr Asn Leu Lys Lys
145                 150                 155                 160

Gly Leu Arg Arg Lys Asp
                165

<210> SEQ ID NO 82
<211> LENGTH: 166
<212> TYPE: PRT
<213> ORGANISM: human alpha interferon

<400> SEQUENCE: 82

Cys Asp Leu Pro Gln Thr His Ser Leu Gly Asn Arg Arg Ala Leu Ile
  1               5                  10                  15

Leu Leu Ala Gln Met Arg Arg Ile Ser Pro Phe Ser Cys Leu Lys Asp
                 20                  25                  30

Arg His Asp Phe Glu Phe Pro Gln Glu Glu Phe Asp Asp Lys Gln Phe
             35                  40                  45

Gln Lys Ala Gln Ala Ile Ser Val Leu His Glu Met Ile Gln Gln Thr
         50                  55                  60

Phe Asn Leu Phe Ser Thr Lys Asp Ser Ser Ala Ala Leu Asp Glu Thr
 65                  70                  75                  80

Leu Leu Asp Glu Phe Tyr Ile Glu Leu Asp Gln Gln Leu Asn Asp Leu
                 85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
            115                 120                 125

Leu Tyr Leu Thr Glu Lys Lys Tyr Ser Ser Cys Ala Trp Glu Val Val
        130                 135                 140

Arg Ala Glu Ile Met Arg Ser Phe Ser Leu Ser Ile Asn Leu Gln Lys
```

145              150              155              160

Arg Leu Lys Ser Lys Glu
             165

<210> SEQ ID NO 83
<211> LENGTH: 166
<212> TYPE: PRT
<213> ORGANISM: human alpha interferon

<400> SEQUENCE: 83

Cys Asp Leu Pro Glu Thr His Ser Leu Asp Asn Arg Arg Thr Leu Met
 1               5                  10                  15

Leu Leu Ala Gln Met Ser Arg Ile Ser Pro Ser Ser Cys Leu Met Asp
             20                  25                  30

Arg His Asp Phe Gly Phe Pro Gln Glu Glu Phe Asp Gly Asn Gln Phe
         35                  40                  45

Gln Lys Ala Pro Ala Ile Ser Val Leu His Glu Leu Ile Gln Gln Ile
     50                  55                  60

Phe Asn Leu Phe Thr Thr Lys Asp Ser Ser Ala Ala Trp Asp Glu Asp
 65                  70                  75                  80

Leu Leu Asp Lys Phe Cys Thr Glu Leu Tyr Gln Gln Leu Asn Asp Leu
                 85                  90                  95

Glu Ala Cys Val Met Gln Glu Glu Arg Val Gly Glu Thr Pro Leu Met
             100                 105                 110

Asn Ala Asp Ser Ile Leu Ala Val Lys Lys Tyr Phe Arg Arg Ile Thr
         115                 120                 125

Leu Tyr Leu Thr Glu Lys Lys Tyr Ser Pro Cys Ala Trp Glu Val Val
     130                 135                 140

Arg Ala Glu Ile Met Arg Ser Leu Ser Leu Ser Thr Asn Leu Gln Glu
145                 150                 155                 160

Arg Leu Arg Arg Lys Glu
            165

<210> SEQ ID NO 84
<211> LENGTH: 166
<212> TYPE: PRT
<213> ORGANISM: human alpha interferon

<400> SEQUENCE: 84

Cys Asp Leu Pro Gln Thr His Ser Leu Gly Asn Arg Arg Ala Leu Ile
 1               5                  10                  15

Leu Leu Ala Gln Met Gly Arg Ile Ser Pro Phe Ser Cys Leu Lys Asp
             20                  25                  30

Arg His Asp Phe Gly Phe Pro Gln Glu Glu Phe Asp Gly Asn Gln Phe
         35                  40                  45

Gln Lys Ala Gln Ala Ile Ser Val Leu His Glu Met Ile Gln Gln Thr
     50                  55                  60

Phe Asn Leu Phe Ser Thr Lys Asp Ser Ser Ala Ile Trp Glu Gln Ser
 65                  70                  75                  80

Leu Leu Glu Lys Phe Ser Thr Glu Leu Asn Gln Gln Leu Asn Asp Met
                 85                  90                  95

Glu Ala Cys Val Ile Gln Glu Val Gly Val Glu Thr Pro Leu Met
             100                 105                 110

Asn Val Asp Ser Ile Leu Ala Val Lys Lys Tyr Phe Gln Arg Ile Thr
         115                 120                 125

Leu Tyr Leu Thr Glu Lys Lys Tyr Ser Pro Cys Ala Trp Glu Val Val

```
                130             135             140
Arg Ala Glu Ile Met Arg Ser Phe Ser Leu Ser Lys Ile Phe Gln Glu
145                 150                 155                 160

Arg Leu Arg Arg Lys Ser
                165

<210> SEQ ID NO 85
<211> LENGTH: 166
<212> TYPE: PRT
<213> ORGANISM: human alpha interferon

<400> SEQUENCE: 85

Cys Asp Leu Pro Gln Thr His Ser Leu Gly Asn Arg Arg Ala Leu Ile
  1               5                  10                  15

Leu Leu Ala Gln Met Gly Arg Ile Ser Pro Phe Ser Cys Leu Lys Asp
                 20                  25                  30

Arg Pro Asp Phe Gly Leu Pro Gln Glu Phe Asp Gly Asn Gln Phe
             35                  40                  45

Gln Lys Thr Gln Ala Ile Ser Val Leu His Glu Met Ile Gln Gln Thr
     50                  55                  60

Phe Asn Leu Phe Ser Thr Glu Asp Ser Ser Ala Ala Trp Glu Gln Ser
 65                  70                  75                  80

Leu Leu Glu Lys Phe Ser Thr Glu Leu Tyr Gln Gln Leu Asn Asn Leu
                 85                  90                  95

Glu Ala Cys Val Ile Gln Glu Val Gly Met Glu Thr Pro Leu Met
                100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
    130                 135                 140

Arg Ala Glu Ile Met Arg Ser Leu Ser Phe Ser Thr Asn Leu Gln Lys
145                 150                 155                 160

Ile Leu Arg Arg Lys Asp
                165

<210> SEQ ID NO 86
<211> LENGTH: 166
<212> TYPE: PRT
<213> ORGANISM: human alpha interferon

<400> SEQUENCE: 86

Cys Asp Leu Pro Gln Thr His Ser Leu Gly Asn Arg Arg Ala Leu Ile
  1               5                  10                  15

Leu Leu Ala Gln Met Gly Arg Ile Ser His Phe Ser Cys Leu Lys Asp
                 20                  25                  30

Arg Tyr Asp Phe Gly Phe Pro Gln Glu Val Phe Asp Gly Asn Gln Phe
             35                  40                  45

Gln Lys Ala Gln Ala Ile Ser Ala Phe His Glu Met Ile Gln Gln Thr
     50                  55                  60

Phe Asn Leu Phe Ser Thr Lys Asp Ser Ser Ala Ala Trp Asp Glu Thr
 65                  70                  75                  80

Leu Leu Asp Lys Phe Tyr Ile Glu Leu Phe Gln Gln Leu Asn Asp Leu
                 85                  90                  95

Glu Ala Cys Val Thr Gln Glu Val Gly Val Glu Glu Ile Ala Leu Met
                100                 105                 110

Asn Glu Asp Ser Ile Leu Ala Val Arg Lys Tyr Phe Gln Arg Ile Thr
```

```
                115                 120                 125
Leu Tyr Leu Met Gly Lys Lys Tyr Ser Pro Cys Ala Trp Glu Val Val
            130                 135                 140

Arg Ala Glu Ile Met Arg Ser Phe Ser Phe Ser Thr Asn Leu Gln Lys
145                 150                 155                 160

Gly Leu Arg Arg Lys Asp
                165

<210> SEQ ID NO 87
<211> LENGTH: 501
<212> TYPE: DNA
<213> ORGANISM: consensus alpha interferon

<400> SEQUENCE: 87
tgtgatctgc ctcagaccca cagcctgggt aataggaggg ccttgatact cctggcacaa      60
atgggaagaa tctctccttt ctcctgcctg aaggacagac atgactttgg atttccccag     120
gaggagtttg atggcaacca gttccagaag ctcaagcca tctctgtcct ccatgagatg      180
atccagcaga ccttcaatct cttcagcaca aaggactcat ctgctgcttg ggatgagagc     240
ctcctagaaa aattttccac tgaactttac cagcaactga atgacctgga agcctgtgtg     300
atacaggagg ttggggtgga agagactccc ctgatgaatg aggactccat cctggctgtg     360
aggaaatact tccaaagaat cactctttat ctgacagaga gaaatacag cccttgtgcc      420 tgggaggttg tcagagcaga aatcatgaga tccttctctt tttcaacaaa cttgcaaaaa     480
agattaagga ggaaggattg a                                               501

<210> SEQ ID NO 88
<211> LENGTH: 501
<212> TYPE: DNA
<213> ORGANISM: human alpha interferon

<400> SEQUENCE: 88
tgtgatctgc ctcagaccca cagcctgggt aataggaggg ccttgatact cctggcacaa      60
atgggaagaa tctctccttt ctcctgcctg aaggacagac atgactttgg acttccccag     120
gaggagtttg atggcaacca gttccagaag actcaagcca tccctgtcct ccatgagatg     180
atccagcaga ccttcaatct cttcagcaca gaggactcat ctgctgcttg gaacagagc      240 ctcctagaaa aattttccac tgaactttac cagcaactga ataacctgga agcatgtgtg     300
atagaggagg ttgggatgga agagactccc ctgatgaatg aggactccat cctggctgtg     360
aggaaatact tccaaagaat cactctttat ctaacagaga gaaatacag cccttgtgcc      420 tgggaggttg tcagagcaga aatcatgaga tccctctctt tttcaacaaa cttgcaaaaa     480
agattaagga ggaaggattg a                                               501

<210> SEQ ID NO 89
<211> LENGTH: 501
<212> TYPE: DNA
<213> ORGANISM: human alpha interferon

<400> SEQUENCE: 89
tgtgatctgc ctcagaccca cagcctgggt aataggaggg ccttgatact cctggcacaa      60
atgggaagaa tctctccttt ctcctgcctg aaggacagac ctgactttgg acttccccag     120
gaggagtttg atggcaacca gttccagaag actcaagcca tctctgtcct ccatgagatg     180
atccagcaga ccttcaatct cttcagcaca gaggactcat ctgctgcttg gaacagagc      240
```

-continued

```
ctcctagaaa aattttccac tgaactttac cagcaactga ataacctgga agcatgtgtg    300
atacaggagg ttgggatgga agagactccc ctgatgaatg aggactccat cctggctgtg    360
aggaaatact tccaaagaat cactctttat ctaacagaga agaaatacag cccttgtgcc    420
tgggaggttg tcagagcaga aatcatgaga tctctctctt tttcaacaaa cttgcaaaaa    480
atattaagga ggaaggattg a                                              501
```

<210> SEQ ID NO 90
<211> LENGTH: 501
<212> TYPE: DNA
<213> ORGANISM: human alpha interferon

<400> SEQUENCE: 90

```
tgtaatctgt ctcaaaccca cagcctgaat aacaggagga ctttgatgct catggcacaa    60
atgaggagaa tctctccttt ctcctgcctg aaggacagac atgactttga atttccccag    120
gaggaatttg atggcaacca gttccagaaa gctcaagcca tctctgtcct ccatgagatg    180
atgcagcaga ccttcaatct cttcagcaca agaactcat  ctgctgcttg ggatgagacc    240
ctcctagaaa aattctacat tgaacttttc cagcaaatga atgacctgga agcctgtgtg    300
atacaggagg ttggggtgga agagactccc ctgatgaatg aggactccat cctggctgtg    360
aagaaatact tccaaagaat cactctttat ctgatggaga agaaatacag cccttgtgcc    420
tgggaggttg tcagagcaga aatcatgaga tccctctctt tttcaacaaa cttgcaaaaa    480
agattaagga ggaaggattg a                                              501
```

<210> SEQ ID NO 91
<211> LENGTH: 501
<212> TYPE: DNA
<213> ORGANISM: human alpha interferon

<400> SEQUENCE: 91

```
tgtgatctgc ctcagaccca cagcctgggt aataggaggg ccttgatact cctggcacaa    60
atgggaagaa tctctccttt ctcatgcctg aaggacagac atgatttcgg attccccgag    120
gaggagtttg atggccacca gttccagaag actcaagcca tctctgtcct ccatgagatg    180
atccagcaga ccttcaatct cttcagcaca gaggactcat ctgctgcttg ggaacagagc    240
ctcctagaaa aattttccac tgaactttac cagcaactga atgacctgga agcatgtgtg    300
atacaggagg ttggggtgga agagactccc ctgatgaatg tggactccat cctggctgtg    360
aggaaatact tccaaagaat cactctttat ctaacagaga agaaatacag cccttgtgcc    420
tgggaggttg tcagagcaga aatcatgaga tccctctcgt tttcaacaaa cttgcaaaaa    480
agattaagga ggaaggattg a                                              501
```

<210> SEQ ID NO 92
<211> LENGTH: 501
<212> TYPE: DNA
<213> ORGANISM: human alpha interferon

<400> SEQUENCE: 92

```
tgtgatctgc ctcagaccca cagcctgggt cacaggagga ccatgatgct cctggcacaa    60
atgaggagaa tctctctttt ctcctgtctg aaggacagac atgacttcag atttccccag    120
gaggagtttg atggcaacca gttccagaag gctgaagcca tctctgtcct ccatgaggtg    180
attcagcaga ccttcaatct cttcagcaca aaggactcat ctgttgcttg ggatgagagg    240
cttctagaca aactctatac tgaactttac cagcagctga atgacctgga agcctgtgtg    300
```

```
atgcaggagg tgtgggtggg agggactccc ctgatgaatg aggactccat cctggctgtg      360
agaaaatact tccaaagaat cactctctac ctgacagaga aaaagtacag cccttgtgcc      420
tgggaggttg tcagagcaga aatcatgaga tccttctctt catcaagaaa cttgcaagaa      480
aggttaagga ggaaggaata a                                                501

<210> SEQ ID NO 93
<211> LENGTH: 501
<212> TYPE: DNA
<213> ORGANISM: human alpha interferon

<400> SEQUENCE: 93
tgtgatctgc ctcagaccca cagcctgcgt aataggaggg ccttgatact cctggcacaa       60
atgggaagaa tctctccttt ctcctgcttg aaggacagac atgaattcag attcccagag      120
gaggagtttg atggccacca gttccagaag actcaagcca tctctgtcct ccatgagatg      180
atccagcaga ccttcaatct cttcagcaca gaggactcat ctgctgcttg gaacagagc      240 ctcctagaaa aattttccac tgaactttac cagcaactga atgacctgga agcatgtgtg      300
atacaggagg ttggggtgga agagactccc ctgatgaatg aggactccat cctggctgtg      360
aggaaatact tccaaagaat cactctttat ctaatggaga agaaatacag cccttgtgcc      420
tgggaggttg tcagagcaga aatcatgaga tccttctctt tttcaacaaa cttgaaaaaa      480
ggattaagga ggaaggattg a                                                501

<210> SEQ ID NO 94
<211> LENGTH: 501
<212> TYPE: DNA
<213> ORGANISM: human alpha interferon

<400> SEQUENCE: 94
tgtgatctgc ctcagactca cagcctgggt aacaggaggg ccttgatact cctggcacaa       60
atgcgaagaa tctctccttt ctcctgcctg aaggacagac atgactttga attccccag      120 gaggagtttg atgataaaca gttccagaag gctcaagcca tctctgtcct ccatgagatg      180
atccagcaga ccttcaacct cttcagcaca aaggactcat ctgctgcttt ggatgagacc      240
cttctagatg aattctacat cgaacttgac cagcagctga atgacctgga gtcctgtgtg      300
atgcaggaag tgggggtgat agagtctccc ctgatgaatg aggacttcat cctggctgtg      360
aggaaatact tccaaagaat cactctatat ctgacagaga agaaatacag ctcttgtgcc      420
tgggaggttg tcagagcaga aatcatgaga tccttctctt tatcaatcaa cttgcaaaaa      480
agattgaaga gtaaggaatg a                                                501

<210> SEQ ID NO 95
<211> LENGTH: 501
<212> TYPE: DNA
<213> ORGANISM: human alpha interferon

<400> SEQUENCE: 95
tgtgatctcc ctgagaccca cagcctggat aacaggagga ccttgatgct cctggcacaa       60
atgagcagaa tctctccttc ctcctgtctg atggacagac atgactttgg atttccccag      120
gaggagtttg atggcaacca gttccagaag gctccagcca tctctgtcct ccatgagctg      180
atccagcaga tcttcaacct cttctccaca aaagattcat ctgctgcttg ggatgaggac      240
ctcctagaca aattctgcac cgaactctac cagcagctga atgacttgga agcctgtgtg      300
```

| atgcaggagg agagggtggg agaaactccc ctgatgtacg cggactccat cctggctgtg | 360 |
| aagaaatact tccaaagaat cactctctat ctgacagaga agaaatacag cccttgtgcc | 420 |
| tgggaggttg tcagagcaga aatcatgaga tccctctctt tatcaacaaa cttgcaagaa | 480 |
| agattaagga ggaaggaata a | 501 |

<210> SEQ ID NO 96
<211> LENGTH: 501
<212> TYPE: DNA
<213> ORGANISM: human alpha interferon

<400> SEQUENCE: 96

| tgtgatctgc ctcagaccca cagcctgggt aataggaggg ccttgatact cctggcacaa | 60 |
| atgggaagaa tctctccttt ctcctgcctg aaggacagac atgactttgg attcccccaa | 120 |
| gaggagtttg atgcaacca gttccagaag gctcaagcca tctctgtcct ccatgagatg | 180 |
| atccagcaga ccttcaatct cttcagcaca aaggactcat ctgctacttg ggaacagagc | 240 |
| ctcctagaaa aatttccac tgaacttaac cagcagctga atgacatgga agcctgcgtg | 300 |
| atacaggagg ttggggtgga agagactccc ctgatgaatg tggactctat cctggctgtg | 360 |
| aagaaatact tccaaagaat cactctttat ctgacagaga agaaatacag cccttgtgct | 420 |
| tgggaggttg tcagagcaga aatcatgaga tccttctctt tatcaaaaat ttttcaagaa | 480 |
| agattaagga ggaaggaatg a | 501 |

<210> SEQ ID NO 97
<211> LENGTH: 501
<212> TYPE: DNA
<213> ORGANISM: human alpha interferon

<400> SEQUENCE: 97

| tgtgatctgc ctcagaccca cagcctgggt aataggaggg ccttgatact cctggcacaa | 60 |
| atgggaagaa tctctccttt ctcctgcctg aaggacagac ctgactttgg acttccccag | 120 |
| gaggagtttg atgcaacca gttccagaag actcaagcca tctctgtcct ccatgagatg | 180 |
| atccagcaga ccttcaatct cttcagcaca gaggactcat ctgctgcttg ggaacagagc | 240 |
| ctcctagaaa aatttccac tgaactttac cagcaactga ataacctgga agcatgtgtg | 300 |
| atacaggagg ttgggatgga agagactccc ctgatgaatg aggactccat cttggctgtg | 360 |
| aggaaatact tccaaagaat cactctttat ctaacagaga agaaatacag cccttgtgcc | 420 |
| tgggaggttg tcagagcaga aatcatgaga tctctctctt tttcaacaaa cttgcaaaaa | 480 |
| agattaagga ggaaggattg a | 501 |

<210> SEQ ID NO 98
<211> LENGTH: 501
<212> TYPE: DNA
<213> ORGANISM: human alpha interferon

<400> SEQUENCE: 98

| tgtgatctgc ctcagactca cagcctgggt aataggaggg ccttgatact cctggcacaa | 60 |
| atgggaagaa tctctcattt ctcctgcctg aaggacagat atgatttcgg attcccccag | 120 |
| gaggtgtttg atgcaacca gttccagaag gctcaagcca tctctgccctt ccatgagatg | 180 |
| atccagcaga ccttcaatct cttcagcaca aaggattcat ctgctgcttg ggatgagacc | 240 |
| ctcctagaca aattctacat tgaactttc cagcaactga atgacctaga agcctgtgtg | 300 |
| acacaggagg ttggggtgga agagattgcc ctgatgaatg aggactccat cctggctgtg | 360 |

```
aggaaatact ttcaaagaat cactctttat ctgatggaga agaaatacag cccttgtgcc      420
tgggaggttg tcagagcaga aatcatgaga tccttctctt tttcaacaaa cttgcaaaaa      480
ggattaagaa ggaaggattg a                                                501

<210> SEQ ID NO 99
<211> LENGTH: 11
<212> TYPE: PRT
<213> ORGANISM: Artificial Sequence
<220> FEATURE:
<223> OTHER INFORMATION: Description of Artificial Sequence: Protease
      peptide substrate

<400> SEQUENCE: 99

Arg Gly Val Val Asn Ala Ser Ser Arg Leu Ala
 1               5                  10

<210> SEQ ID NO 100
<211> LENGTH: 44
<212> TYPE: DNA
<213> ORGANISM: Artificial Sequence
<220> FEATURE:
<223> OTHER INFORMATION: Description of Artificial Sequence: Introduced
      Sfi I site

<400> SEQUENCE: 100
ttccatttca tacatggccg aaggggccgt gccatgagga tttt                       44

<210> SEQ ID NO 101
<211> LENGTH: 50
<212> TYPE: DNA
<213> ORGANISM: Artificial Sequence
<220> FEATURE:
<223> OTHER INFORMATION: Description of Artificial Sequence: Introduced
      sfi I site

<400> SEQUENCE: 101
ttctaaatgc atgttggcct ccttggccgg attctgagcc ttcaggacca                 50
```